US011059858B2

(12) United States Patent
Maerki et al.

(10) Patent No.: US 11,059,858 B2
(45) Date of Patent: Jul. 13, 2021

(54) DIFLUOROKETAMIDE DERIVATIVES AS HTRA1 INHIBITORS

(71) Applicant: Hoffmann-La Roche Inc., Little Falls, NJ (US)

(72) Inventors: Hans P. Maerki, Basel (CH); Benoit Hornsperger, Basel (CH); Peter Mohr, Basel (CH); Michael Reutlinger, Basel (CH); Roberto Iacone, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 16/121,244

(22) Filed: Sep. 4, 2018

(65) Prior Publication Data

US 2018/0371015 A1 Dec. 27, 2018

Related U.S. Application Data

(63) Continuation of application No. PCT/EP2017/054682, filed on Mar. 1, 2017.

(30) Foreign Application Priority Data

Mar. 4, 2016 (EP) .................................... 16158644

(51) Int. Cl.
| | |
|---|---|
| *C07K 5/083* | (2006.01) |
| *C07K 5/08* | (2006.01) |
| *C07K 5/087* | (2006.01) |
| *C07K 5/093* | (2006.01) |
| *C07K 5/103* | (2006.01) |
| *C07K 5/09* | (2006.01) |
| *C07K 5/065* | (2006.01) |
| *C07K 5/062* | (2006.01) |
| *C07K 5/06* | (2006.01) |

(52) U.S. Cl.
CPC .......... *C07K 5/0806* (2013.01); *C07K 5/0606* (2013.01); *C07K 5/06026* (2013.01); *C07K 5/06078* (2013.01); *C07K 5/06191* (2013.01); *C07K 5/081* (2013.01); *C07K 5/0812* (2013.01); *C07K 5/0815* (2013.01); *C07K 5/0819* (2013.01); *C07K 5/0827* (2013.01); *C07K 5/1008* (2013.01)

(58) Field of Classification Search
CPC .... C07K 5/0806; C07K 5/081; C07K 5/0827; C07K 5/0815; C07K 5/06078; C07K 5/0606; C07K 5/06026; C07K 5/06191; C07K 5/0812; C07K 5/0819; C07K 5/1008

See application file for complete search history.

(56) References Cited

U.S. PATENT DOCUMENTS

| | | |
|---|---|---|
| 9,980,929 B2 | 5/2018 | Hornsperger et al. |
| 10,428,108 B2 | 10/2019 | Hornsperger et al. |
| 2005/0027101 A1 | 2/2005 | Gutheil et al. |

FOREIGN PATENT DOCUMENTS

| | | | |
|---|---|---|---|
| EP | 2 371 839 A1 | 10/2011 | |
| WO | WO-8606379 A1 * | 11/1986 | ........... C07K 5/1024 |
| WO | 96/02499 A1 | 2/1996 | |
| WO | 99/07734 A2 | 2/1999 | |
| WO | 00/61542 A1 | 10/2000 | |
| WO | 2005/035525 A2 | 4/2005 | |
| WO | 2008/101160 A2 | 8/2008 | |
| WO | 2012/093101 A1 | 7/2012 | |
| WO | 2014/002053 A1 | 1/2014 | |
| WO | 2016/100555 A1 | 6/2016 | |
| WO | 2016/135070 A1 | 9/2016 | |
| WO | 2016/180751 A1 | 11/2016 | |

OTHER PUBLICATIONS

Ammar, M., et al., "What's Ahead for the Treatment of Dry AMD" Review Ophthalmology 27(3):60-65 (Mar 7, 2020) https://www.reviewofophthalmology.com/article/whats-ahead-for-the-treatment-of-dry-amd.

Cregge et al., "Inhibition of Human Neutrophil Elastase. 4. Design, Synthesis, X-ray Crystallographic Analysis, and Structure-Activity Relationships for a Series of P2-Modified, Orally Active Peptidyl Pentafluoroethyl Ketones" Journal of Medicinal Chemistry 41:2451-2480 ( 1998).

Derstine, C., et al., CAS Registry Database, 182001-67-8, 1996:494556 (Trifluoromethyl-Substituted Imidazolines: Novel Precursors of Trifluoromethyl Ketones Amenable to Peptide Synthesis), pp. 1Other Date Nov. 13, 2019, Abstract and the provided structure only.

He, M., et al., "The Association Between Diabetes and Age-Related Macular Degeneration Among the Elderly in Taiwan" Diabetes Care 41:2202-2211 (Oct. 1, 2018).

International Preliminary Report on Patentability (IPRP) for PCT/EP2017/067519 dated Jan. 22, 2019.

(Continued)

*Primary Examiner* — Li N Komatsu
(74) *Attorney, Agent, or Firm* — Bradley E. Davis

(57) ABSTRACT

The invention provides novel compounds having the general formula (I)

(I)

wherein $R^1$, $R^2$, $R^3$, $R^4$, $R^5$, $R^6$, $R^7$, $R^8$, $R^9$, $R^{10}$, $R^{11}$ and $R^{23}$ are as described herein, compositions including the compounds and methods of using the compounds.

38 Claims, No Drawings

Specification includes a Sequence Listing.

(56) References Cited

OTHER PUBLICATIONS

International Preliminary Report on Patentability—PCT/EP2017/071019:pp. 1-8 (dated Mar. 7, 2019).
International Search Report for PCT/EP2017/067519 dated Aug. 14, 2017.
International Search Report—PCT/EP2017/071019:pp. 1-8 (dated Sep. 27, 2017).
ISR and Written Opinion for PCT/EP2017/054677 (dated Jul. 4, 2017).
Jacobo, Sarah Melissa P. et al., "Focus on Molecules: HtrA1 and neovascular AMD" Experimental Eye Research (XP028884160), 94(1):4-5 ( 2012).
Knobbe, C., et al., "Macular degeneration prevention" All About Vision (Article retrieved from webpage: May 11, 2020; Last Update posted: Oct. 16, 2016),:1-12 (May 11, 2020) https://www.allaboutvision.com/conditions/amd-prevention.htm.
Perni et al., "Inhibitors of hepatitis C virus NS3.4A protease 2. Warhead SAR and optimization" Bioorganic & Medicinal Chemistry Letters 14(6): 1441-1446 ( 2004).
Sasubilli, Ramakrishna et al., "General Inverse Solid-Phase Synthesis Method for C-Terminally Modified Peptide Mimetics" Journal of Combinatorial Chemistry (XP002522469), 6(6):911-915 (Nov. 1, 2004).
Skiles et al., "Inhibition of human leukocyte elastase by N-substituted peptides containing a,a-Difluorostatone residues at P1" J. Med. Chem. 35:4795-4808 ( 1992).
Truebestein et al., "Substrate-induced remodeling of the active site regulates human HTRA1 activity" Nat. Struct. Mol. Biol. 18(3):386-388 (Feb. 6, 2011).
Bernstein, Peter R. et al., "Examination of Peptidic alpha-beta Diamino-alpha-alpha-difluoroketones as Inhibitors of human Leukocyte Elastase" Bioorganic and Medicinal Chemistry Letters (XP002768444), 4(18):2175-2178 (Oct. 1, 1994).
Doherty A. M. et al., "Design and Synthesis of Potent, Selective, and Orally Active Fluorine-Containing Renin Inhibitors" Journal of Medicinal Chemistry (XP002768443), 35:2-14 (Jan. 1, 1992).
Giovani, Simone et al., "Plasmodium falciparum subtilisin-like protease 1; discovery of potent difluorostatone-based inhibitors" RSC Advances (XP002768447), 5:22431-22448 (Feb. 19, 2015).
ISR and Written Opinion for PCT/EP2017/054682 (dated May 4, 2017).
Akahoshi et al., "Synthesis, Structure—Activity Relationships, and Pharmacokinetic Profiles of Nonpeptidic Difluoromethylene Ketones as Novel Inhibitors of Human Chymase" J. Med. Chem. 44(8):1297-1304 (2001).
International Preliminary Report on Patentability (IPRP) for PCT/EP2017/070985 dated Feb. 26, 2019.
International Search Report for PCT/EP2017/070985 dated Sep. 25, 2017.
Liver disease, Mayo Clinic, <https://www.rnayoclinic.org/diseases-conditions/liver-problems/syrmptorns-causes/syc-20374502>, Accessed Mar. 1, 2020.

* cited by examiner

DIFLUOROKETAMIDE DERIVATIVES AS HTRA1 INHIBITORS

RELATED APPLICATIONS

This application is a continuation of International Application No. PCT/EP2017/054682 filed Mar. 1, 2017, claiming priority to application number EP16158644.1 filed Mar. 4, 2016, each of which are incorporated herein by reference in its entirety.

SEQUENCE LISTING

The instant application contains a Sequence Listing which has been filed electronically in ASCII format and is hereby incorporated by reference in its entirety. Said ASCII copy, created on Oct. 8, 2019, is named P33401-US_SL.txt and is 694 bytes in size.

The present invention relates to organic compounds useful for therapy or prophylaxis in a mammal, and in particular to serine protease HtrA1 inhibitors for the treatment or prophylaxis of HtrA1-mediated ocular diseases, such as wet or dry age-related macular degeneration, geographic atrophy, diabetic retinopathy, retinopathy of prematurity and polypoidal choroidal vasculopathy.

The present invention provides novel compounds of formula (I)

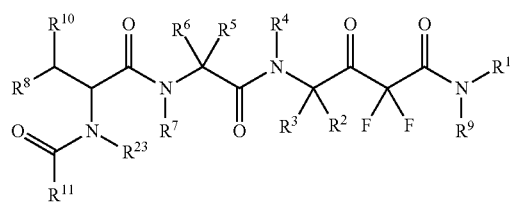

(I)

wherein $R^1$ is selected from
i) $C_{1-6}$-alkyl,
ii) $C_{3-8}$-cycloalkyl substituted with $R^{24}$, $R^{25}$ and $R^{26}$,
iii) halo-$C_{1-6}$-alkyl,
iv) heterocycloalkyl-$C_{1-6}$-alkyl substituted with $R^{24}$, $R^{25}$ and $R^{26}$,
v) aryl-$C_{1-6}$-alkyl substituted with $R^{24}$, $R^{25}$ and $R^{26}$, and
vi) heteroaryl-$C_{1-6}$-alkyl substituted with $R^{24}$, $R^{25}$ and $R^{26}$;

$R^2$, $R^3$, $R^4$, $R^6$, $R^7$, $R^9$, $R^{10}$ and $R^{23}$ are independently selected from
i) H,
ii) $C_{1-6}$-alkyl, and
iii) $C_{3-8}$-cycloalkyl;

$R^5$ is selected from
i) aryl substituted with $R^{12}$, $R^{13}$ and $R^{14}$,
ii) aryl-$C_{1-6}$-alkyl substituted with $R^{12}$, $R^{13}$ and $R^{14}$,
iii) heteroaryl substituted with $R^{12}$, $R^{13}$ and $R^{14}$, and
iv) heteroaryl-$C_{1-6}$-alkyl substituted with $R^{12}$, $R^{13}$ and $R^{14}$;

$R^8$ is selected from
i) H,
ii) hydroxy,
iii) amino-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
iv) aminocarbonyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
v) aminocarbonyl-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein arylcarbonyl and heteroarylcarbonyl are substituted with $R^{15}$, $R^{16}$ and $R^{17}$,
vi) carboxy,
vii) carboxy-$C_{1-6}$-alkyl,
viii) $C_{1-6}$-alkoxy,
ix) $C_{1-6}$-haloalkoxy,
x) $C_{1-6}$-alkoxycarbonyl,
xi) $C_{1-6}$-alkoxycarbonyl-$C_{1-6}$-alkyl,
xii) $C_{3-8}$-cycloalkyl,
xiii) aryl substituted with $R^{15}$, $R^{16}$ and $R^{17}$,
xiv) aryl-$C_{1-6}$-alkyl substituted with $R^{15}$, $R^{16}$ and $R^{17}$,
xv) aryl-$C_{1-6}$-alkoxy substituted with $R^{15}$, $R^{16}$ and $R^{17}$,
xvi) heteroaryl substituted with $R^{15}$, $R^{16}$ and $R^{17}$,
xvii) heteroaryl-$C_{1-6}$-alkyl substituted with $R^{15}$, $R^{16}$ and $R^{17}$, and
xviii) heteroaryl-$C_{1-6}$-alkoxy substituted with $R^{15}$, $R^{16}$ and $R^{17}$
xix) heterocycloalkyl substituted with $R^{15}$, $R^{16}$ and $R^{17}$,
xx) heterocycloalkyl-$C_{1-6}$-alkyl substituted with $R^{15}$, $R^{16}$ and $R^{17}$, and
xxi) heterocycloalkyl-$C_{1-6}$-alkoxy substituted with $R^{15}$, $R^{16}$ and $R^{17}$;

$R^{11}$ is selected from
i) amino-$C_{1-6}$-alkyl substituted on the nitrogen atom by $R^{21}$ and $R^{22}$,
ii) $C_{3-8}$-cycloalkyl substituted with $R^{18}$, $R^{19}$ and $R^{20}$,
iii) $C_{3-8}$-cycloalkyl-$C_{1-6}$-alkyl substituted with $R^{18}$, $R^{19}$ and $R^{20}$,
iv) $C_{3-8}$-cycloalkyl(halo)-$C_{1-6}$-alkyl substituted with $R^{18}$, $R^{19}$ and $R^{20}$,
v) aryl substituted with $R^{18}$, $R^{19}$ and $R^{20}$,
vi) aryl-$C_{1-6}$-alkyl substituted with $R^{18}$, $R^{19}$ and $R^{20}$,
vii) aryl-$C_{3-8}$-cycloalkyl substituted with $R^{18}$, $R^{19}$ and $R^{20}$,
viii) aryl-heterocycloalkyl substituted with $R^{18}$, $R^{19}$ and $R^{20}$,
ix) aryl(halo)-$C_{1-6}$-alkyl substituted with $R^{18}$, $R^{19}$ and $R^{20}$,
x) aryl(halo)-$C_{3-8}$-cycloalkyl substituted with $R^{18}$, $R^{19}$ and $R^{20}$,
xi) aryl(halo)-heterocycloalkyl substituted with $R^{18}$, $R^{19}$ and $R^{20}$,
xii) aryloxy-$C_{1-6}$-alkyl substituted with $R^{18}$, $R^{19}$ and $R^{20}$,
xiii) aryloxy-$C_{3-8}$-cycloalkyl substituted with $R^{18}$, $R^{19}$ and $R^{20}$,
xiv) aryloxy-heterocycloalkyl substituted with $R^{18}$, $R^{19}$ and $R^{20}$,
xv) aryloxy(halo)-$C_{3-8}$-cycloalkyl substituted with $R^{18}$, $R^{19}$ and $R^{20}$,
xvi) aryloxy(halo)-heterocycloalkyl substituted with $R^{18}$, $R^{19}$ and $R^{20}$,
xvii) aryloxy(halo)-$C_{1-6}$-alkyl,
xviii) heterocycloalkyl substituted with $R^{18}$, $R^{19}$ and $R^{20}$,
xix) heterocycloalkyl-$C_{1-6}$-alkyl substituted with $R^{18}$, $R^{19}$ and $R^{20}$, xx) heterocycloalkyl-$C_{3-8}$-cycloalkyl substituted with $R^{18}$, $R^{19}$ and $R^{20}$,
xxi) heterocycloalkyl(halo)-$C_{3-8}$-cycloalkyl substituted with $R^{18}$, $R^{19}$ and $R^{20}$,
xxii) heterocycloalkyl(halo)-$C_{1-6}$-alkyl substituted with $R^{18}$, $R^{19}$ and $R^{20}$,
xxiii) heteroaryl substituted with $R^{18}$, $R^{19}$ and $R^{20}$,
xxiv) heteroaryl-$C_{1-6}$-alkyl substituted with $R^{18}$, $R^{19}$ and $R^{20}$,
xxv) heteroaryl-$C_{3-8}$-cycloalkyl substituted with $R^{18}$, $R^{19}$ and $R^{20}$,
xxvi) heteroaryl(halo)-$C_{3-8}$-cycloalkyl substituted with $R^{18}$, $R^{19}$ and $R^{20}$,
xxvii) heteroaryl(halo)-$C_{1-6}$-alkyl substituted with $R^{18}$, $R^{19}$ and $R^{20}$,
xxviii) heteroaryloxy-$C_{1-6}$-alkyl substituted with $R^{18}$, $R^{19}$ and $R^{20}$,
xxix) heteroaryloxy-$C_{3-8}$-cycloalkyl substituted with $R^{18}$, $R^{19}$ and $R^{20}$,
xxx) heteroaryloxy(halo)-$C_{3-8}$-cycloalkyl substituted with $R^{18}$, $R^{19}$ and $R^{20}$, and
xxxi) heteroaryloxy(halo)-$C_{1-6}$-alkyl substituted with $R^{18}$, $R^{19}$ and $R^{20}$;
$R^{12}$, $R^{13}$, $R^{14}$, $R^{15}$, $R^{16}$, $R^{17}$, $R^{18}$, $R^{19}$, $R^{20}$, $R^{24}$, $R^{25}$ and $R^{26}$ are independently selected from
i) H,
ii) cyano,
iii) halogen,
iv) oxo,
v) $C_{1-6}$-alkyl,
vi) amino substituted on the nitrogen atom by two substituents independently selected from H, $C_{1-6}$-alkyl, $C_{1-6}$-alkoxycarbonyl, arylcarbonyl and heteroarylcarbonyl,
vii) amino-$C_{1-6}$-alkyl substituted on the nitrogen atom by two substituents independently selected from H, $C_{1-6}$-alkyl, $C_{1-6}$-alkoxycarbonyl, arylcarbonyl and heteroarylcarbonyl,
viii) $C_{1-6}$-alkyl,
ix) halo-$C_{1-6}$-alkyl,
x) $C_{3-8}$-cycloalkyl,
xi) $C_{1-6}$-alkoxycarbonyl-$C_{1-6}$-alkyl,
xii) carboxy-$C_{1-6}$-alkyl,
xiii) $C_{1-6}$-alkoxycarbonyl-$C_{1-6}$alkylaminocarbonyl-$C_{1-6}$alkyl,
xiv) carboxy-$C_{1-6}$-alkylaminocarbonyl-$C_{1-6}$alkyl,
xv) $C_{1-6}$-alkoxy,
xvi) halo-$C_{1-6}$-alkoxy,
xvii) $C_{1-6}$-alkoxycarbonyl-$C_{1-6}$-alkoxy,
xviii) carboxy-$C_{1-6}$-alkoxy,
xix) $C_{1-6}$alkoxycarbonyl-$C_{1-6}$alkylaminocarbonyl-$C_{1-6}$alkoxy, and
xx) carboxy-$C_{1-6}$alkylaminocarbonyl-$C_{1-6}$alkoxy;
xxi) heterocycloalkyl;
$R^{21}$ and $R^{22}$ are independently selected from
i) H,
ii) $C_{1-6}$-alkoxycarbonyl,
iii) carboxy-$C_{1-6}$-alkyl,
iv) arylcarbonyl, and
v) heteroarylcarbonyl;
or pharmaceutically acceptable salts;

Inhibition of the serine protease HtrA1, which belongs to an evolutionarily conserved family of HtrA proteins, has the potential to protect and treat tissue damage caused by the degeneration of retinal or photoreceptor cells in the human eye. The pathophysiological relevance of HtrA1 in the progression of the age-related macular degeneration has been firmly established by human genetic studies where a SNP in the HtrA1 promoter region results in increased HtrA1 transcript and protein levels. Age-related macular degeneration is the leading cause of severe irreversible central vision loss and blindness in individuals over 65 years of age in developed countries. There are two forms of AMD: dry AMD and wet AMD. Wet AMD (also known as exudative AMD), is associated with pathologic posterior choroidal neovascularization subsequent to the disruption of the delimiting Bruch's membrane. Tissue edema due to the leakage from the abnormal blood vessels damages the macula and impairs vision, eventually leading to blindness. In dry AMD, drusen have been reported in the macula of the eye, the cells in the macula die for the progressive accumulation of the drusen, resulting in progressive vision loss. Dry AMD is clinically described to occur in three stages: 1) early, 2) intermediate, and 3) advanced dry AMD. Dry AMD can also progress into wet AMD during any stage of the disease. Treatment strategies for wet AMD exists and the current standard of care is Lucentis® (Genentech/Roche) and Eylea® (Regeneron), an anti-VEGF antibody and an anti-VEGF trap injected intravitreally respectively. There are no current treatments for preventing loss of vision for the dry form and for preventing local progression of dry AMD to local atrophy of the retinal tissue. As discussed above, HtrA1 risk alleles have been associated, with high statistical significance, with the AMD onsets and the protein has been reported to be present in drusen. These studies and further evidences provide relevance that HtrA1 is a fundamental factor involved in the pathophysiology and progression in AMD. This concept is further confirmed in different AMD disease models, where increased HtrA1 protein levels in the retina tissue have been shown to be responsible for the degradation of extracellular matrix (ECM) proteins like fibronectin, fibulins and aggrecan. The physiological balance between production and disintegration of the ECM components allows for both creation and maintenance of proper retina tissue architecture. Such balance has been reported to be lost in the progression of the age-related macular degeneration. In particular, the fibulins (mainly-3, -5, -6) have been reported to be important components of the Bruch's membrane in maintaining the integrity of elastic lamina and organization of the retina tissue overall. Several variants in fibulin 5 and fibulin 3 were reported to be associated with AMD. Missense mutations of the fibulin 5 gene have been associated with reduced secretion of fibulin 5. Different studies have reported that Htra1 protease activity is directed to the cleavage of the fibulins as substrates. A direct inhibition of HtrA1 protease activity is expected to provide a protection reducing degradation of extracellular matrix proteins, in particular fibulins and fibrionectin, therefore preserving the retina tissue structure. The relevance of HtrA1's role in maintenance of the physiological homeostasis of the ECM components is firmly provided by the identification of human loss-of-function mutations causing familial ischemic cerebral small-vessel disease. The molecular mechanism underlies in the deficient TGFbeta inhibition by HtrA1 resulting in increased signaling levels, which in conjunction with deficient HtrA1-mediated degradation of various extracellular matrix components determine thickening of the intima responsible for the ischemic small-vessels. Given its fundamental role in regulating intracellular signaling pathways (e.g. TGFbeta) and the regulation of ECM proteins turnover, HtrA1 has been involved in several pathologies, as ocular diseases, rheumatoid arthritis, osteoarthritis, Alzheimer's disease, and some types of cancer.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of HtrA1, particularly in the treatment or prophylaxis of wet or dry age-related macular degeneration, geographic atrophy, diabetic retinopathy, retinopathy of prematurity and polypoidal choroidal vasculopathy.

The term "amino" denotes a —NH$_2$ group.

The term "amino-$C_{1-6}$-alkyl" denotes an $C_{1-6}$-alkyl group wherein one of the hydrogen atoms of the $C_{1-6}$-alkyl group has been replaced by an amino group. Examples of amino-$C_{1-6}$-alkyl groups are aminomethyl, aminoethyl or aminopropyl. Particular examples of amino-$C_{1-6}$-alkyl is aminomethyl.

The term "aminocarbonyl" denotes a group of the formula —C(O)—R', wherein R' is an amino group.

The term "aminocarbonyl-$C_{1-6}$-alkyl" denotes an $C_{1-6}$-alkyl group wherein one of the hydrogen atoms of the $C_{1-6}$-alkyl group has been replaced by an aminocarbonyl group. Examples of aminocarbonyl-$C_{1-6}$-alkyl groups are aminocarbonylmethyl, aminocarbonylethyl or aminocarbonylpropyl The term "$C_{1-6}$-alkoxy" denotes a group of the formula —O—R', wherein R' is an $C_{1-6}$-alkyl group. Examples of $C_{1-6}$-alkoxy groups include methoxy, ethoxy, n-propoxy, isopropoxy, n-butoxy, isobutoxy and tert-butoxy. Particular example is methoxy. In the case of $R^{12}$, particular example is methoxy.

The term "$C_{1-6}$-alkoxycarbonyl" denotes a group of the formula —C(O)—R', wherein R' is a $C_{1-6}$-alkoxy group. Particular example of $C_{1-6}$-alkoxycarbonyl is a group wherein R' is tert-butoxy.

The term "$C_{1-6}$-alkoxycarbonyl-$C_{1-6}$-alkoxy" denotes an $C_{1-6}$-alkoxy group wherein one of the hydrogen atoms of the $C_{1-6}$-alkoxy group has been replaced by a $C_{1-6}$-alkoxycarbonyl group. Particular example of $C_{1-6}$-alkoxycarbonyl-$C_{1-6}$-alkoxy is a methoxy wherein one of the hydrogen atoms has been replaced by tert-butoxycarbonyl.

The term "$C_{1-6}$-alkoxycarbonyl-$C_{1-6}$-alkyl" denotes an $C_{1-6}$-alkyl group wherein one of the hydrogen atoms of the $C_{1-6}$-alkyl group has been replaced by a $C_{1-6}$-alkoxycarbonyl group. Particular example of $C_{1-6}$-alkoxycarbonyl-$C_{1-6}$-alkyl is a methyl wherein one of the hydrogen atoms has been replaced by tert-butoxycarbonyl.

The term "$C_{1-6}$alkoxycarbonyl-$C_{1-6}$alkylaminocarbonyl-$C_{1-6}$alkoxy" denotes an $C_{1-6}$-alkoxy group wherein one of the hydrogen atoms of the $C_{1-6}$-alkoxy group has been replaced by a $C_{1-6}$alkoxycarbonyl-$C_{1-6}$alkylaminocarbonyl group. Particular example is methoxy wherein one of the hydrogen atoms has been replaced by ter-butoxycarbonylmethylamino.

The term "$C_{1-6}$alkoxycarbonyl-$C_{1-6}$alkylaminocarbonyl-$C_{1-6}$alkyl" denotes an $C_{1-6}$-alkyl group wherein one of the hydrogen atoms of the $C_{1-6}$-alkyl group has been replaced by a $C_{1-6}$alkoxycarbonyl-$C_{1-6}$alkylaminocarbonyl group. Particular example is methyl wherein one of the hydrogen atoms has been replaced by ter-butoxycarbonylmethylaminocarbonyl.

The term "$C_{1-6}$alkoxycarbonyl-$C_{1-6}$alkylaminocarbonyl" denotes a group of the formula —C(O)—R', wherein R' is a $C_{1-6}$alkoxycarbonyl-$C_{1-6}$alkylamino group. Particular example is a group wherein R' is ter-butoxycarbonylmethylamino.

The term "$C_{1-6}$-alkoxycarbonyl-$C_{1-6}$-alkylamino" denotes a group of the formula —NH—R', wherein R' is an $C_{1-6}$-alkoxycarbonyl-$C_{1-6}$-alkyl group. Particular example is a group wherein R' is ter-butoxycarbonylmethyl.

The term "$C_{1-6}$-alkoxycarbonyl-$C_{1-6}$-alkyl" denotes an $C_{1-6}$-alkyl group wherein one of the hydrogen atoms of the $C_{1-6}$-alkyl group has been replaced by an $C_{1-6}$-alkoxycarbonyl group. Particular example is a methyl wherein one of the hydrogen atoms of has been replaced by a ter-butoxycarbonyl.

The term "$C_{1-6}$-alkyl" denotes a monovalent linear or branched saturated hydrocarbon group of 1 to 6 carbon atoms. Examples of $C_{1-6}$-alkyl include methyl, ethyl, propyl, isopropyl, n-butyl, iso-butyl, sec-butyl, tert-butyl and pentyl. Particular $C_{1-6}$-alkyl groups are methyl and isopropyl. In the case of $R^2$, particular example is isopropyl.

The term "aryl" denotes a monovalent aromatic carbocyclic mono- or bicyclic ring system comprising 6 to 10 carbon ring atoms. Examples of aryl group include phenyl and naphthyl. Particular aryl group is phenyl.

The term "aryl(halo)-$C_{1-6}$-alkyl" denotes a halo-$C_{1-6}$-alkyl group wherein one of the hydrogen atoms of the halo-$C_{1-6}$-alkyl group has been replaced by an aryl group. Particular examples are groups wherein the aryl group is phenyl. Further particular example is phenyl-difluoromethyl.

The term "aryl-$C_{1-6}$-alkyl" denotes an —$C_{1-6}$-alkyl group wherein one of the hydrogen atoms of the $C_{1-6}$-alkyl group has been replaced by an aryl group. Particular aryl-$C_{1-6}$-alkyl group is phenyl-$C_{1-6}$-alkyl. Further particular examples of aryl-$C_{1-6}$-alkyl are phenylmethyl and phenylpropyl. Furthermore particular examples of aryl-$C_{1-6}$-alkyl is phenylmethyl.

The term "aryl-$C_{1-6}$-alkoxy" denotes an —$C_{1-6}$-alkoxy group wherein one of the hydrogen atoms of the —$C_{1-6}$-alkoxy group has been replaced by an aryl group. Particular examples are groups wherein the aryl group is phenyl. Particular aryl-$C_{1-6}$-alkoxy group is phenylmethoxy.

The term "aryloxy" denotes a group of the formula —O—R', wherein R' is an aryl group. Particular examples of aryloxy group are groups wherein R' is phenyl.

The term "aryloxy-$C_{1-6}$-alkyl" denotes an $C_{1-6}$-alkyl group wherein one of the hydrogen atoms of the $C_{1-6}$-alkyl group has been replaced by an aryloxy group. Particular examples are groups wherein the aryloxy group is phenoxy. Further particular example of aryloxy-$C_{1-6}$-alkyl is phenoxyalkyl. Further particular example is phenoxymethyl.

The term "aryloxy(halo)-$C_{1-6}$-alkyl" denotes a halo-$C_{1-6}$-alkyl group wherein one of the hydrogen atoms of the halo-$C_{1-6}$-alkyl group has been replaced by an aryloxy group. Particular examples are groups wherein the aryloxy group is phenoxy.

The term "arylcarbonyl" denotes a group of the formula —C(O)—R', wherein R' is an aryl group. Particular example is a group wherein R' is phenyl.

The term "aryl(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by an aryl group. Particular examples are groups wherein the aryl group is phenyl. Further particular example is phenyl-difluorocyclopropyl.

The term "aryl-$C_{3-8}$-cycloalkyl" denotes a halo-$C_{3-8}$-cycloalkyl group wherein one of the hydrogen atoms of the $C_{3-8}$-cycloalkyl group has been replaced by an aryl group.

Particular examples are groups wherein the aryl group is phenyl. Further particular example is phenylcyclopropyl.

The term "aryloxy-$C_{3-8}$-cycloalkyl" denotes a $C_{3-8}$-cycloalkyl group wherein one of the hydrogen atoms of the $C_{3-8}$-cycloalkyl group has been replaced by an aryloxy group. Particular examples are groups wherein the aryloxy group is phenoxy. Further particular example is phenyl-difluorocyclopropyl.

The term "aryloxy(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by an aryloxy group. Particular examples are groups wherein the aryloxy group is phenoxy. Further particular example is phenoxy-difluorocyclopropyl.

The term "aryloxy-$C_{3-8}$-cycloalkyl" denotes a $C_{3-8}$-cycloalkyl group wherein one of the hydrogen atoms of the $C_{3-8}$-cycloalkyl group has been replaced by an aryloxy group. Particular examples are groups wherein the aryloxy group is phenoxy. Further particular example is phenoxy-cyclopropyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "carboxy" denotes a —COOH group.

The term "carboxy-$C_{1-6}$-alkoxy" denotes an $C_{1-6}$-alkoxy group wherein one of the hydrogen atoms of the $C_{1-6}$-alkoxy group has been replaced by a carboxy group. Particular example is carboxymethoxy.

The term "carboxy-$C_{1-6}$-alkyl" denotes an $C_{1-6}$-alkyl group wherein one of the hydrogen atoms of the $C_{1-6}$-alkyl group has been replaced by a carboxy group. Particular example is carboxymethyl.

The term "carboxy-$C_{1-6}$-alkylaminocarbonyl-$C_{1-6}$-alkoxy" denotes an $C_{1-6}$-alkoxy group wherein one of the hydrogen atoms of the $C_{1-6}$-alkoxy group has been replaced by a carboxy-$C_{1-6}$-alkylaminocarbonyl group. Particular example is carboxymethylaminocarbonylmethoxy.

The term "carboxy-$C_{1-6}$alkylaminocarbonyl-$C_{1-6}$alkyl" denotes an $C_{1-6}$-alkyl group wherein one of the hydrogen atoms of the $C_{1-6}$-alkyl group has been replaced by a carboxy-$C_{1-6}$alkylaminocarbonyl group. Particular example is carboxymethylaminocarbonylmethyl.

The term "carboxy-$C_{1-6}$alkylaminocarbonyl group" denotes a group of the formula —C(O)—R', wherein R' is a carboxy-$C_{1-6}$alkylamino group. Particular example is carboxymethylamino.

The term "carboxy-$C_{1-6}$alkylamino" denotes a group of the formula —NH—R', wherein R' is a carboxy-$C_{1-6}$alkyl group. Particular example is a group wherein R' is carboxymethyl.

The term "cyano" denotes a —C≡N group.

The term "$C_{3-8}$-cycloalkyl" denotes a monovalent saturated monocyclic hydrocarbon group of 3 to 8 ring carbon atoms. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl. Particular monocyclic cycloalkyl groups are cyclopropyl, cyclobutanyl, cyclopentyl and cyclohexyl. More particular monocyclic cycloalkyl group is cyclopropyl.

The term "$C_{3-8}$-cycloalkyl(halo)-$C_{1-6}$-alkyl" denotes a halo-$C_{1-6}$-alkyl group wherein one of the hydrogen atoms of the halo-$C_{1-6}$-alkyl group has been replaced by an $C_{3-8}$-cycloalkyl group.

The term "$C_{3-8}$-cycloalkyl-$C_{1-6}$-alkyl" denotes an —$C_{1-6}$-alkyl group wherein one of the hydrogen atoms of the $C_{1-6}$-alkyl group has been replaced by an $C_{3-8}$-cycloalkyl group. Examples of cycloalkylalkyl include cyclopropylmethyl, cyclopropylethyl, cyclopropylbutyl, cyclobutylpropyl, 2-cyclopropylbutyl, cyclopentylbutyl, cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Particular examples of cycloalkylalkyl are cyclohexylmethyl, cyclohexylethyl, bicyclo[4.1.0]heptanylmethyl, bicyclo[4.1.0]heptanylethyl, bicyclo[2.2.2]octanylmethyl and bicyclo[2.2.2]octanylethyl. Further particular examples cycloalkylalkyl is cyclohexylethyl.

The term "halo-$C_{1-6}$-alkoxy" denotes an $C_{1-6}$-alkoxy group wherein at least one of the hydrogen atoms of the $C_{1-6}$-alkoxy group has been replaced by same or different halogen atoms. The term "perhaloalkoxy" denotes an alkoxy group where all hydrogen atoms of the alkoxy group have been replaced by the same or different halogen atoms. Examples of haloalkoxy include fluoromethoxy, difluoromethoxy, trifluoromethoxy, trifluoroethoxy, trifluoromethylethoxy, trifluorodimethylethoxy and pentafluoroethoxy. Particular haloalkoxy groups is difluoromethoxy.

The term "halo-$C_{1-6}$-alkyl" denotes an $C_{1-6}$-alkyl group wherein at least one of the hydrogen atoms of the $C_{1-6}$-alkyl group has been replaced by the same or different halogen atoms. The term "perhaloalkyl" denotes an alkyl group where all hydrogen atoms of the alkyl group have been replaced by the same or different halogen atoms. Examples of haloalkyl include fluoromethyl, difluoromethyl, trifluoromethyl, trifluoroethyl, trifluoromethylethyl and pentafluoroethyl. Particular haloalkyl group is trifluoroethyl.

The term "halo-$C_{3-8}$-cycloalkyl" denotes an $C_{3-8}$-cycloalkyl group wherein at least one of the hydrogen atoms of the $C_{3-8}$-cycloalkyl group has been replaced by the same or different halogen atoms.

The term "halogen" and "halo" are used interchangeably herein and denote fluoro, chloro, bromo or iodo. Particular halogen is chloro.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl group include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, and benzothiophenyl. Particular heteroaryl groups are pyrazinyl, pyridinyl, pyrimidinyl and thiophenyl. In the case of substituent $R^{11}$, particular heteroaryl groups are pyrazinyl, pyridinyl, pyrimidinyl and thiophenyl.

The term "heteroaryl(halo)-$C_{1-6}$-alkyl" denotes a halo-$C_{1-6}$-alkyl group wherein one of the hydrogen atoms of the halo-$C_{1-6}$-alkyl group has been replaced by a heteroaryl group.

The term "heteroaryl-$C_{1-6}$-alkyl" denotes an $C_{1-6}$-alkyl group wherein one of the hydrogen atoms of the $C_{1-6}$-alkyl group has been replaced by a heteroaryl group.

The term "heteroaryl-$C_{1-6}$-alkoxy" denotes an $C_{1-6}$-alkoxy group wherein one of the hydrogen atoms of the $C_{1-6}$-alkoxy group has been replaced by a heteroaryl group.

The term "heteroaryloxy" denotes a group of the formula —O—R', wherein R' is a heteroaryl group.

The term "heteroaryloxy-$C_{1-6}$-alkyl" denotes an $C_{1-6}$-alkyl group wherein one of the hydrogen atoms of the $C_{1-6}$-alkyl group has been replaced by an heteroaryloxy group.

The term "heteroaryloxy(halo)-$C_{1-6}$-alkyl" denotes a halo-$C_{1-6}$-alkyl group wherein one of the hydrogen atoms of the halo-$C_{1-6}$-alkyl group has been replaced by a heteroaryloxy group.

The term "heteroarylcarbonyl" denotes a group of the formula —C(O)—R', wherein R' is a heteroaryl group. Particular heteroarylcarrbonyl is a group wherein R' is pyridinyl.

The term "heteroaryl(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heteroaryl group.

The term "heteroaryl-$C_{3-8}$-cycloalkyl" denotes a halo-$C_{3-8}$-cycloalkyl group wherein one of the hydrogen atoms of the $C_{3-8}$-cycloalkyl group has been replaced by a heteroaryl group.

The term "heteroaryloxy-$C_{3-8}$-cycloalkyl" denotes a $C_{3-8}$-cycloalkyl group wherein one of the hydrogen atoms of the $C_{3-8}$-cycloalkyl group has been replaced by a heteroaryloxy group.

The term "heteroaryloxy(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heteroaryloxy group.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having two ring atoms in common, i.e. the bridge separating the two rings is either a single bond or a chain of one or two ring atoms. Examples for monocyclic saturated heterocycloalkyl are 4,5-dihydro-oxazolyl, oxetanyl, azetidinyl, pyrrolidinyl, 2-oxo-pyrrolidin-3-yl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. In the case of $R^{18}$, particular heterocycloalkyl is morpholinyl.

The term "heterocycloalkyl-$C_{1-6}$-alkyl" denotes an $C_{1-6}$-alkyl group wherein one of the hydrogen atoms of the $C_{1-6}$-alkyl group has been replaced by a heterocycloalkyl group. In the case of $R^1$, particular heterocycloalkyl-$C_{1-6}$-alkyl is morpholinoethyl.

The term "heterocycloalkyl-$C_{1-6}$-alkoxy" denotes an $C_{1-6}$-alkoxy group wherein one of the hydrogen atoms of the $C_{1-6}$-alkoxy group has been replaced by a heterocycloalkyl group.

The term "heterocycloalkyl(halo)-$C_{1-6}$-alkyl" denotes a halo-$C_{1-6}$-alkyl group wherein one of the hydrogen atoms of the halo-$C_{1-6}$-alkyl group has been replaced by a heterocycloalkyl group.

The term "heterocycloalkyl(halo)-$C_{3-8}$-cycloalkyl" denotes a halo-$C_{3-8}$-cycloalkyl group wherein one of the hydrogen atoms of the halo-$C_{3-8}$-cycloalkyl group has been replaced by a heterocycloalkyl group.

The term "hydroxy" denotes a —OH group.

The term "oxo" denotes a =O group.

The term "phenoxy" denotes a group of the formula —O—R', wherein R' is a phenyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

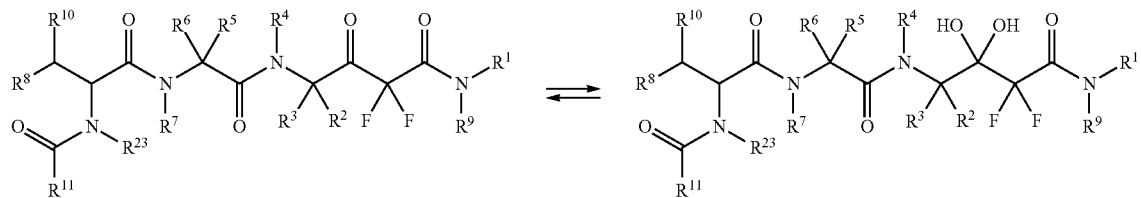

Depending on the individual compound and the conditions it has been exposed, the $CF_3$-ketone moieties in compounds I exist in part, mainly or totally in form of its hydrate. Thus, any description of a $CF_3$-ketone moiety always describes both ketone and hydrate form.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

Another embodiment of the present invention are compounds according to formula (I) as described herein, wherein
$R^1$ is halo-$C_{1-6}$-alkyl;
$R^2$ is selected from
  i) $C_{1-6}$-alkyl, and
  ii) $C_{3-8}$-cycloalkyl;
$R^3$, $R^4$, $R^6$, $R^7$, $R^9$, $R^{10}$ and $R^{23}$ are H;
$R^5$ is phenyl substituted with $R^{12}$, $R^{13}$ and $R^{14}$;
$R^8$ is selected from
  i) H,
  ii) hydroxy,
  iii) phenyl substituted with $R^{15}$, $R^{16}$ and $R^{17}$;
$R^{11}$ is selected from
  i) amino-$C_{1-6}$-alkyl substituted on the nitrogen atom by $R^{21}$ and $R^{22}$,
  ii) phenyl substituted with $R^{18}$, $R^{19}$ and $R^{20}$,
  iii) phenyl-$C_{1-6}$-alkyl substituted with $R^{18}$, $R^{19}$ and $R^{20}$,
  iv) phenyl-$C_{3-8}$-cycloalkyl substituted with $R^{18}$, $R^{19}$ and $R^{20}$,
  v) phenyl(halo)-$C_{1-6}$-alkyl substituted with $R^{18}$, $R^{19}$ and $R^{20}$,
  vi) heteroaryl substituted with $R^{18}$, $R^{19}$ and $R^{20}$, wherein heteroaryl is selected from pyrazinyl, pyridinyl, pyrimidinyl and thiophenyl;
$R^{12}$ is selected from
  i) H, and
  ii) $C_{1-6}$-alkoxy;
$R^{13}$, $R^{14}$, $R^{17}$ and $R^{20}$ are H;

$R^{15}$ is selected from
  i) $C_{1-6}$-alkyl,
  ii) cyano,
  iii) halogen, and
  iv) carboxy-$C_{1-6}$-alkoxy;
$R^{16}$ is selected from
  i) H, and
  ii) halogen;
$R^{18}$ is selected from
  i) H,
  ii) halogen,
  iii) halo-$C_{1-6}$-alkoxy,
  iv) cyano,
  v) amino substituted on the nitrogen atom by two $C_{1-6}$-alkyl,
  vi) $C_{1-6}$-alkoxycarbonyl-$C_{1-6}$-alkoxy,
  vii) carboxy-$C_{1-6}$-alkoxy, and
  viii) morpholinyl;
$R^{19}$ is selected from
  i) H and
  ii) halogen;
$R^{21}$ is pyridinylcarbonyl;
$R^{22}$ is H;
or pharmaceutically acceptable salts.

Another particular embodiment of the present invention are compounds according to formula (I) as described herein, wherein $R^1$ is halo-$C_{1-6}$-alkyl.

A further particular embodiment of the present invention are compounds according to formula (I) as described herein, wherein $R^1$ is trifluoroethyl.

Another particular embodiment of the present invention are compounds according to formula (I) as described herein, wherein $R^2$ is $C_{1-6}$-alkyl.

Also a furthermore particular embodiment of the present invention are compounds according to formula (I) as described herein, wherein $R^2$ is isopropyl.

A particular embodiment of the present invention are compounds according to formula (I) as described herein, wherein $R^3$ is H.

A particular embodiment of the present invention are compounds according to formula (I) as described herein, wherein $R^4$ is H.

A particular embodiment of the present invention are compounds according to formula (I) as described herein, wherein $R^6$ is H.

A particular embodiment of the present invention are compounds according to formula (I) as described herein, wherein $R^7$ is H.

A particular embodiment of the present invention are compounds according to formula (I) as described herein, wherein $R^9$ is H.

A particular embodiment of the present invention are compounds according to formula (I) as described herein, wherein $R^{10}$ is H.

A particular embodiment of the present invention are compounds according to formula (I) as described herein, wherein $R^{23}$ is H.

A further particular embodiment of the present invention are compounds according to formula (I) as described herein, wherein $R^3$, $R^4$, $R^6$, $R^7$, $R^9$, $R^{10}$ and $R^{23}$ are H.

In a further particular embodiment of the present invention are compounds according to formula (I) as described herein, wherein $R^5$ is phenyl-$C_{1-6}$-alkyl substituted with $R^{12}$, $R^{13}$ and $R^{14}$.

A more particular embodiment of the present invention are compounds according to formula (I) as described herein, wherein $R^5$ is phenyl substituted with one $C_{1-6}$-alkoxy.

A particular embodiment of the present invention are compounds according to formula (I) as described herein, wherein $R^8$ is selected from
i) H,
ii) hydroxy, and
iii) phenyl substituted with $R^{15}$, $R^{16}$ and $R^{17}$.

A further particular embodiment of the present invention are compounds according to formula (I) as described herein, wherein $R^8$ is selected from
i) hydroxy, and
ii) phenyl substituted with $R^{15}$, $R^{16}$ and $R^{17}$.

A more particular embodiment of the present invention are compounds according to formula (I) as described herein, wherein $R^8$ is phenyl substituted with $R^{15}$, $R^{16}$ and $R^{17}$.

Another embodiment of the present invention are compounds according to formula (I) as described herein, wherein $R^{11}$ is selected from
i) amino-$C_{1-6}$-alkyl substituted on the nitrogen atom by $R^{21}$ and $R^{22}$,
ii) phenyl substituted with $R^{18}$, $R^{19}$ and $R^{20}$,
iii) phenyl-$C_{1-6}$-alkyl substituted with $R^{18}$, $R^{19}$ and $R^{20}$,
iv) phenyl-$C_{3-8}$-cycloalkyl substituted with $R^{18}$, $R^{19}$ and $R^{20}$,
v) phenyl(halo)-$C_{1-6}$-alkyl substituted with $R^{18}$, $R^{19}$ and $R^{20}$,
vi) heteroaryl substituted with $R^{18}$, $R^{19}$ and $R^{20}$, wherein heteroaryl is selected from pyrazinyl, pyridinyl, pyrimidinyl and thiophenyl.

Also a particular embodiment of the present invention are compounds according to formula (I) as described herein, wherein $R^{11}$ is selected from
i) phenyl substituted with $R^{18}$, $R^{19}$ and $R^{20}$,
ii) phenyl-$C_{1-6}$-alkyl substituted with $R^{18}$, $R^{19}$ and $R^{20}$,
iii) phenyl(halo)-$C_{1-6}$-alkyl substituted with $R^{18}$, $R^{19}$ and $R^{20}$,
iv) heteroaryl substituted with $R^{18}$, $R^{19}$ and $R^{20}$, wherein heteroaryl is selected from pyridinyl and thiophenyl.

A more particular embodiment of the present invention are compounds according to formula (I) as described herein, wherein $R^{11}$ is phenyl substituted with $R^{18}$, $R^{19}$ and $R^{20}$.

Another embodiment of the present invention are compounds according to formula (I) as described herein, wherein $R^{12}$ is selected from
i) H, and
ii) $C_{1-6}$-alkoxy.

Another particular embodiment of the present invention are compounds according to formula (I) as described herein, wherein $R^{12}$ is $C_{1-6}$-alkoxy.

Another embodiment of the present invention are compounds according to formula (I) as described herein, wherein $R^{13}$, $R^{14}$, $R^{17}$ and $R^{20}$ are H.

Also an embodiment of the present invention are compounds according to formula (I) as described herein, wherein $R^{15}$ is selected from
i) $C_{1-6}$-alkyl,
ii) cyano,
iii) halogen, and
iv) carboxy-$C_{1-6}$-alkoxy.

Another particular embodiment of the present invention are compounds according to formula (I) as described herein, wherein $R^{15}$ is selected from
i) cyano, and
ii) halogen.

A further particular embodiment of the present invention are compounds according to formula (I) as described herein, wherein $R^{15}$ is halogen.

Another embodiment of the present invention are compounds according to formula (I) as described herein, wherein $R^{16}$ is selected from
i) H, and
ii) halogen.

Another particular embodiment of the present invention are compounds according to formula (I) as described herein, wherein $R^{16}$ is H.

Another embodiment of the present invention are compounds according to formula (I) as described herein, wherein $R^{18}$ is selected from
i) H,
ii) halogen,
iii) halo-$C_{1-6}$-alkoxy,
iv) cyano,
v) amino substituted on the nitrogen atom by two $C_{1-6}$-alkyl,
vi) $C_{1-6}$-alkoxycarbonyl-$C_{1-6}$-alkoxy,
vii) carboxy-$C_{1-6}$-alkoxy, and
viii) morpholinyl.

Another particular embodiment of the present invention are compounds according to formula (I) as described herein, wherein $R^{18}$ is selected from
i) H,
ii) cyano, and
iii) halogen.

Another more particular embodiment of the present invention are compounds according to formula (I) as described herein, wherein $R^{18}$ is halogen.

Another particular embodiment of the present invention are compounds according to formula (I) as described herein, wherein $R^{19}$ is selected from
i) H, and
ii) halogen.

Another more particular embodiment of the present invention are compounds according to formula (I) as described herein, wherein $R^{19}$ is H.

Another embodiment of the present invention are compounds according to formula (I) as described herein, wherein $R^{21}$ is pyridinylcarbonyl.

Another embodiment of the present invention are compounds according to formula (I) as described herein, wherein $R^{22}$ is H.

A more particular embodiment of the present invention are compounds according to formula (I) as described herein, wherein
$R^1$ is halo-$C_{1-6}$-alkyl
$R^2$ is $C_{1-6}$-alkyl;
$R^3$, $R^4$, $R^6$, $R^7$, $R^9$, $R^{10}$ and $R^{23}$ are H;
$R^5$ is phenyl substituted with one $C_{1-6}$-alkoxy;
$R^8$ is phenyl substituted with $R^{15}$, $R^{16}$ and $R^{17}$;
$R^{11}$ is phenyl substituted with $R^{18}$, $R^{19}$ and $R^{20}$;
$R^{15}$ is selected from
i) cyano, and
ii) halogen;

$R^{16}$ is selected from
i) H, and
ii) halogen;
$R^{17}$ and $R^{20}$ are H;
$R^{18}$ is selected from
i) H,
i) cyano, and
ii) halogen;
$R^{19}$ is selected from
i) H and
ii) halogen;
or pharmaceutically acceptable salts.

Particular examples of compounds of formula (I) as described herein are selected from N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyridine-4-carboxamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyridine-2-carboxamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyrazine-2-carboxamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyrimidine-5-carboxamide;

N-[(2S)-3-(3,4-dichlorophenyl)-1-[[(1S)-2-[[(3S)-5,5-difluoro-2-methyl-4,6-dioxo-6-(2,2,2- trifluoroethylamino)hexan-3-yl]amino]-1-(4-methoxyphenyl)-2-oxoethyl]amino]-1-oxopropan-2-yl]pyridine-2-carboxamide;

N-[(2S)-3-(3,4-dichlorophenyl)-1-[[(1S)-2-[[(3S)-5,5-difluoro-2-methyl-4,6-dioxo-6-(2,2,2- trifluoroethylamino)hexan-3-yl]amino]-2-oxo-1-phenylethyl]amino]-1-oxopropan-2-yl]pyridine-2-carboxamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-5-(difluoromethoxy)pyridine-2-carboxamide;

N-[(2S)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-3-(3-methylphenyl)-1-oxopropan-2-yl]pyridine-2-carboxamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]-5-(difluoromethoxy)pyridine-2-carboxamide;

N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-methylphenyl)-1-oxopropan-2-yl]pyridine-2-carboxamide;

"N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-5-morpholin-4-ylpyridine-2-carboxamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-5-(dimethylamino)pyridine-2-carboxamide;

N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;

N-[3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]benzamide;

N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[(2S)-3-(3-chloro-4-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;

N-[2-[[(2S)-3-(3-chlorophenyl)-1-[[(1S)-2-[[(3S)-5,5-difluoro-2-methyl-4,6-dioxo-6-(2,2,2- trifluoroethylamino)hexan-3-yl]amino]-1-(4-methoxyphenyl)-2-oxoethyl]amino]-1-oxopropan-2-yl]amino]-2-oxoethyl]pyridine-2-carboxamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[2-[[(2S)-3-(3-cyanophenyl)-1-[[(1S)-2-[[(3S)-5,5-difluoro-2-methyl-4,6-dioxo-6-(2,2,2- trifluoroethylamino)hexan-3-yl]amino]-1-(4-methoxyphenyl)-2-oxoethyl]amino]-1-oxopropan-2-yl]amino]-2-oxoethyl]pyridine-2-carboxamide;

3-chloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-hydroxy-1-oxopropan-2-yl]benzamide;

1-(3-chlorophenyl)-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-hydroxy-1-oxopropan-2-yl]cyclopropane-1-carboxamide;

1-(3-chlorophenyl)-N-[(2S,3R)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-hydroxy-1-oxobutan-2-yl]cyclopropane-1-carboxamide;

N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

1-(3-chlorophenyl)-N-[(2S)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]cyclopropane-1-carboxamide;

1-(3-chlorophenyl)-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]cyclopropane-1-carboxamide;

2,5-dichloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

3-chloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[(2R)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;

3-chloro-N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

5-chloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]thiophene-2-carboxamide;

5-chloro-N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]thiophene-2-carboxamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-3-cyanobenzamide;

2,5-dichloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

tert-butyl 2-[4-[[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]carbamoyl]phenoxy]acetate;

2-[4-[[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]carbamoyl]phenoxy]acetic acid;

2-[4-[(2S)-2-[[2-(3-chlorophenyl)-2,2-difluoroacetyl]amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetic acid;

2-[4-[(2S)-2-[(3-chlorobenzoyl)amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetic acid;

(4S)-4-[[(2S)-2-[[(2S)-3-(3-chlorophenyl)-2-[[2-(3-chlorophenyl)-2,2-difluoroacetyl]amino]propanoyl]amino]-2-(4-methoxyphenyl)acetyl]amino]-2,2-difluoro-5-methyl-3-oxo-N-(2,2,2-trifluoroethyl)hexanamide;

3-chloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide;

N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]pyridine-2-carboxamide;

2,5-dichloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide;

(4S)-4-[[(2S)-2-[[(2S)-3-(3-chlorophenyl)-2-[[2-(3-chlorophenyl)acetyl]amino]propanoyl]amino]-2-(4-methoxyphenyl)acetyl]amino]-2,2-difluoro-5-methyl-3-oxo-N-(2,2,2-trifluoroethyl)hexanamide;

(4S)-4-[[(2S)-2-[[(2S)-2-[[2-(3-chlorophenyl)-2,2-difluoroacetyl]amino]-3-(3-fluorophenyl)propanoyl]amino]-2-(4-methoxyphenyl)acetyl]amino]-2,2-difluoro-5-methyl-3-oxo-N-(2,2,2-trifluoroethyl)hexanamide;

N-[(2S)-3-(3-chlorophenyl)-1-[[(1S)-2-[[(1S)-1-cyclobutyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide;

3-chloro-N-[(2S)-3-(4-chloro-3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[(2S)-3-(3-cyanophenyl)-1-[[(1S)-2-[[(1S)-1-cyclobutyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide;

N-[(2S)-3-(3-cyanophenyl)-1-[[(1S)-2-[[(1S)-1-cyclobutyl-3,3-difluoro-2,4-dioxo-4-(2,2,2-trifluoroethylamino)butyl]amino]-1-(4-methoxyphenyl)-2-oxoethyl]amino]-1-oxopropan-2-yl]benzamide;

(4S)-4-[[(2S)-2-[[(2S)-2-[[2-(3-chlorophenyl)-2,2-difluoroacetyl]amino]propanoyl]amino]-2-(4-methoxyphenyl)acetyl]amino]-2,2-difluoro-5-methyl-3-oxo-N-(2,2,2-trifluoroethyl)hexanamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-3-fluorobenzamide;

3,5-dichloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-1-phenylcyclopropane-1-carboxamide;

1-(3-chlorophenyl)-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]cyclopropane-1-carboxamide;

3-cyano-N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

(4S)-4-[[(2S)-2-[[(2S)-2-[[2-(3-chlorophenyl)-2,2-difluoroacetyl]amino]-3-(3-cyanophenyl)propanoyl]amino]-2-(4-methoxyphenyl)acetyl]amino]-2,2-difluoro-5-methyl-3-oxo-N-(2,2,2-trifluoroethyl)hexanamide;

3-cyano-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide;

N-[(2S)-3-(3-chlorophenyl)-1-[[(1S)-2-[[(1S)-1-cyclopropyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide;

N-[(2S)-3-(3-cyanophenyl)-1-[[(1S)-2-[[(1S)-1-cyclopropyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide;

(4S)-4-[[(2S)-2-[[(2S)-2-[[2-(3-chlorophenyl)-2,2-difluoro-acetyl]amino]-3-hydroxypropanoyl]amino]-2-(4-methoxyphenyl)acetyl]amino]-2,2-difluoro-5-methyl-3-oxo-N-(2,2,2-trifluoroethyl)hexanamide;
and pharmaceutically acceptable salts thereof.

Also particular examples of compounds of formula (I) as described herein are selected from
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;
N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;
N-[3-(3-chiorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;
N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;
5-chloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]thiophene-2-carboxamide;
5-chloro-N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]thiophene-2-carboxamide;
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-3-cyanobenzamide;
2,5-dichloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;
3-chloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide;
(4S)-4-[[(2S)-2-[[(2S)-3-(3-chlorophenyl)-2-[[2-(3-chlorophenyl)acetyl]amino]propanoyl]amino]-2-(4-methoxyphenyl)acetyl]amino]-2,2-difluoro-5-methyl-3-oxo-N-(2,2,2-trifluoroethyl)hexanamide;
3-chloro-N-[(2S)-3-(4-chloro-3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-3-fluorobenzamide;
3-cyano-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide;
(4S)-4-[[(2S)-2-[[(2S)-2-[[2-(3-chlorophenyl)-2,2-difluoro-acetyl]amino]-3-hydroxypropanoyl]amino]-2-(4-methoxyphenyl)acetyl]amino]-2,2-difluoro-5-methyl-3-oxo-N-(2,2,2-trifluoroethyl)hexanamide;
and pharmaceutically acceptable salts thereof.

Also particular examples of compounds of formula (I) as described herein are selected from
(4S)-4-[[(2S)-2-[[(2S)-2-[[2,2-difluoro-2-(3-fluorophenyl)acetyl]amino]-3-hydroxypropanoyl]amino]-2-(4-methoxyphenyl)acetyl]amino]-2,2-difluoro-5-methyl-3-oxo-N-(2,2,2-trifluoroethyl)hexanamide;
tert-butyl N-[[4-[(2S)-2-[(3-chlorobenzoyl)amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenyl]methyl]carbamate;
tert-butyl N-[[4-[(2S)-2-[[2-(3-chlorophenyl)-2,2-difluoro-acetyl]amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenyl]methyl]carbamate;
N-[(2S)-3-[4-(aminomethyl)phenyl]-1-[[(1S)-2-[[(3S)-5,5-difluoro-2-methyl-4,6-dioxo-6-(2,2,2-trifluoroethyl-amino)hexan-3-yl]amino]-1-(4-methoxyphenyl)-2-oxoethyl]amino]-1-oxopropan-2-yl]-3-chlorobenzamide trifluoroacetic acid;
(4S)-4-[[(2S)-2-[[(2S)-3-[4-(aminomethyl)phenyl]-2-[[2-(3-chlorophenyl)-2,2-difluoroacetyl]amino]propanoyl]amino]-2-(4-methoxyphenyl)acetyl]amino]-2,2-difluoro-5-methyl-3-oxo-N-(2,2,2-trifluoroethyl)hexanamide, trifluoroacetic acid;
(4S)-4-[[(2S)-2-[[(2S)-2-[[2,2-difluoro-2-(3-fluorophenyl)acetyl]amino]-3-methoxypropanoyl]amino]-2-(4-methoxyphenyl)acetyl]amino]-2,2-difluoro-5-methyl-3-oxo-N-(2,2,2-trifluoroethyl)hexanamide;
(4S)-4-[[(2S)-2-[[(2S)-2-[[2-(3,4-dichlorophenyl)-2,2-difluoroacetyl]amino]-3-methoxypropanoyl]amino]-2-(4-methoxyphenyl)acetyl]amino]-2,2-difluoro-5-methyl-3-oxo-N-(2,2,2-trifluoroethyl)hexanamide;
(4S)-4-[[(2S)-2-[[(2S)-2-[[2-(2,5-dichlorophenyl)-2,2-difluoroacetyl]amino]-3-methoxypropanoyl]amino]-2-(4-methoxyphenyl)acetyl]amino]-2,2-difluoro-5-methyl-3-oxo-N-(2,2,2-trifluoroethyl)hexanamide;
(4S)-4-[[(2S)-2-[[(2S)-2-[[2-(3-chlorophenyl)-2,2-difluoro-acetyl]amino]-3-methoxypropanoyl]amino]-2-(4-methoxyphenyl)acetyl]amino]-N-[2-(1,1-dioxo-1,4-thi-azinan-4-yl)ethyl]-2,2-difluoro-5-methyl-3-oxohexanamide;
N-[(2S)-1-[[(1S)-2-[[(3S)-6-[2-(1,1-dioxo-1,4-thiazinan-4-yl)ethylamino]-5,5-difluoro-2-methyl-4,6-dioxohexan-3-yl]amino]-1-(4-methoxyphenyl)-2-oxoethyl]amino]-3-methoxy-1-oxopropan-2-yl]-1-(trifluoromethyl)cyclopentane-1-carboxamide;
and pharmaceutically acceptable salts thereof.

Processes for the manufacture of compounds of formula (I) as described herein are an object of the invention.

Synthesis

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reaction and purification of the resulting products are known to those persons skilled in the art. In case a mixture of enantiomers or diastereomers is produced during a reaction, these enantiomers or diastereomers can be separated by methods described herein or known to the man skilled in the art such as, e.g., chromatography on a chiral column or crystallization. The substituents and indices used in the following description of the processes have the significance given herein.

The following abbreviations are used in the present text: BOC=t-butyloxycarbonyl, DBU=2,3,4,6,7,8,9,10-octahydro-pyrimido[1,2-a]azepine, DCE=1,2-dichloroethane, DCM=dichloromethane, DIAD=diisopropyl-azodicarboxylate, DCC=N,N'-dicyclohexylcarbodiimide, DMAP=4-dimethylaminopyridine, DMF=N,N-dimethylformamide, EDCI=N-(3-dimethylaminopropyl)-N'-ethylcarbodiimide hydrochloride, eq.=equivalents, HATU=O-(7-azabenzotriazol-1-yl)-1,1,3,3-tetramethyluronium hexafluorophosphate, HPLC=high performance liquid chromatography, HOBT=1-hydroxybenzo-triazole, Huenig's base=iPr$_2$NEt=N-ethyl diisopropylamine, LAH=lithium aluminum hydride, PG=protecting group, rt=room temperature, TBME=t-butyl methyl ether, TBTU=O-benzotriazol-1-yl-N,N,N',N'-tetramethyl-uronium tetrafluoroborate, TEA=Et$_3$N=triethylamine, TFA=trifluoroacetic acid, THF=tetrahydrofuran, quant.=quantitative.

The synthesis of compounds of the general formula I can be accomplished according to scheme 1. Appropriately protected (e.g., with a BOC-group) α-amino-aldehyde 1 is reacted with the Reformatsky reagent derived from ethyl 2-bromo-2,2-difluoroacetate 2 to provide, under chelation control, amino-hydroxy-ester 3 (scheme 1, step a). The latter is transformed into amide 5 by treatment with the necessary amine 4 at elevated temperature, typically in boiling methanol (scheme 1, step b). Conventional deprotection, in the case of a BOC group with, e.g., TFA in DCM or anhydrous HCl in dioxane or a mixture of dioxane and MeOH, delivers free amine 6 (scheme 1, step c) which can then be coupled with the building block 7 (for its synthesis, see below) under standard peptide coupling conditions, e.g., with HATU or TBTU, and an appropriate base, e.g., Huenig's base or TEA, in an inert solvent like DMF, to furnish intermediate 8 (scheme 1, step d). Alternatively, amine 6 is coupled with NHS-ester 7' under Schotten Baumann-conditions in a mixture of, e.g., THF, DME, and water, in the presence of a mild base like NaHCO$_3$, to generate the very same intermediate 8 (scheme 1, step d). Eventually, oxidation, e.g., with Dess Martin periodinane, in an inert solvent like DCM or a mixture of DCM and THF as solubilizing agent, generates the final target molecule I. Starting aldehyde 1 which is prone to racemization—in case one of R$^2$ or R$^3$ is hydrogen—is prepared as described in literature from the corresponding Weinreb amide by reduction with LAH and used immediately for the next step (J. Med. Chem. 1992, 35, 4795-4808).

Scheme 1

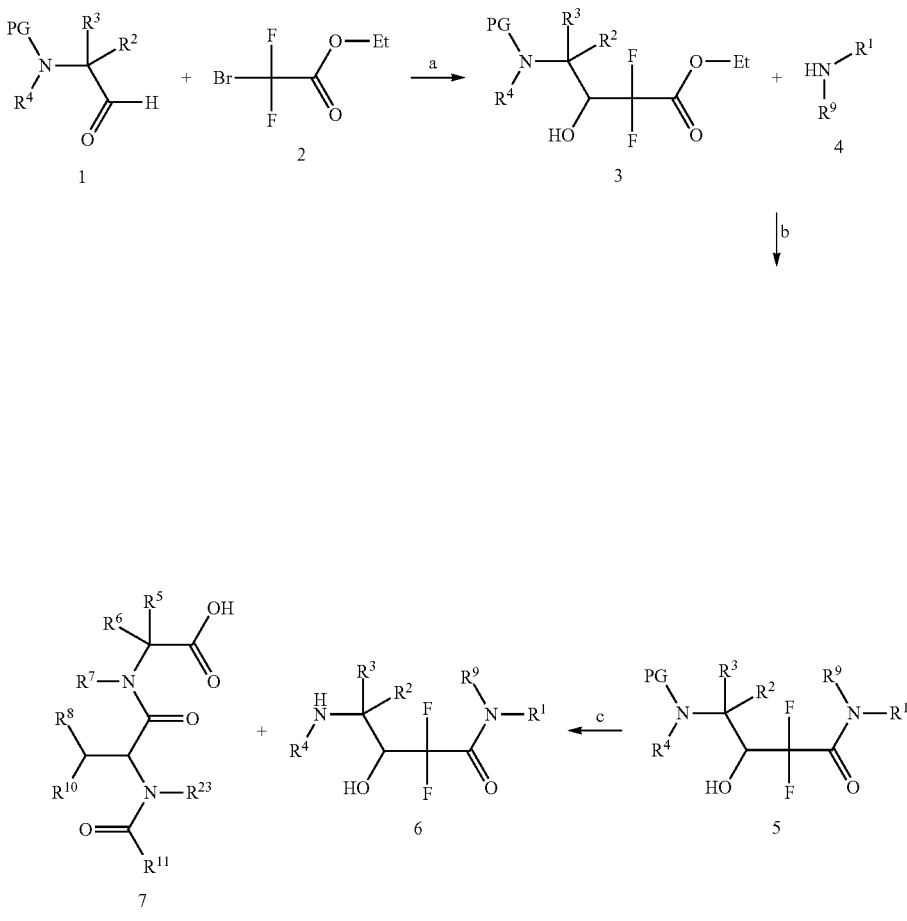

or

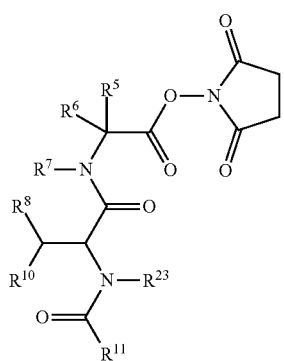

7'

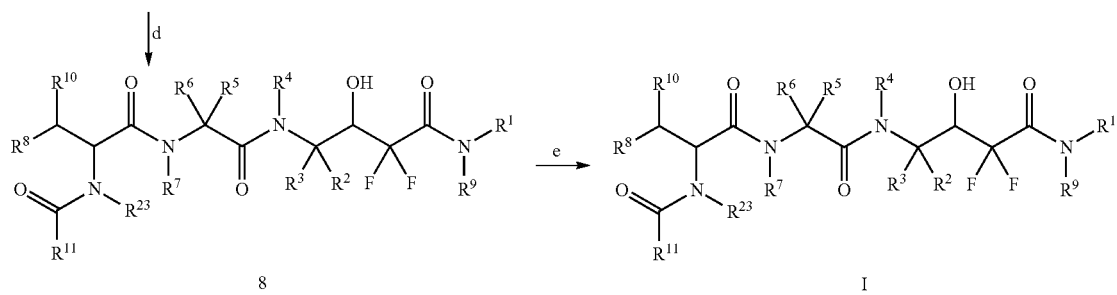

Building block 7 used in scheme 1 can be synthesized as summarized in scheme 2. The appropriate, commercially available amino acid 1 is transformed into the corresponding bis-silylated derivative 2 by treatment with two equivalents of trimethylsilyl chloride and a tertiary amine, e.g., TEA or Huenig's base (scheme 2, step a); or, if R7 unequal hydrogen, with one equivalent of trimethylsilyl chloride. The nitrogen of the latter is then acylated by treatment with the acid 3 and a conventional coupling reagent like HATU or TBTU and an appropriate base, e.g., Huenig's base, in an inert solvent like DCM, to give the anticipated intermediate (scheme 2, step b).

NHS-ester 7' of scheme 1 can be obtained from 7 by treatment with 1-hydroxypyrrolidine-2,5-dione, EDC, and pyridine in DCM at ambient temperature.

Scheme 2

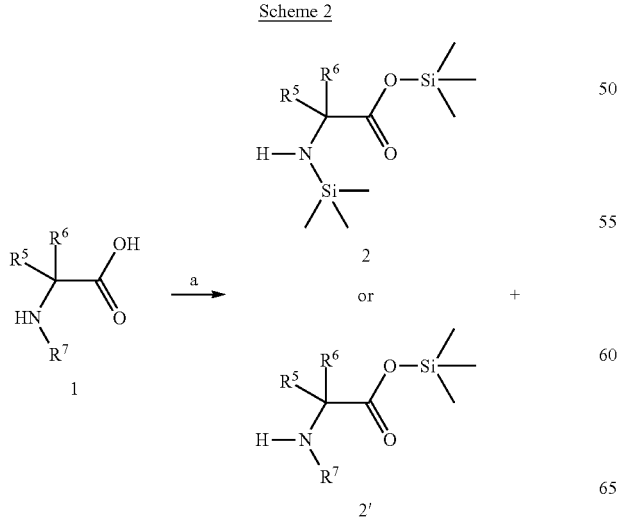

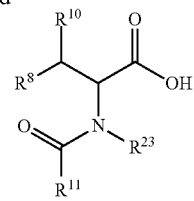

3

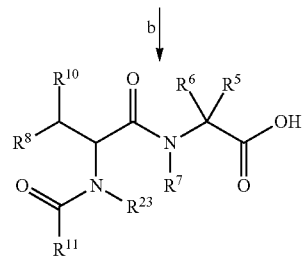

7 of scheme 1

In another synthetic variant, as outlined in scheme 3, intermediate 6 of scheme 1 is first elongated with an appropriately protected, e.g., with the BOC-group, amino acid 1 under standard conditions by treatment with a coupling reagent such as TBTU, HATU, EDCI/HOBT, etc., and a base like Huenig's base or TEA in an inert solvent like N,N-dimethylformamide to yield 2 (scheme 3, step a). After deprotection to 3, e.g., by treatment with TFA in DCM or anhydrous HCl in dioxane or a mixture of dioxane and MeOH (scheme 3, step b), the latter is coupled with NHS-ester 4 under Schotten Baumann-conditions in a mixture of, e.g., THF, DME, and water, in the presence of a mild base like NaHCO₃, to generate the penultimate intermediate 5 (scheme 3, step c). Oxidation of the free alcohol, e.g., with Dess Martin periodinane, in an inert solvent like DCM, delivers finally the target molecule I. In still another embodiment, 3 can also be coupled with free acid 4' under classical petide coupling conditions as described above.

dioxane and MeOH (scheme 4, step b), the latter is coupled with the NHS-ester of acid 4 (=4") under Schotten Baumann-conditions in a mixture of, e.g., THF, DME, and water, in the presence of a mild base like NaHCO$_3$, or

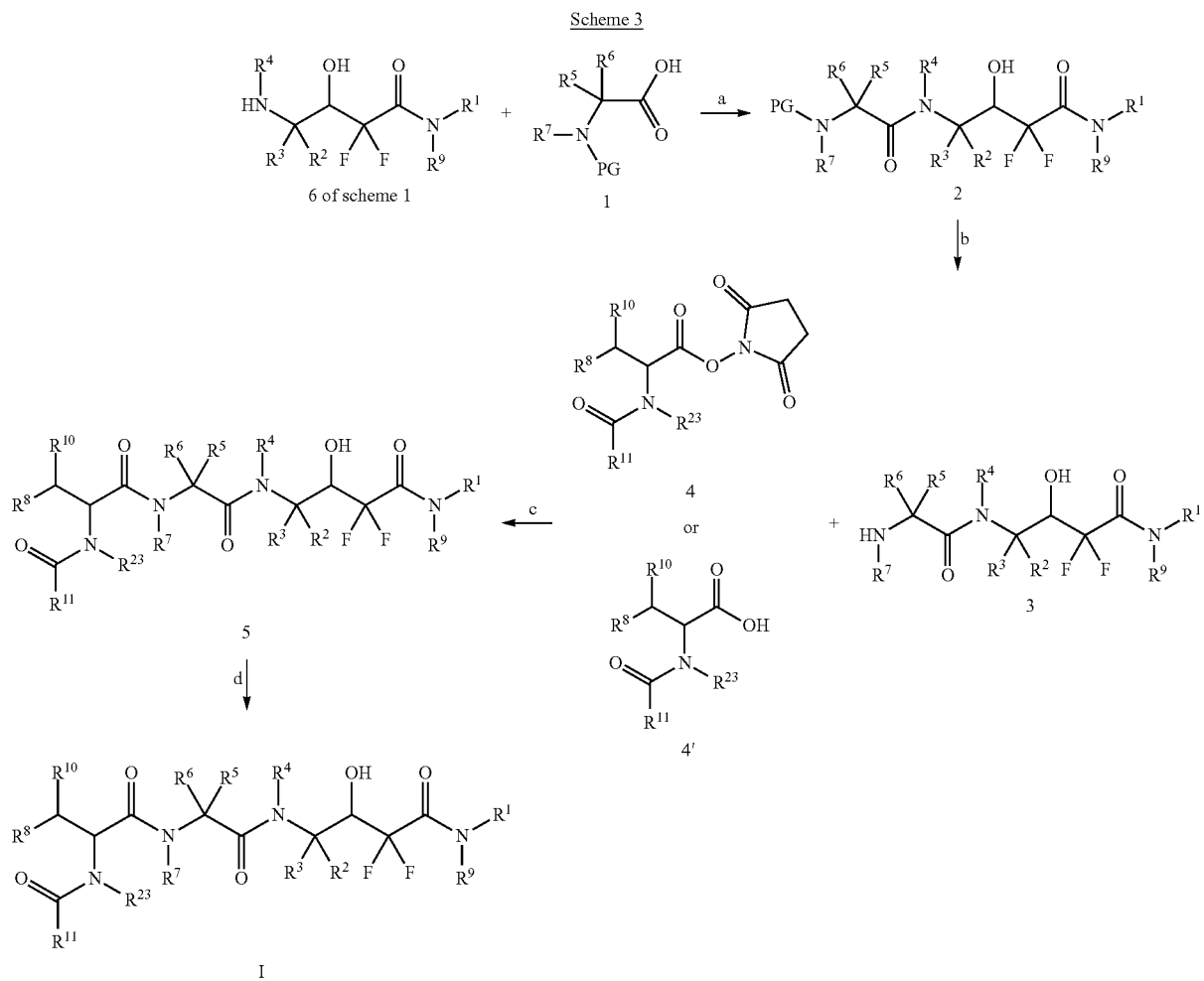

In still another embodiment, amine 3 of scheme 3 is first elongated with an appropriately, e.g., BOC-protected, amino acid amino acid 1 under standard conditions by treatment with a coupling reagent such as TBTU, HATU, EDCI/HOBT, etc., and a base like Huenig's base or TEA in an inert solvent like N,N-dimethylformamide to yield 2 (scheme 4, step a). After deprotection to 3, e.g., by treatment with TFA in DCM or anhydrous HCl in dioxane or a mixture of preferably, with 4 itself under classical petide coupling conditions as described above, or, finally, with acid chloride 4' and a base like Huenig's base or TEA in an inert solvent like N,N-dimethylformamide or DCM to generate the penultimate intermediate 5 (scheme 3, step c). Oxidation of the free alcohol, e.g., with Dess Martin periodinane, in an inert solvent like DCM, delivers finally the target molecule I.

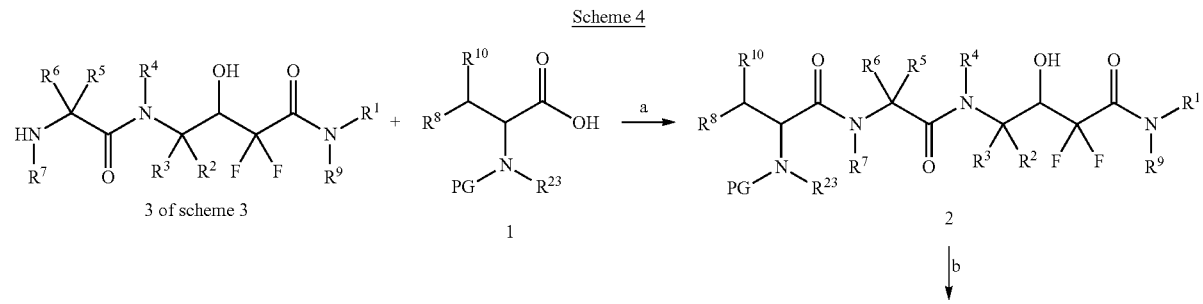

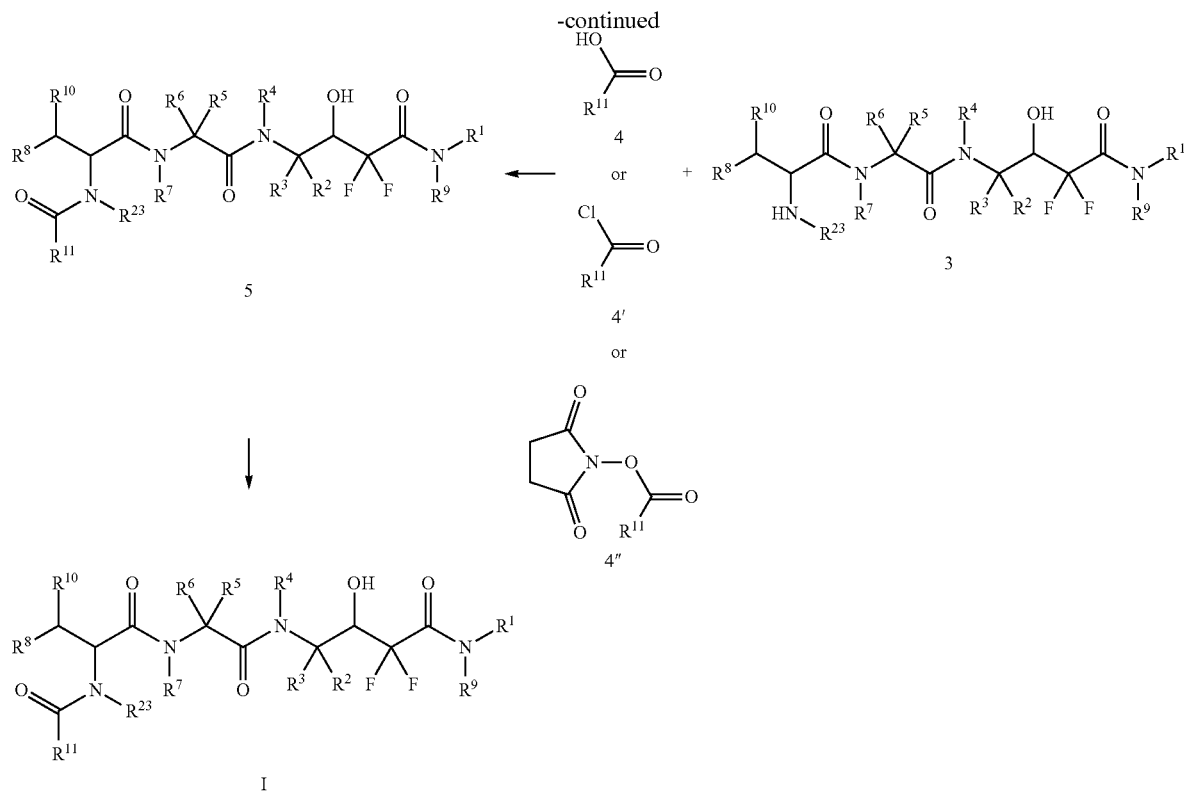

Acid 3 in scheme 2, identical to acid 4' in scheme 3, can be, if not commercial available, prepared as follows:

Scheme 5

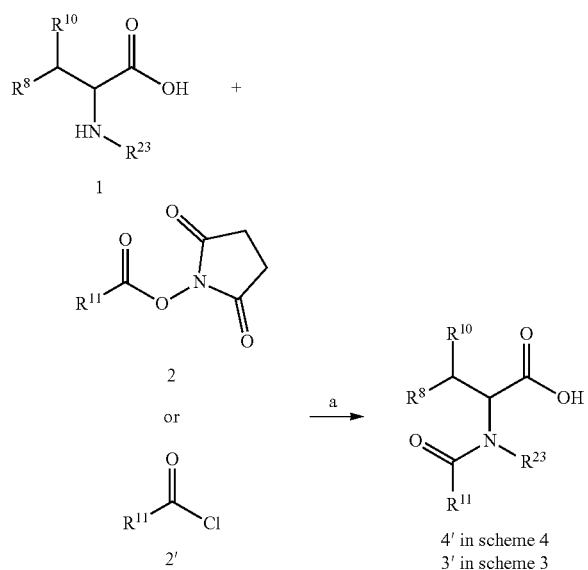

Amino acid 1 is coupled with NHS-ester 2 under Schotten Baumann-conditions in a mixture of, e.g., THF, DME, and water, in the presence of a mild base like NaHCO$_3$ to provide the desired N-acylated amino acid. Building block 2 can be obtained from readily available acids R$^{11}$—COOH by treatment with 1-hydroxypyrrolidine-2,5-dione, EDC, and pyridine in DCM at ambient temperature. In case R$^8$ and/or R$^{10}$ contain sensitive functional groups, they have to be protected; an alcohol e.g. as tert-butyldimethylsilyl ether, an acid as tert-butyl ester, or an amine as BOC-derivative. The respective functional groups are later liberated at the final stage by treatment with mild acid, e.g. dilute HCl, or fluoride ions, e.g. TBAF in THF, for silyl ethers, or by treatment with moderately acidic conditions like TFA in DCM or anhydrous HCl in dioxane or a mixture of dioxane and MeOH. Alternatively, amino acid 1 cn also be reacted with acid chloride 2' (scheme 5).

In still another variant, the benzyl ester of the amino acid in scheme 5 is coupled with the appropriate acid R$^{11}$—COOH by treatment with a coupling reagent such as TBTU, HATU, EDCI/HOBT, etc., and a base like Huenig's base or TEA in an inert solvent like DMF to yield 3 (scheme 6, step a). After hydrogenolytical cleavage with H$_2$ (atmospheric pressure)/Pd on charcoal in an inert solvent like ethyl acetate or ethanol, one obtains the very same intermediate (scheme 6, step b).

Scheme 6

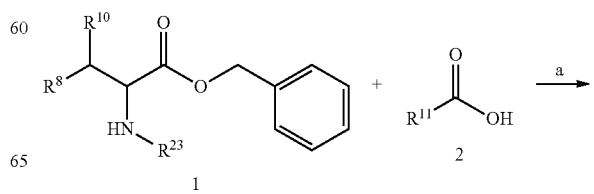

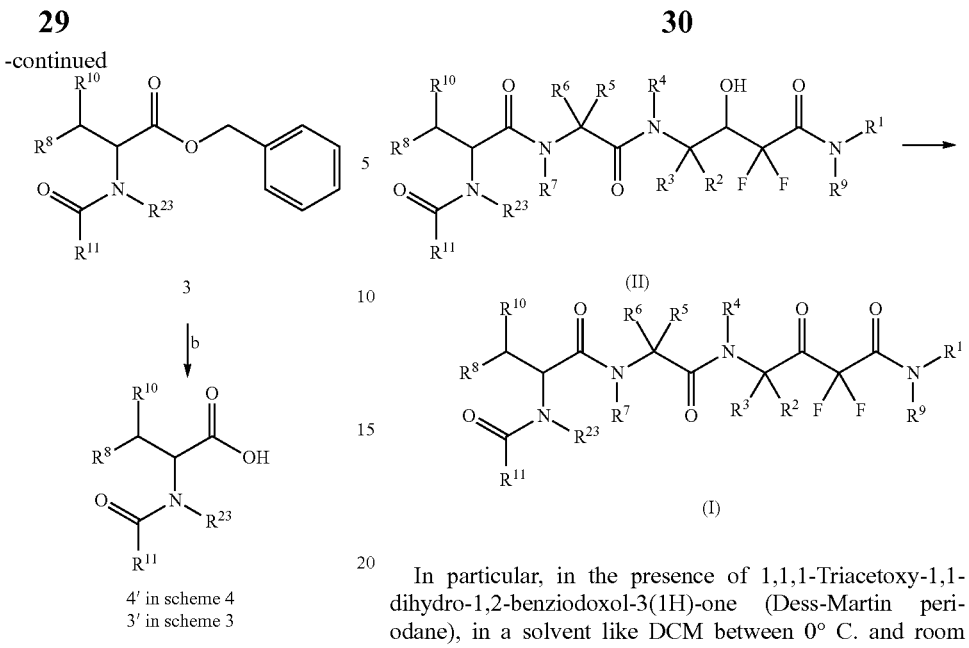

(II)

(I)

In particular, in the presence of 1,1,1-Triacetoxy-1,1-dihydro-1,2-benziodoxol-3(1H)-one (Dess-Martin periodane), in a solvent like DCM between 0° C. and room temperature.

wherein $R^1$, $R^2$, $R^3$, $R^4$, $R^5$, $R^6$, $R^7$, $R^3$, $R^8$, $R^9$, $R^{10}$, $R^{11}$ and $R^{23}$ are as defined above.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of ocular diseases, in particular HtrA1-mediated ocular diseases, more particularly wet or dry age-related macular degeneration, geographic atrophy, diabetic retinopathy, retinopathy of prematurity or polypoidal choroidal vasculopathy.

In a particular embodiment, the compounds of formula (I) or their pharmaceutically acceptable salts and esters can be used for the treatment or prophylaxis of wet or dry age-related macular degeneration, geographic atrophy, diabetic retinopathy, retinopathy of prematurity or polypoidal choroidal vasculopathy.

The present invention also relates to the use of a compound according to formula (I) as described herein for the preparation of a medicament for the treatment or prophylaxis of wet or dry age-related macular degeneration, geographic atrophy, diabetic retinopathy, retinopathy of prematurity and polypoidal choroidal vasculopathy.

Also an object of the invention is a method for the treatment or prophylaxis of wet or dry age-related macular degeneration, geographic atrophy, diabetic retinopathy, retinopathy of prematurity and polypoidal choroidal vasculopathy, which method comprises administering an effective amount of a compound according to formula (I) as described herein.

Also an embodiment of the present invention are compounds of formula (I) as described herein, when manufactured according to any one of the described processes.

Assay Procedures

Protein purification for use in enzymatic assays

Human HtrA1 protein comprising the catalytic and the PDZ domain from amino acid Asp161 up to Pro480 was expressed in BL21(DE3) cells as an N-terminal fusion Also an embodiment of the present invention is a process to prepare a compound of formula (I) as defined above comprising i) the reaction of a compound of formula (III) with a compound of formula (IV)

In particular, in the presence of a base such as diisopropylamide, and in the presence of a coupling reagent, such as HATU, in a solvent like DMF between 0° C. and room temperature then ii) the reaction of a compound of formula (II) in oxidative conditions protein with a 6×His-SUMO tag. The transformed cells were grown in LB medium at 37° C. until the optical density at 600 nm was between 0.6 and 0.8. Then, the temperature was decreased to 18° C. and the recombinant protein production induced by adding IPTG to a final concentration of 250 mM. Fermentation was performed over night at 18° C.

The protein was purified to homogeneity following a four-step procedure. 40 g of cells were suspended in 50 mM HEPES pH 7.8, 250 mM NaCl, 10 mM MgCl2, 0.35% CHAPS, 10% glycerol containing 20 tabs per liter of EDTA-free cOmplete™ Protease Inhibitor (Roche) as well as 30 mg/l DNAse and Rnase. The cells were broken by a single passage through a homogenizer at 750 bar and then centrifuged at 20'000×g for 30 minutes. The clear supernatant was applied on a triple 5 ml HisTrap column (GE Healthcare) equilibrated in 50 mM HEPES pH 7.8, 500 mM NaCl, 0.35% CHAPS, 10% glycerol. After washing with stepwise increasing concentrations of imidazole (20 mM, 40 mM, 50 mM) HtrA1 fusion protein was eluted within a linear gradient from 10 to 100% of the same buffer containing 500 mM imidazole. HtrA1 containing fractions were pooled, concentrated and then applied to a Superdex S200 prep grade (XK26/100-GE Healthcare) column equilibrated in 50 mM ethanolamine pH 9.6, 500 mM NaCl, 0.35% CHAPS, 10% glycerol, 0.02% sodium azide. In order to cleave the SUMO fusion protein and to release active HtrA1, the pooled fractions from the size exclusion chromatography were blended with SUMO protease (Life Technologies) and incubated ca. 20 hours at RT. HtrA1 was isolated out of the reaction solution by chromatography on a Superdex S200 prep grade (XK26/100-GE Healthcare) column equilibrated 50 mM ethanolamine pH 9.6, 500 mM NaCl, 0.35% CHAPS, 10% glycerol, 0.02% sodium azide. Fractions containing active HtrA1 were pooled and concentrated. Following the above strategy 150 mg of the HtrA1 (catalytical domain/PDZ construct) could be purified. As shown by RP-HPLC and SDS-PAGE, >98% pure protein was obtained.

HtrA1 Enzyme Inhibition Assay

Enzyme activity is measured by observing the increase in fluorescence intensity caused by cleavage of a peptide substrate containing a fluorophore, whose emission is quenched in the intact peptide.

Assay buffer: 500 mM Tris pH 8.0, 200 mM NaCl, 0.025% CHAPS, 0.005% BSG

Enzyme: human HtrA1 Cat-PDZ, final concentration 1 nM

Substrate: Mca-Ile-Arg-Arg-Val-Ser-Tyr-Ser-Phe-Lys(Dnp)-Lys (SEQ ID NO: 1), final concentration 500 nM (from Innovagen Cat: SP-5076-1, Lot: 89584.02)

Mca=(7-Methoxycoumarin-4-yl)acetyl
Dnp=2,4-Dinitrophenyl
Final volume: 51 µl
Excitation 320 nm, emission 390 nm After a pre-incubation of the HtrA1 protease for 30 min with compounds, substrate is added to the wells and initial RFU is measured. Upon incubation for 2 hours at RT, the enzymatic activity cleaved the substrate releasing fluorescent Mca-peptide conjugate and the final RFU value is measured. The presence of inhibitors leads to a decreased final RFU.

For the analysis ΔRFU is calculated as $RFU_{end} - RFU_{stat}$ and then percent inhibition is calculated with the following formula:

$$PCT\_Inhibition = 100 - 100 * (\Delta RFU_{compound} - \Delta RFU_{blank})/(\Delta RFU_{negctr} - \Delta RFU_{blank})$$

where
neg.ctrl is protease with substrate and DMSO
blank is as neg. ctrl without protease
compound is as neg. ctrl with test compounds at desired concentration The $IC_{50}$ is determined using a 4-point Hill-fit equation where
x=concentration of test compound
A=extrapolated value of the curve at effector concentration equals 0
B=extrapolated value of the curve at effector concentration equals infinite
C=concentration at the inflection point of the sigmoidal curve ($IC_{50}$)
D=Hill coefficient of slope at the inflection point of the fitted curve $$Y(x) = A + \frac{B - A_D}{1 + \left(\frac{C}{x}\right)}$$

As a counter screen the compounds are added to the protease-substrate reaction mix only after 2 h incubation, when all the substrate is turned over, to identify auto-fluorescent or absorbing compounds giving false positive hits.

| Example | IC50 (µM) |
| --- | --- |
| 1 | 0.0083 |
| 2 | 0.0023 |
| 3 | 0.0086 |
| 4 | 0.0093 |
| 5 | 0.0015 |
| 6 | 0.0008 |
| 7 | 0.0011 |
| 8 | 0.0030 |
| 9 | 0.0021 |
| 10 | 0.0068 |
| 11 | 0.0024 |
| 12 | 0.0124 |
| 13 | 0.0068 |
| 14 | 0.0013 |
| 15 | 0.0004 |
| 16 | 0.0005 |
| 17 | 0.0005 |
| 18 | 0.0006 |
| 19 | 0.0175 |
| 20 | 0.0005 |
| 21 | 0.0375 |
| 22 | 0.0006 |
| 23 | 0.0161 |
| 24 | 0.0287 |
| 25 | 0.0222 |
| 26 | 0.0064 |
| 27 | 0.0363 |
| 28 | 0.0202 |
| 29 | 0.0023 |
| 30 | 0.0043 |
| 31 | 0.0090 |
| 32 | 0.0005 |
| 33 | 0.0003 |
| 34 | 0.0005 |
| 35 | 0.0005 |
| 36 | 0.0005 |
| 37 | 0.0009 |
| 38 | 0.0773 |
| 39 | 0.0680 |
| 40 | 0.0795 |
| 41 | 0.0006 |
| 42 | 0.0003 |
| 43 | 0.0005 |

-continued

| Example | IC50 (µM) |
|---|---|
| 44 | 0.0004 |
| 45 | 0.0004 |
| 46 | 0.0009 |
| 47 | 0.0007 |
| 48 | 0.0003 |
| 49 | 0.0016 |
| 50 | 0.0009 |
| 51 | 0.0008 |
| 52 | 0.0004 |
| 53 | 0.0006 |
| 54 | 0.0017 |
| 55 | 0.0006 |
| 56 | 0.0005 |
| 57 | 0.0006 |
| 58 | 0.0004 |
| 59 | 0.0020 |
| 60 | 0.0015 |
| 61 | 0.0026 |

Compounds of formula (I) and their pharmaceutically acceptable salts or esters thereof as described herein have $IC_{50}$ values between 0.00001 µM and 1000 µM, particular compounds have $IC_{50}$ values between 0.0005 µM and 500 µM, further particular compounds have $IC_{50}$ values between 0.0005 µM and 50 µM, more particular compounds have $IC_{50}$ values between 0.0005 µM and 5 µM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations; lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg, can be administered either by single dose per day or per week, or by multiple doses (2 to 4) per day, or by multiple doses per week. In case of parenteral application, such as intramuscularly, intravenously, or intraocularly, the formulation can contain 0.001% to 15% by weight of medicament and the required dose, which can be between 0.01 and 25 mg, can be administered either by single dose per day, per week or per month, or by multiple doses (2 to 4) per day, or by multiple doses per week or per month. It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

Abbreviations: aq.=aqueous; CAS-RN=Chemical Abstracts Service Registry Number; HPLC=high performance liquid chromatography; MS=mass spectrum; sat.=saturated Examples Intermediate Ia (3R,4S)-4-amino-2,2-difluoro-3-hydroxy-5-methyl-N-(2,2,2-trifluoroethyl)hexanamide

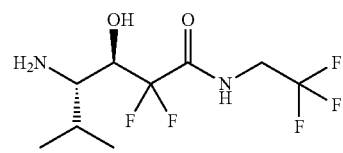 [SMILES: CC(C)[C@H](N)[C@@H](O)C(F)(F)C(=O)NCC(F)(F)F]

[A] (S)-tert-Butyl (3-methyl-1-oxobutan-2-yl)carbamate

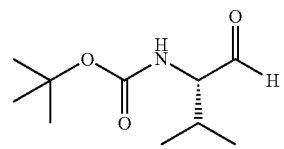

To a solution of commercially available (S)-tert-butyl (1-(methoxy(methyl)amino)-3-methyl-1-oxobutan-2-yl)carbamate (3 g, 11.5 mmol, Eq: 1) in THF (100 ml) under argon at 0° C. was added LiAlH$_4$ 1M in THF (11.5 ml, 11.5 mmol, Eq: 1) dropwise over 3 min (0→4° C.). After stirring for 20 min in the cold, the reaction mixture was quenched with 1N KHSO$_4$ solution and extracted with EtOAc; the layers were separated and the aqueous layer was back-extracted with EtOAc. The organic layers were combined, dried over Na$_2$SO$_4$ and concentrated in vacuo to yield the title compound as a colorless liquid, 2.38 g, which was used immediately for the next step.

[B] Ethyl (3R,4S)-4-amino-2,2-difluoro-3-hydroxy-5-methylhexanoate

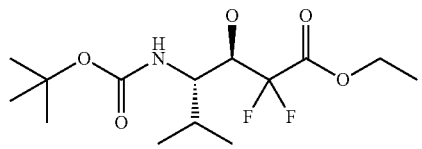 [SMILES: CCOC(=O)C(F)(F)[C@H](O)[C@@H](NC(=O)OC(C)(C)C)C(C)C]

A solution of the above prepared (S)-tert-butyl (3-methyl-1-oxobutan-2-yl)carbamate (2.01 g, 9.99 mmol, Eq: 1) and ethyl 2-bromo-2,2-difluoroacetate (6.08 g, 3.84 ml, 30 mmol, Eq: 3) in THF (15 ml) was added dropwise to a suspension of activated zinc (1.96 g, 30 mmol, Eq: 3) in THF (65 ml). Afterwards, the reaction was brought to reflux for 2 hours. The heat source was removed and the reaction was allowed to cool to ambient temperature. The reaction mixture was poured into 15 mL 1N KHSO$_4$ and extracted with EtOAc (2×25 mL). The organic layers were combined, washed with brine, dried over Na$_2$SO$_4$, and concentrated in vacuo. The crude material was purified by flash chromatography (silica gel, 120 g, 20% EtOAc in heptane) to deliver 1.41 g of the title compound as colorless oil.

[C] tert-butyl N-[(3S,4R)-5,5-difluoro-4-hydroxy-2-methyl-6-oxo-6-(2,2,2-trifluoroethylamino)hexan-3-yl]carbamate

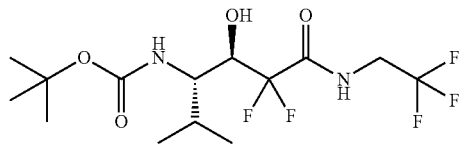 [SMILES: CC(C)[C@H](NC(=O)OC(C)(C)C)[C@@H](O)C(F)(F)C(=O)NCC(F)(F)F]

A mixture of the above prepared ethyl (3R,4S)-4-amino-2,2-difluoro-3-hydroxy-5-methylhexanoate (191.4 mg, 588 µmol, Eq: 1), 3,3,3-trifluoropropan-1-amine (333 mg, 2.94 mmol, Eq: 5) and N,N-diisopropylethylamine (380 mg, 514 µl, 2.94 mmol, Eq: 5) was refluxed in 5 mL of MeOH overnight. TLC after 17 hours showed the reaction to be finished. The reaction volume was reduced in vacuo and to the residue was added EtOAc. The organic layer was washed with brine (3×), dried over Na$_2$SO$_4$, and concentrated in vacuo. The crude material was purified by flash chromatography (silica gel, 20 g, 15% to 50% EtOAc in heptane) to produce 180 mg of the title compound as white foam; MS: 391.4 (M–H)$^-$.

[D] (3R,4S)-4-Amino-2,2-difluoro-3-hydroxy-5-methyl-N-(2,2,2-trifluoroethyl)hexanamide

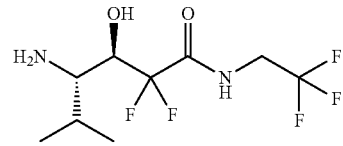 [SMILES: CC(C)[C@H](N)[C@@H](O)C(F)(F)C(=O)NCC(F)(F)F]

In a 25 mL round-bottomed flask, the above prepared tert-butyl N-[(3S,4R)-5,5-difluoro-4-hydroxy-2-methyl-6-oxo-6-(2,2,2-trifluoroethylamino)hexan-3-yl]carbamate (177 mg, 451 µmol, Eq: 1) was combined with 1,4-dioxane (6 ml) to give a colorless solution. HCl 4M in dioxane (2.25 ml, 9 mmol, Eq: 20) was added at 0° C. and the reaction mixture was stirred overnight at rt. The crude reaction mixture was concentrated in vacuo and scrupulously dried on hv and then used directly for the next step (calculated as dihydrochloride).

Intermediate Ib (3R,4S)-4-Amino-4-cyclobutyl-2,2-difluoro-3-hydroxy-N-(2,2,2-trifluoroethyl)butanamide

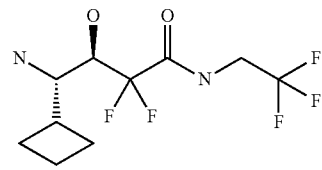 [SMILES: N[C@@H](C1CCC1)[C@@H](O)C(F)(F)C(=O)NCC(F)(F)F]

was prepared as hydrochloride in analogy to Intermediate Ia, but using in step A] tert-butyl N-[(1S)-1-cyclobutyl-2-oxoethyl]carbamate as starting material, as light yellow foam; MS: 291.1 (M+H)$^+$.

Intermediate Ic (3R,4S)-4-Amino-4-cyclopropyl-2,2-difluoro-3-hydroxy-N-(2,2,2-trifluoroethyl)butanamide

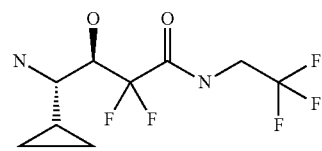 [SMILES: N[C@@H](C1CC1)[C@@H](O)C(F)(F)C(=O)NCC(F)(F)F]

was prepared as hydrochloride in analogy to Intermediate Ia, but using in step A] tert-butyl N-[(1S)-1-cyclopropyl-2-oxoethyl]carbamate as starting material, as light yellow oil.

Intermediate Id (3R,4S)-4-amino-N-[2-(1,1-dioxo-1,4-thiazinan-4-yl)ethyl]-2,2-difluoro-3-hydroxy-5-methyl-hexanamide

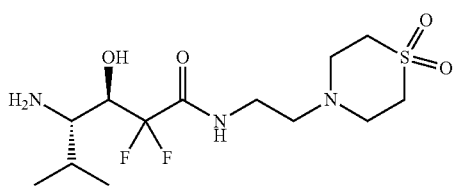 [SMILES: CC(C)[C@H](N)[C@@H](O)C(F)(F)C(=O)NCCN1CCS(=O)(=O)CC1]

was prepared as hydrochloride in analogy to Intermediate Ia, but using in step C] 2-(1,1-dioxo-1,4-thiazinan-4-yl)ethanamine instead of 3,3,3-trifluoropropan-1-amine, as white foam.

Intermediate IIa (3R,4S)-4-[[(2S)-2-Amino-2-phenylacetyl]amino]-2,2-difluoro-3-hydroxy-5-methyl-N-(2,2,2-trifluoroethyl)hexanamide

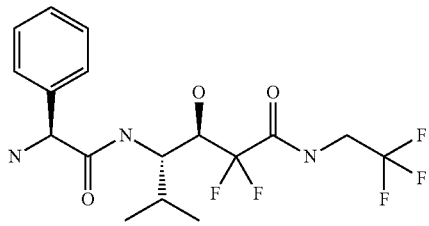 [SMILES: CC(C)[C@H](NC(=O)[C@@H](N)c1ccccc1)[C@@H](O)C(F)(F)C(=O)NCC(F)(F)F]

A] tert-Butyl N-[(1S)-2-[[(3S,4R)-5,5-difluoro-4-hydroxy-2-methyl-6-oxo-6-(2,2,2-trifluoroethylamino)hexan-3-yl]amino]-2-oxo-1-phenylethyl]carbamate

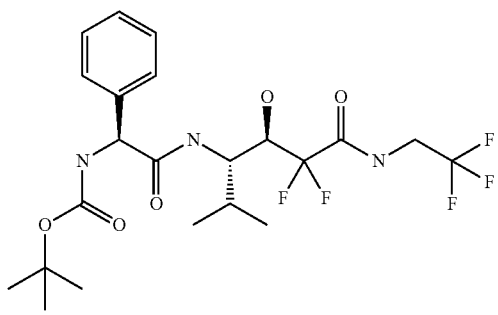 [SMILES: CC(C)[C@H](NC(=O)[C@@H](NC(=O)OC(C)(C)C)c1ccccc1)[C@@H](O)C(F)(F)C(=O)NCC(F)(F)F]

In a 25 ml flask, (3R,4S)-4-amino-2,2-difluoro-3-hydroxy-5-methyl-N-(2,2,2-trifluoroethyl)hexanamide dihydrochloride [0.3M in DMF] (Intermediate Ia, 1.33 ml, 398 µmol, Eq: 1), (S)-2-((tert-butoxycarbonyl)amino)-2-phenylacetic acid (0.100 g, 398 µmol, Eq: 1) and HATU (166 mg, 438 µmol, Eq: 1.1) were mixed in DMF (4 ml). Hunig's base (257 mg, 348 µl, 1.99 mmol, Eq: 5) was then added, and the reaction mixture was stirred at RT for 2 h. It was diluted with EtOAc, poured into 1M $KHSO_4$, and the aqueous layer was extracted with EtOAc (2×20 ml). The combined organics layers were washed with $NaHCO_3$, brine, dried over $Na_2SO_4$, and evaporated. Purification by flash chromatography (silica gel, 20 g, 20% to 100% EtOAc in heptane) generated 124 mg of the title compound as yellow foam; MS: 512.2 $(M+H)^+$.

B] (3R,4S)-4-[[(2S)-2-Amino-2-phenylacetyl]amino]-2,2-difluoro-3-hydroxy-5-methyl-N-(2,2,2-trifluoroethyl)hexanamide

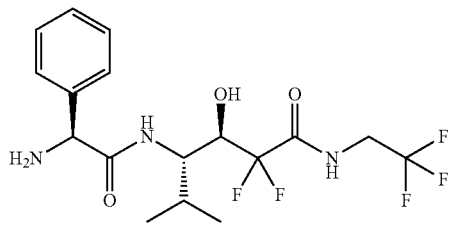

To a solution of the above prepared tert-butyl N-[(1S)-2-[[(3 S,4R)-5,5-difluoro-4-hydroxy-2-methyl-6-oxo-6-(2,2,2-trifluoroethylamino)hexan-3-yl]amino]-2-oxo-1-phenylethyl]carbamate (0.120 g, 235 µmol, Eq: 1) in MeOH (3 ml) was added HCl 4M in dioxane (293 µl, 1.17 mmol, Eq: 5); the reaction mixture was stirred at RT for 2 hours and at 40° C. for 2 hours. LC-MS indicated the reaction to be finished. The solvent was carefully evaporated to dryness to leave 119 mg of the title compound as hydrochloride as light purple foam which was used directly for the next step; MS: 412.2 $(M+H)^+$. Instead of using MeOH, the reaction can also be performed in dioxane only.

In close analogy, using in step A] (2S)-2-(4-methoxyphenyl)-2-[(2-methylpropan-2-yl)oxycarbonylamino]acetic acid, instead of (S)-2-((tert-butoxycarbonyl)amino)-2-phenylacetic acid, was prepared:

Intermediate IIb (3R,4S)-4-[[(2S)-2-Amino-2-(4-methoxyphenyl)acetyl]amino]-2,2-difluoro-3-hydroxy-5-methyl-N-(2,2,2-trifluoroethyl)hexanamide

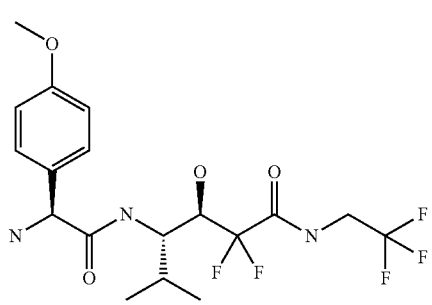 [SMILES: COc1ccc([C@H](N)C(=O)N[C@@H](C(C)C)[C@@H](O)C(F)(F)C(=O)NCC(F)(F)F)cc1]

As yellow oil; MS: 442.2 $(M+H)^+$.

Intermediate IIc (3R,4S)-4-[[(2S)-2-Amino-2-(4-methoxyphenyl)
acetyl]amino]-4-cyclobutyl-2,2-difluoro-3-hydroxy-
N-(2,2,2-trifluoroethyl)butanamide

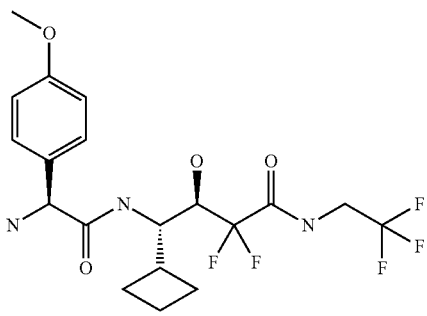 [SMILES: COc1ccc([C@H](N)C(=O)N[C@@H](C2CCC2)[C@@H](O)C(F)(F)C(=O)NCC(F)(F)F)cc1]

Was prepared in close analogy to Intermediate IIb, but starting the reaction sequence with (3R,4S)-4-amino-4-cyclobutyl-2,2-difluoro-3-hydroxy-N-(2,2,2-trifluoroethyl)butanamide hydrochloride (Intermediate Ib) instead of (3R,4S)-4-amino-2,2-difluoro-3-hydroxy-5-methyl-N-(2,2,2-trifluoroethyl)hexanamide hydrochloride (Intermediate Ia) as light brown foam; MS: 454.2 (M+H)$^+$.

Intermediate IId (3R,4S)-4-[[(2S)-2-Amino-2-(4-methoxyphenyl)
acetyl]amino]-4-cyclopropyl-2,2-difluoro-3-hydroxy-N-(2,2,2-trifluoroethyl)butanamide

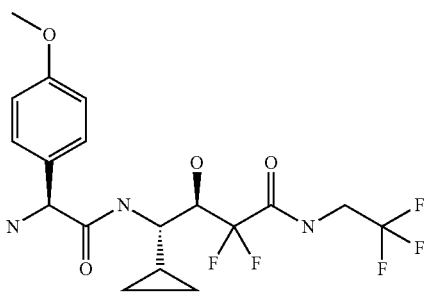

AND Enantiomer

Was prepared in close analogy to Intermediate IIb, but starting the reaction sequence with (3R,4S)-4-amino-4-cyclopropyl-2,2-difluoro-3-hydroxy-N-(2,2,2-trifluoroethyl)butanamide hydrochloride (Intermediate AND Enantiomer Ic) instead of (3R,4S)-4-amino-2,2-difluoro-3-hydroxy-5-methyl-N-(2,2,2-trifluoroethyl)hexanamide hydrochloride (Intermediate Ia), as blue foam; MS: 440.2 (M+H)$^+$.

Intermediate IIe (3R,4S)-4-[[(2S)-2-amino-2-(4-methoxyphenyl)
acetyl]amino]-N-[2-(1,1-dioxo-1,4-thiazinan-4-yl)
ethyl]-2,2-difluoro-3-hydroxy-5-methyl-hexanamide

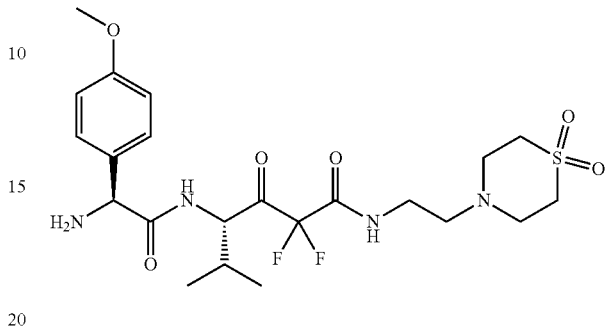

Was prepared in close analogy to Intermediate IIb, but starting the reaction sequence with (3R,4S)-4-amino-N-[2-(1,1-dioxo-1,4-thiazinan-4-yl)ethyl]-2,2-difluoro-3-hydroxy-5-methyl-hexanamide hydrochloride (Intermediate Id) instead of (3R,4S)-4-amino-2,2-difluoro-3-hydroxy-5-methyl-N-(2,2,2-trifluoroethyl)hexanamide hydrochloride (Intermediate Ia), as white foam; MS: 621.3 (M+H)$^+$.

Intermediate IIIa (4S)-4-[[(2S)-2-[[(2S)-2-Amino-3-(3-chlorophenyl)
propanoyl]amino]-2-phenylacetyl]amino]-2,2-difluoro-3-hydroxy-5-methyl-N-(2,2,2-trifluoroethyl)
hexanamide

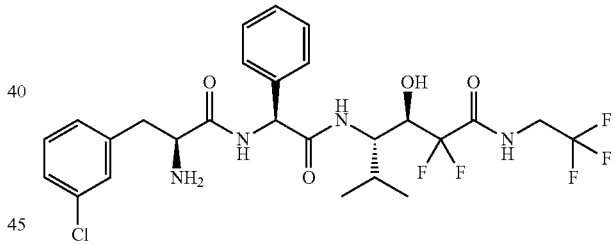

A] tert-Butyl N-[(2S)-3-(3-chlorophenyl)-1-[[(1S)-2-[[(3S)-5,5-difluoro-4-hydroxy-2-methyl-6-oxo-6-(2,2,2-trifluoroethylamino)hexan-3-yl]amino]-2-oxo-1-phenylethyl]amino]-1-oxopropan-2-yl]carbamate

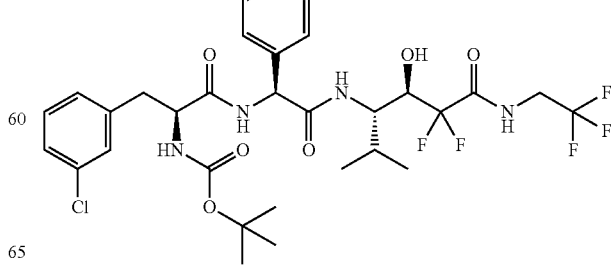

In a 50 mL pear-shaped flask, (3R,4S)-4-[[(2S)-2-amino-2-phenylacetyl]amino]-2,2-difluoro-3-hydroxy-5-methyl-N-(2,2,2-trifluoroethyl)hexanamide hydrochloride (Intermediate IIa, 463 mg, 1.03 mmol, Eq: 1) was dissolved in DMF (10 ml); (S)-2-((tert-butoxycarbonyl)amino)-3-(3-chlorophenyl)propanoic acid (310 mg, 1.03 mmol, Eq: 1), HATU (786 mg, 2.07 mmol, Eq: 2) and N,N-diisopropylethylamine (334 mg, 451 µl, 2.58 mmol, Eq: 2.5) were successively added at 0° C. and the reaction mixture was stirred for 3 hours at RT=>brown solution. The reaction was quenched with sat. NaHCO$_3$ and extracted twice with EtOAc. The organic layers were washed with 1N KHSO$_4$ and brine, combined, dried over Na$_2$SO$_4$ and concentrated in vacuo. The crude material was purified by flash chromatography (silica gel, 100 g, 30% to 80% EtOAc in heptane) to yield 510 mg of the title product as light yellow foam; MS: 693.2 (M+H)$^+$.

B] (4S)-4-[[(2S)-2-[[(2S)-2-Amino-3-(3-chlorophenyl)propanoyl]amino]-2-phenylacetyl]amino]-2,2-difluoro-3-hydroxy-5-methyl-N-(2,2,2-trifluoroethyl)hexanamide In a 50 mL round-bottomed flask, the above prepared tert-butyl N-[(2S)-3-(3-chlorophenyl)-1-[[(1S)-2-[[(3S)-5,5-difluoro-4-hydroxy-2-methyl-6-oxo-6-(2,2,2-trifluoroethylamino)hexan-3-yl]amino]-2-oxo-1-phenylethyl]amino]-1-oxopropan-2-yl]carbamate (0.506 g, 730 µmol, Eq: 1) was combined with MeOH (4 ml) to give a colorless solution. HCl in dioxane 4M (913 µl, 3.65 mmol, Eq: 5) was added at 0° C. and the reaction mixture was stirred at RT. LC-MS after 3 hours indicated the reaction to be finished. The crude reaction mixture was concentrated in vacuo and carefully dried on HV to provide the title compound as hydrochloride; it was used directly for the next step without further purification; MS: 593.1 (M+H)$^+$.

Intermediate IIIb tert-Butyl 2-[4-[(2S)-2-amino-3-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-3-oxopropyl]phenoxy]acetate

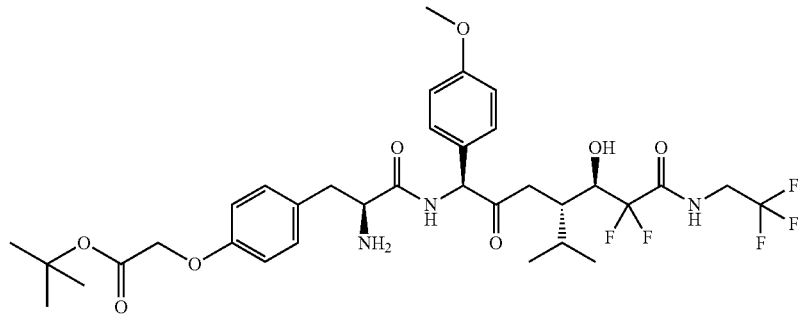 [SMILES: COc1ccc([C@H](NC(=O)[C@@H](N)Cc2ccc(OCC(=O)OC(C)(C)C)cc2)C(=O)C[C@@H](C(C)C)[C@@H](O)C(F)(F)C(=O)NCC(F)(F)F)cc1]

A] Benzyl (2S)-2-[(2-methylpropan-2-yl)oxycarbonylamino]-3-[4-[2-[(2-methylpropan-2-yl)oxy]-2-oxoethoxy]phenyl]propanoate

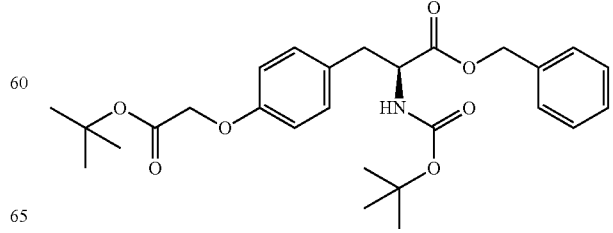

To a solution of commercially available benzyl (2S)-2-(tert-butoxycarbonylamino)-3-(4-hydroxyphenyl)propanoate (0.5 g, 1.35 mmol, Eq: 1) in DMF (20 ml) were successively added potassium carbonate (0.372 g, 2.69 mmol, Eq: 2) and dropwise tert-butyl 2-bromoacetate (0.199 ml, 1.35 mmol, Eq: 1). The reaction mixture was then stirred overnight at room temperature. The mixture was diluted with EtOAc, poured into H₂O (25 ml), and the aqueous layer was extracted with EtOAc (2×20 ml). Combined organics were dried over Na₂SO₄, filtered, and evaporated. The crude material was purified by flash chromatography (silica gel, 20 g, 0% to 60% EtOAc in heptane) to yield the title product (0.588 g) as colorless solid; MS: 484.3 (M−H)⁻.

B] (2S)-2-[(2-Methylpropan-2-yl)oxycarbonylamino]-3-[4-[2-[(2-methylpropan-2-yl)oxy]-2-oxoethoxy]phenyl]propanoic acid A solution of the above prepared benzyl (2S)-2-[(2-methylpropan-2-yl)oxycarbonylamino]-3-[4-[2-[(2-methylpropan-2-yl)oxy]-2-oxoethoxy]phenyl]propanoate (0.588 g, 1.21 mmol, Eq: 1) in methanol (20 ml) was purged several times with Ar, then Pd on C (0.064 g, 0.061 mmol, Eq: 0.05) was added and the reaction mixture was stirred at room temperature under an atmosphere of hydrogen for 1.5 hours. The catalyst was removed by filtration and the filtrate evaporated to dryness to give the title compound (0.468 g) as colorless solid; MS: 394.3 (M−H)⁻.

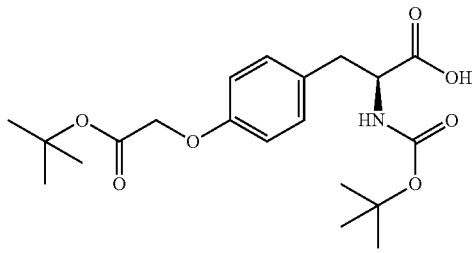 [SMILES: CC(C)(C)OC(=O)COc1ccc(C[C@H](NC(=O)OC(C)(C)C)C(=O)O)cc1]

C] tert-Butyl 2-[4-[(2S)-3-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-2-[(2-methylpropan-2-yl)oxycarbonylamino]-3-oxopropyl]phenoxy]acetate

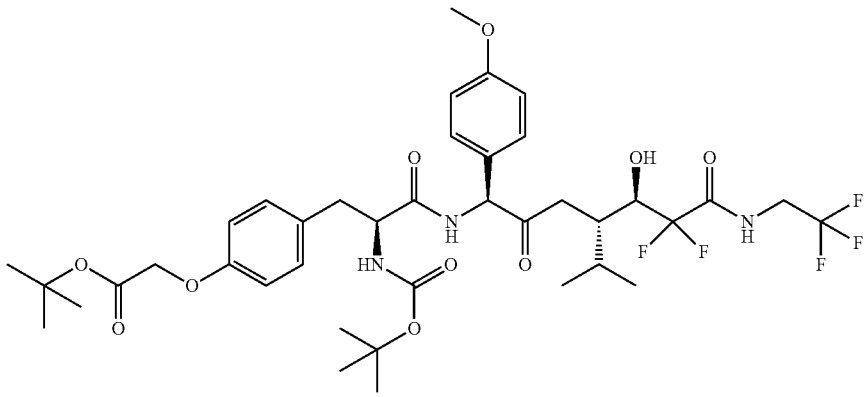 [SMILES: COc1ccc([C@H](NC(=O)[C@H](Cc2ccc(OCC(=O)OC(C)(C)C)cc2)NC(=O)OC(C)(C)C)C(=O)C[C@@H](C(C)C)[C@@H](O)C(F)(F)C(=O)NCC(F)(F)F)cc1]

In analogy to the procedure described for the preparation of intermediate IIIa [A], (3R,4S)-4-[[(2S)-2-amino-2-phenylacetyl]amino]-2,2-difluoro-3-hydroxy-5-methyl-N-(2,2,2-trifluoroethyl)hexanamide hydrochloride (Intermediate IIa) has been reacted with the above prepared (2S)-2-[(2-methylpropan-2-yl)oxycarbonylamino]-3-[4-[2-[(2-methylpropan-2-yl)oxy]-2-oxoethoxy]phenyl]propanoic acid under standard HATU coupling conditions to give the title compound as a colorless solid; MS: 819.4 (M+H)⁺.

D] tert-Butyl 2-[4-[(2S)-2-amino-3-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-3-oxopropyl]phenoxy]acetate

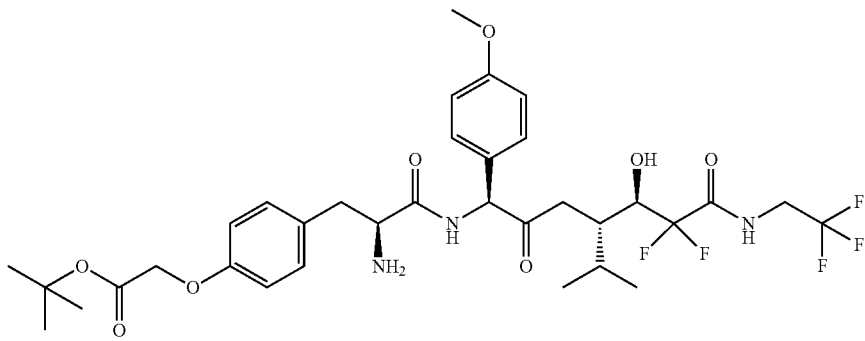 [SMILES: COc1ccc([C@H](NC(=O)[C@@H](N)Cc2ccc(OCC(=O)OC(C)(C)C)cc2)C(=O)C[C@@H](C(C)C)[C@@H](O)C(F)(F)C(=O)NCC(F)(F)F)cc1]

In analogy to the procedure described for the preparation of intermediate IIIa, the above prepared tert-butyl 2-[4-[(2S)-3-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-2-[(2-methylpropan-2-yl)oxycarbonylamino]-3-oxopropyl]phenoxy]acetate has been deprotected with 4M HCl in dioxane (step [B]) to give the title compound as hydrochloride as colorless amorphous solid; MS: 719.4 (M+H)$^+$.

Intermediate IIIc (3R,4S)-4-[[(2S)-2-[[(2S)-2-Amino-3-(3-chlorophenyl)propanoyl]amino]-2-(4-methoxyphenyl)acetyl]amino]-2,2-difluoro-3-hydroxy-5-methyl-N-(2,2,2-trifluoroethyl)hexanamide

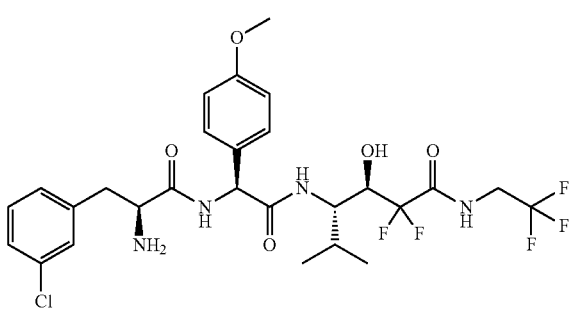 [SMILES: COc1ccc([C@H](NC(=O)[C@@H](N)Cc2cccc(Cl)c2)C(=O)N[C@@H](C(C)C)[C@@H](O)C(F)(F)C(=O)NCC(F)(F)F)cc1]

was prepared as hydrochloride in analogy to Intermediate IIIa, but using in step A] (3R,4S)-4-[[(2S)-2-amino-2-(4-methoxyphenyl)acetyl]amino]-2,2-difluoro-3-hydroxy-5-methyl-N-(2,2,2-trifluoroethyl)hexanamide (Intermediate IIb) instead of (3R,4S)-4-[[(2S)-2-amino-2-phenylacetyl]amino]-2,2-difluoro-3-hydroxy-5-methyl-N-(2,2,2-trifluoroethyl)-hexanamide hydrochloride (Intermediate IIa), as off-white foam; MS: 623.3 (M+H)$^+$.

Intermediate IIId (3R,4S)-4-[[(2S)-2-[[(2S)-2-Amino-3-(3-fluorophenyl)propanoyl]amino]-2-(4-methoxyphenyl)acetyl]amino]-2,2-difluoro-3-hydroxy-5-methyl-N-(2,2,2-trifluoroethyl)hexanamide was prepared as hydrochloride in analogy to Intermediate IIIc, but using in step A] (2S)-3-(3-fluorophenyl)-2-[(2-methylpropan-2-yl)oxycarbonylamino]propanoic acid instead of (2S)-3-(3-chlorophenyl)-2-[(2-methylpropan-2-yl)oxycarbonylamino]propanoic acid, as off-white foam; MS: 607.5 (M+H)$^+$.

Intermediate IIIe (3R,4S)-4-[[(2S)-2-[[(2S)-2-Amino-3-(3-cyanophenyl)propanoyl]amino]-2-(4-methoxyphenyl)acetyl]amino]-2,2-difluoro-3-hydroxy-5-methyl-N-(2,2,2-trifluoroethyl)hexanamide

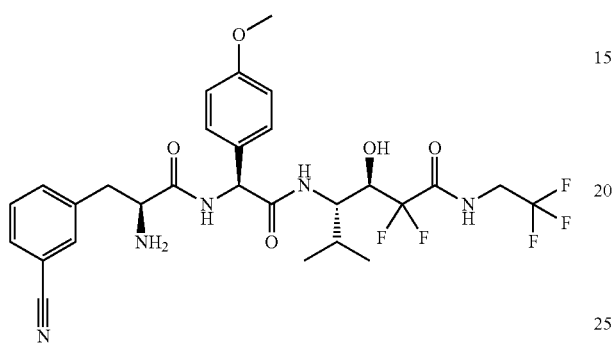

was prepared as hydrochloride in analogy to Intermediate IIIc, but using in step A] (2S)-3-(3-cyanophenyl)-2-[(2-methylpropan-2-yl)oxycarbonylamino]propanoic acid instead of (2S)-3-(3-chlorophenyl)-2-[(2-methylpropan-2-yl)oxycarbonylamino]propanoic acid, as light brown solid; MS: 614.3 (M+H)$^+$.

Intermediate IIIf (3R,4S)-4-[[(2S)-2-[[(2S)-2-Amino-3-methoxypropanoyl]amino]-2-(4-methoxyphenyl)acetyl]amino]-2,2-difluoro-3-hydroxy-5-methyl-N-(2,2,2-trifluoroethyl)hexanamide

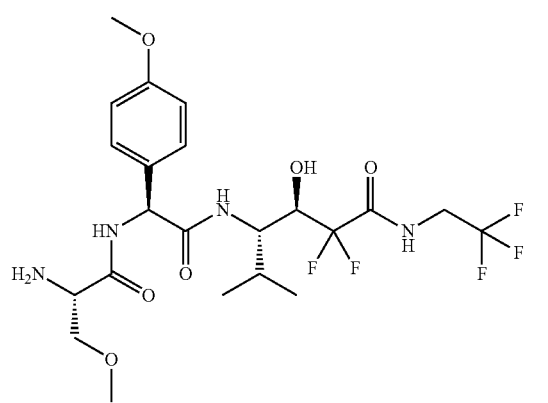 [SMILES: COC[C@H](N)C(=O)N[C@H](C(=O)N[C@@H](C(C)C)[C@@H](O)C(F)(F)C(=O)NCC(F)(F)F)c1ccc(OC)cc1]

was prepared as hydrochloride in analogy to Intermediate IIIc, but using in step A] (2S)-2-(tert-butoxycarbonylamino)-3-methoxy-propanoic acid instead of (2S)-3-(3-chlorophenyl)-2-[(2-methylpropan-2-yl)oxycarbonylamino]propanoic acid, as off white foam; MS: 543.3 (M+H)$^+$.

Intermediate IIIg tert-Butyl N-[[4-[(2S)-2-amino-3-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-3-oxopropyl]phenyl]methyl]carbamate

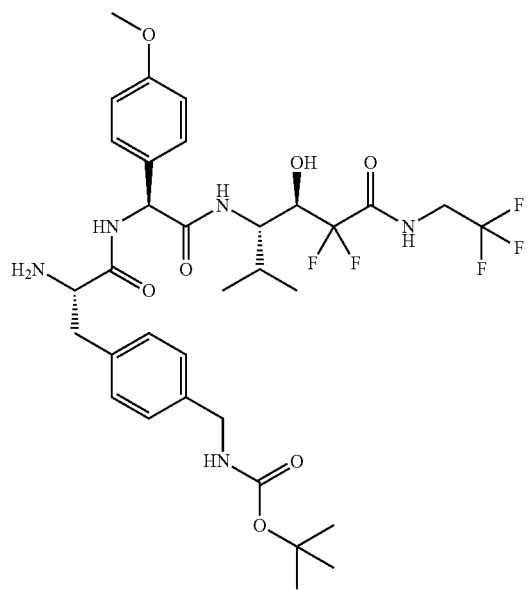 [SMILES: COc1ccc([C@H](NC(=O)[C@@H](N)Cc2ccc(CNC(=O)OC(C)(C)C)cc2)C(=O)N[C@@H](C(C)C)[C@@H](O)C(F)(F)C(=O)NCC(F)(F)F)cc1]

A] tert-Butyl N-[[4-[(2S)-3-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-2-(9H-fluoren-9-ylmethoxycarbonylamino)-3-oxopropyl]phenyl]methyl]carbamate

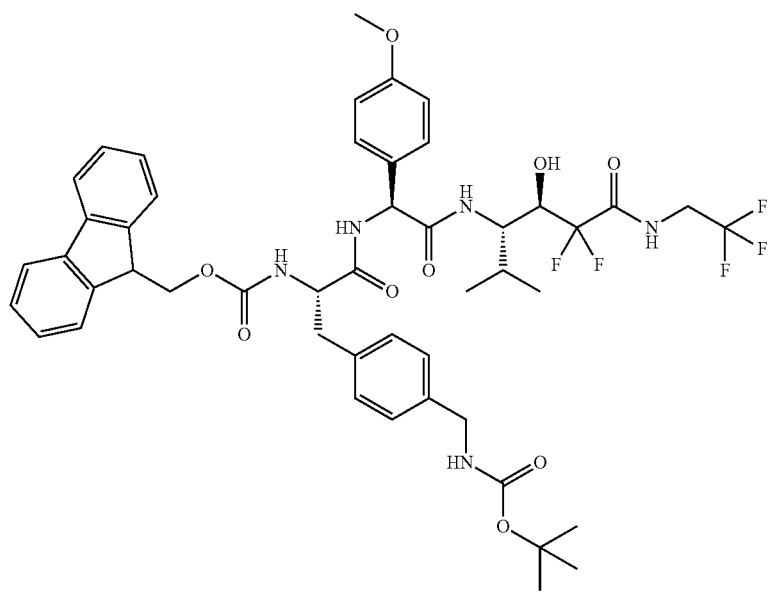 [SMILES: COc1ccc([C@H](NC(=O)[C@H](Cc2ccc(CNC(=O)OC(C)(C)C)cc2)NC(=O)OCC2c3ccccc3-c3ccccc32)C(=O)N[C@@H](C(C)C)[C@@H](O)C(F)(F)C(=O)NCC(F)(F)F)cc1]

To a solution of (3R,4S)-4-[[(2S)-2-amino-2-(4-methoxyphenyl)acetyl]amino]-2,2-difluoro-3-hydroxy-5-methyl-N-(2,2,2-trifluoroethyl)hexanamide hydrochloride (Intermediate IIb, 0.178 g, 0.372 mmol, Eq: 1), (2S)-3-[4-[(tert-butoxycarbonylamino)methyl]phenyl]-2-(9H-fluoren-9-ylmethoxycarbonylamino)propanoic acid (0.192 g, 0.372 mmol, Eq: 1) and HATU (0.170 g, 0.447 mmol, Eq: 1.2) in DMF (2 ml) cooled at 0° C., was added Huenig's base (0.195 ml, 1.12 mmol, Eq: 3) and the reaction mixture stirred at room temperature for 2 hours. The mixture was diluted with EtOAc, poured into $H_2O$ and extracted with EtOAc (2×10 ml). Combined organics were washed with brine, dried over $Na_2SO_4$, filtered and evaporated. The residue was purified by silica gel flash chromatography, eluting with a 10 to 100% EtOAc in heptane gradient to give the title compound as a light brown waxy solid; MS: 940.5 $(M+H)^+$.

B] tert-Butyl N-[[4-[(2S)-2-amino-3-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-3-oxopropyl]phenyl]methyl]carbamate

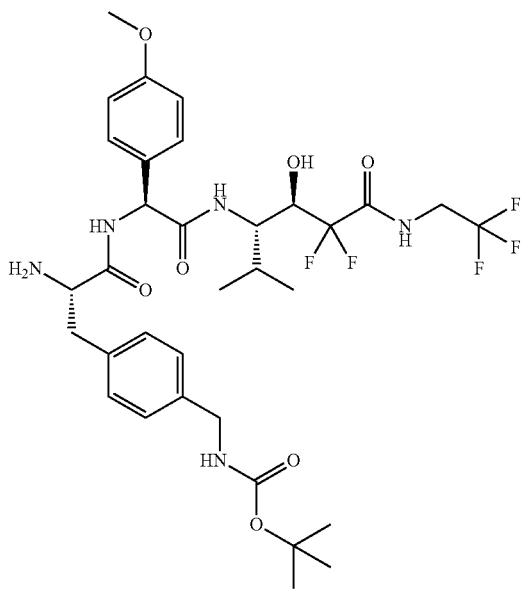 [SMILES: COc1ccc([C@H](NC(=O)[C@@H](N)Cc2ccc(CNC(=O)OC(C)(C)C)cc2)C(=O)N[C@@H](C(C)C)[C@@H](O)C(F)(F)C(=O)NCC(F)(F)F)cc1]

To a solution of tert-butyl N-[[4-[(2S)-3-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-2-(9H-fluoren-9-ylmethoxycarbonylamino)-3-oxopropyl]phenyl]methyl] carbamate (0.361 g, 0.384 mmol, Eq: 1) in DMF (3 ml) was added diethylamine (0.791 ml, 7.68 mmol, Eq: 20) and the reaction mixture was stirred at room temperature over night. The reaction mixture was concentrated in vacuo and the residue purified by silica gel flash chromatography, eluting with a to 100% EtOAc in heptane then from to 2 to 10% MeOH in EtOAc to give the title compound as a light yellow solid; MS: 718.4 (M+H)+.

Intermediate IIIh (3R,4S)-4-[[(2S)-2-[[(2S)-2-Amino-3-methoxypropanoyl]amino]-2-(4-methoxyphenyl)acetyl]amino]-N-[2-(1,1-dioxo-1,4-thiazinan-4-yl)ethyl]-2,2-difluoro-3-hydroxy-5-methylhexanamide

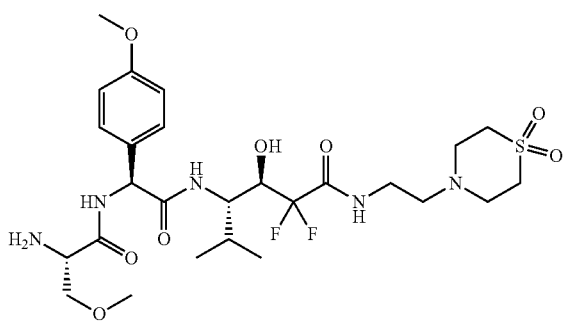 [SMILES: COC[C@H](N)C(=O)N[C@H](C(=O)N[C@@H](C(C)C)[C@@H](O)C(F)(F)C(=O)NCCN1CCS(=O)(=O)CC1)c1ccc(OC)cc1]

was prepared as hydrochloride in analogy to Intermediate IIIf, but using in step A] (3R,4S)-4-[[(2S)-2-amino-2-(4-methoxyphenyl)acetyl]amino]-N-[2-(1,1-dioxo-1,4-thiazinan-4-yl)ethyl]-2,2-difluoro-3-hydroxy-5-methyl-hexanamide (Intermediate IIe) instead of (3R,4S)-4-[[(2S)-2-amino-2-phenylacetyl]amino]-2,2-difluoro-3-hydroxy-5-methyl-N-(2,2,2-trifluoroethyl)-hexanamide hydrochloride (Intermediate IIa), as pink solid; MS: 622.8 (M+H)+.

Intermediate IVa (2S)-3-(3,4-Dichlorophenyl)-2-(pyridine-2-carbonylamino)propanoic acid

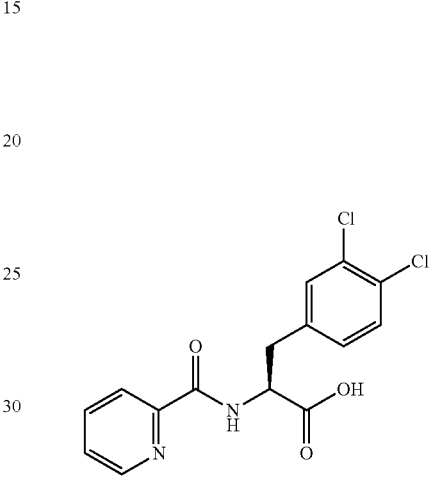

A] (2,5-Dioxopyrrolidin-1-yl) pyridine-2-carboxylate

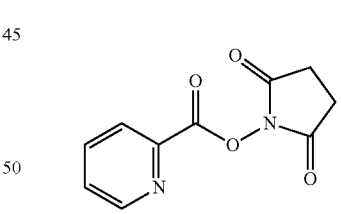

In a 50 mL flask, picolinic acid (500 mg, 4.06 mmol, Eq: 1) was combined with DCM (20 ml) to give a colorless solution. At 0° C., pyridine (964 mg, 985 µl, 12.2 mmol, Eq: 3), EDC (1.09 g, 5.69 mmol, Eq: 1.4), and 1-hydroxypyrrolidine-2,5-dione (608 mg, 5.28 mmol, Eq: 1.3) were subsequently added, the ice-bath was removed, and the reaction mixture was stirred at room temperature over night. The reaction mixture was then quenched with sat. NH4Cl sol. and extracted with DCM (2×20 ml). The organic layers were washed with sat NaHCO3, then with brine. The organic layers were combined, dried over Na2SO4, and concentrated in vacuo. The crude material was triturated with CH2Cl2/heptane to give 686 mg of the title compound as light brown solid; MS: 221.1 (M+H)+.

B] (2S)-3-(3,4-Dichlorophenyl)-2-(pyridine-2-carbonylamino)propanoic acid

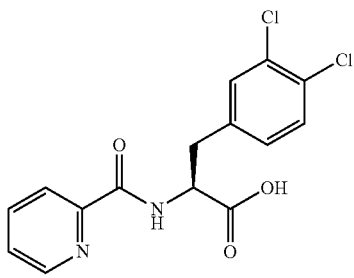 [SMILES: O=C(N[C@@H](Cc1ccc(Cl)c(Cl)c1)C(=O)O)c1ccccn1]

A solution of the above prepared 2,5-dioxopyrrolidin-1-yl picolinate (250 mg, 1.14 mmol, Eq: 1) in DME (4 ml) was added to a mixture of (S)-2-amino-3-(3,4-dichlorophenyl)propanoic acid (266 mg, 1.14 mmol, Eq: 1) in THF (2 ml) and sodium bicarbonate (95.4 mg, 1.14 mmol, Eq: 1) in water (4 ml). This mixture was stirred at rt for 3 h when LC-MS showed the reaction to be finished. The reaction mixture was poured into sat. $NH_4Cl$ sol. and extracted with AcOEt (2×). The organic layers were washed with brine, and the solvent was evaporated under vacuum. Purification by chromatography (silica gel, 10 g $CH_2Cl_2$/MeOH=8/1) delivered 309 mg of the title compound as white foam; MS: 339.1 $(M+H)^+$.

In close analogy, using the appropriate acidic building blocks, were prepared Intermediates IVb-IVk and IVm-IVt, respectively, as summarized in the following Table:

| Intermediate | Structure | Acid 1 | Acid 2 | Form Color MS |
|---|---|---|---|---|
| IVb | 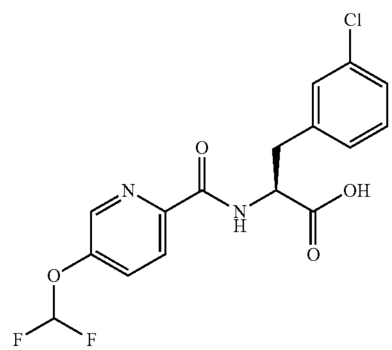 [SMILES: O=C(N[C@@H](Cc1cccc(Cl)c1)C(=O)O)c1ccc(OC(F)F)cn1] | | | Foam white 371.1 (M + H⁺) |
| IVc | 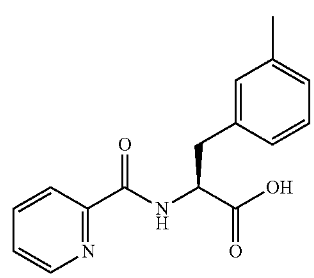 [SMILES: Cc1cccc(C[C@H](NC(=O)c2ccccn2)C(=O)O)c1] | | | Oil Colorless 285.2 (M + H⁺) |
| IVd | 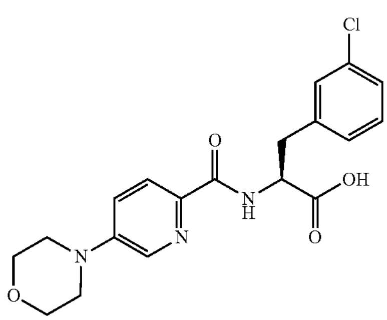 [SMILES: O=C(N[C@@H](Cc1cccc(Cl)c1)C(=O)O)c1ccc(N2CCOCC2)cn1] | | | Foam white 390.2 (M + H⁺) |

-continued

| Intermediate | Structure | Acid 1 | Acid 2 | Form Color MS |
|---|---|---|---|---|
| IVe | 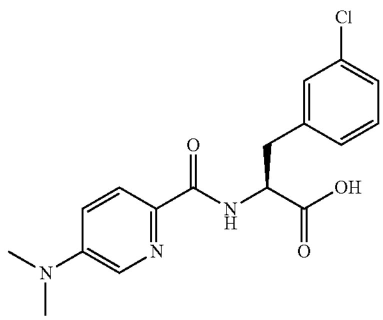 [SMILES: CN(C)c1ccc(C(=O)N[C@@H](Cc2cccc(Cl)c2)C(=O)O)nc1] | | | foam off-white 348.2 (M + H$^+$) |
| IVf | 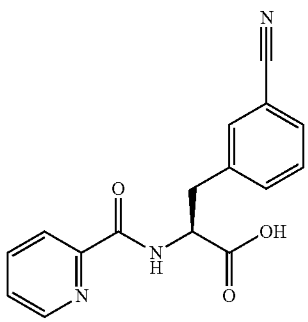 [SMILES: N#Cc1cccc(C[C@H](NC(=O)c2ccccn2)C(=O)O)c1] | | | oil light yellow 296.2 (M + H$^+$) |
| IVg | 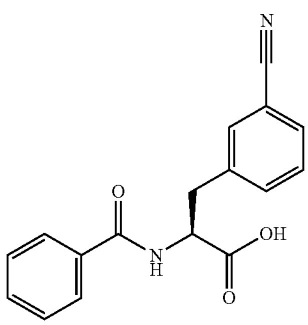 [SMILES: N#Cc1cccc(C[C@H](NC(=O)c2ccccc2)C(=O)O)c1] | | | solid white 295.2 (M + H$^+$) |
| IVh | 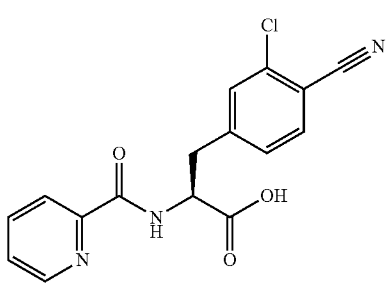 [SMILES: N#Cc1ccc(C[C@H](NC(=O)c2ccccn2)C(=O)O)cc1Cl] | | | semisolid white 330.2 (M + H$^+$) |
| IVi | 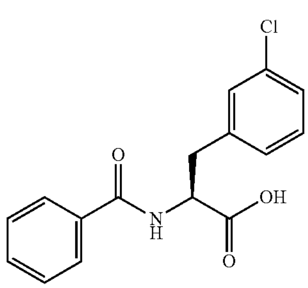 [SMILES: O=C(N[C@@H](Cc1cccc(Cl)c1)C(=O)O)c1ccccc1] | | | Foam colorless 304.1 (M + H$^+$) |

-continued

| Intermediate | Structure | Acid 1 | Acid 2 | Form Color MS |
|---|---|---|---|---|
| IVj | 3-chlorobenzoyl-3-chlorophenylalanine | 3-chlorobenzoic acid | 3-chloro-phenylalanine | solid white 338.1 (M + H⁺) |
| IVk | picolinoyl-3-chlorophenylalanine | picolinic acid | 3-chloro-phenylalanine | foam white 305.1 (M + H⁺) |
| IVm | N-(picolinoyl-glycyl)-3-chlorophenylalanine | N-picolinoyl glycine | 3-chloro-phenylalanine | oil colorless 362.2 (M + H⁺) |
| IVn | N-(picolinoyl-glycyl)-3-cyanophenylalanine | N-picolinoyl glycine | 3-cyano-phenylalanine | oil light yellow 353.1 (M + H⁺) |
| IVo | picolinoyl-3-chlorophenylalanine | picolinic acid | 3-chloro-phenylalanine | oil colorless 305.1 (M + H⁺) |

-continued

| Intermediate | Structure | Acid 1 | Acid 2 | Form Color MS |
|---|---|---|---|---|
| IVp | 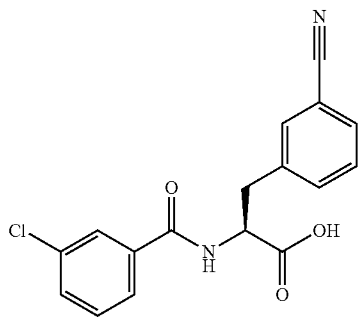 [SMILES: N#Cc1cccc(C[C@H](NC(=O)c2cccc(Cl)c2)C(=O)O)c1] | 3-chlorobenzoic acid | 3-cyano-L-phenylalanine | semisolid white 329.1 (M + H$^+$) |
| IVq | 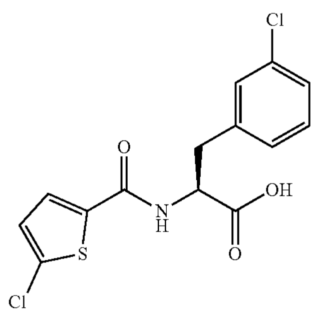 [SMILES: O=C(N[C@@H](Cc1cccc(Cl)c1)C(=O)O)c1ccc(Cl)s1] | 5-chlorothiophene-2-carboxylic acid | 3-chloro-L-phenylalanine | Foam white 344.0 (M + H$^+$) |
| IVr | 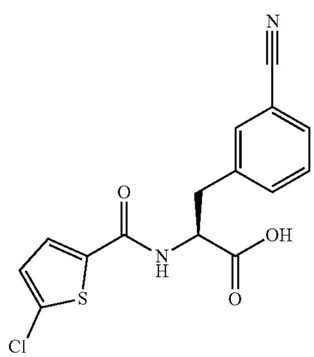 [SMILES: N#Cc1cccc(C[C@H](NC(=O)c2ccc(Cl)s2)C(=O)O)c1] | 5-chlorothiophene-2-carboxylic acid | 3-cyano-L-phenylalanine | Foam white 335.0 (M + H$^+$) |
| IVs | 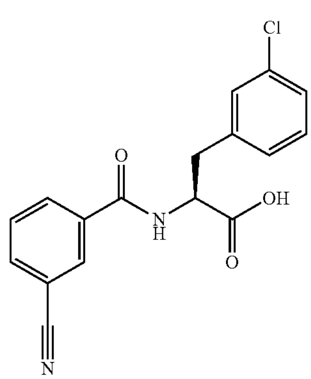 [SMILES: N#Cc1cccc(C(=O)N[C@@H](Cc2cccc(Cl)c2)C(=O)O)c1] | 3-cyanobenzoic acid | 3-chloro-L-phenylalanine | solid white 329.2 (M + H$^+$) |

-continued

| Intermediate | Structure | Acid 1 | Acid 2 | Form Color MS |
|---|---|---|---|---|
| IVt | 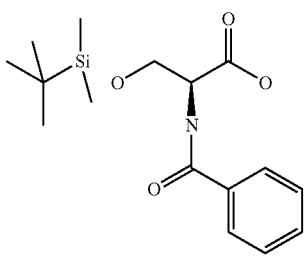 | 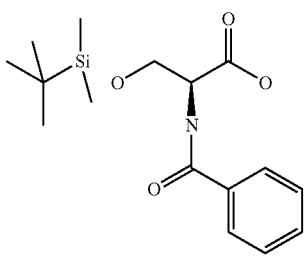 | 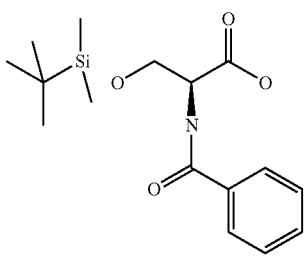 | solid wite 372.2 (M + H⁺) |

Spot checking the stereochemical integrity by chiral HPLC (Chiralpak AD-H) with intermediate IVi and IVj confirmed that the reaction sequence had proceeded under these mild reaction conditions without racemisation.

Intermediate IVl (rac)-2-Benzamido-3-(3-chlorophenyl)propanoic acid

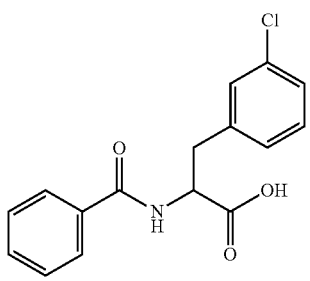 [SMILES: O=C(NC(Cc1cccc(Cl)c1)C(=O)O)c1ccccc1]

In a 50 mL pear-shaped flask, (S)-2-amino-3-(3-chlorophenyl)propanoic acid (599 mg, 3 mmol, Eq: 1) and potassium carbonate (1.18 g, 8.55 mmol, Eq: 2.85) were combined with water (10 ml) to give a colorless solution; benzoyl chloride (633 mg, 522 µl, 4.5 mmol, Eq: 1.5) was added via syringe and the resulting suspension stirred at ambient temperature over night; 2M HCl was added to adjust the pH to ~2, the mixture was extracted twice with AcOEt, washed with a small amount of brine, dried over Na₂SO₄, and evaporate to dryness; flash chromatography SiO2 (50 g, CH₂Cl₂/3% AcOH/5% MeOH), followed by crystallisation from AcOEt/heptane, delivered 358 mg of the title compound as white solid; MS: 304.1 (M+H⁺); chiral HPLC (Chiralpak AD-H) revealed that the product had racemised to ~100% under these reaction conditions!

Intermediate IVu (2S)-2-Benzamido-3-[tert-butyl(dimethyl)silyl]oxy-propanoic acid A] (2S)-2-Benzamido-3-hydroxypropanoic acid

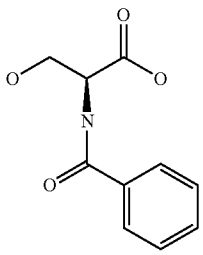

In a 100 mL pear-shaped flask, (S)-2-amino-3-hydroxypropanoic acid (631 mg, 6 mmol, Eq: 1) and potassium carbonate (2.36 g, 17.1 mmol, Eq: 2.85) were combined with water (20 ml) to give a colorless solution; benzoyl chloride (1.27 g, 1.04 ml, 9 mmol, Eq: 1.5) was added via syringe, and the resulting suspension stirred at ambient temperature over night; 2M HCl was added (~15 ml, solid precipitated) to adjust the pH to ~3.5, the mixture was extracted twice with AcOEt, dried over Na₂SO₄, and evaporated to dryness; the crude product was purified by flash chromatography (SiO₂, CH₂Cl₂/5% AcOH/10% MeOH) to yield, after scrupulous drying, 403 mg of the title compound as white crystals; MS: 210.1 (M+H)⁺.

B] (2S)-2-Benzamido-3-[tert-butyl(dimethyl)silyl]oxypropanoic acid

A] (2,5-Dioxopyrrolidin-1-yl) 1-(3-chlorophenyl)cyclopropane-1-carboxylate

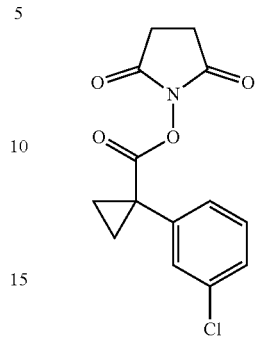

In a 100 mL flask, 1-(3-chlorophenyl)cyclopropanecarboxylic acid (0.50 g, 2.54 mmol, Eq: 1) was combined with DCM (15 ml) to give a colorless solution. At 0° C., pyridine (603 mg, 617 µl, 7.63 mmol, Eq: 3), N1-((ethylimino)methylene)-N3,N3-dimethylpropane-1,3-diamine hydrochloride (634 mg, 3.31 mmol, Eq: 1.3), and 1-hydroxypyrrolidine-2,5-dione (380 mg, 3.31 mmol, Eq: 1.3) were added, the ice-bath was removed, and the reaction allowed to proceed at RT for 2 hours. The reaction mixture was then quenched with sat. NH$_4$Cl sol. and extracted with DCM (2×, pH ~4.5). The organic layers were washed with sat. NaHCO$_3$ (pH ~8), combined, dried over Na$_2$SO$_4$, and concentrated in vacuo; after careful HV-drying, the crude material was crystallized from AcOEt/heptane to give 513 mg of the title compound as white solid.

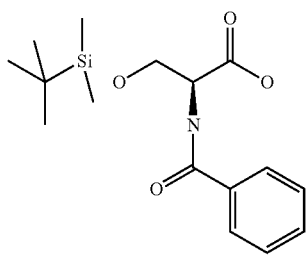

In a 150 mL pear-shaped flask, the above prepared (S)-2-benzamido-3-hydroxypropanoic acid (399 mg, 1.91 mmol, Eq: 1) and 1H-imidazole (286 mg, 4.2 mmol, Eq: 2.2) were combined with DMF (2 ml) to give an off-white solution; tert-butylchlorodimethylsilane (316 mg, 2.1 mmol, Eq: 1.1) was added and the silylation allowed to proceed over night; after 18 h, the reaction mixture was poured onto brine, extracted twice with AcOEt (pH ~7), washed with brine, dried over Na$_2$SO$_4$, and evaporated to dryness; flash chromatography (SiO2, 20 g, AcOEt/5% MeOH) afforded 388 mg of the title compound as white crystals; MS: 324.2 (M+H)$^+$.

B] (2S)-2-[[1-(3-Chlorophenyl)cyclopropanecarbonyl]amino]-3-hydroxypropanoic acid

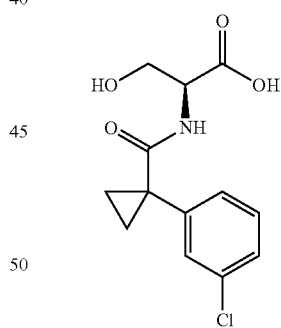

Intermediate IVv

(2S)-3-[tert-Butyl(dimethyl)silyl]oxy-2-[[1-(3-chlorophenyl)cyclopropanecarbonyl]-amino]propanoic acid

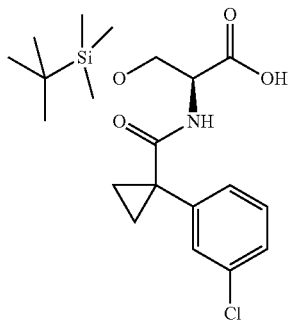

A solution of the above synthesized 2,5-dioxopyrrolidin-1-yl 1-(3-chlorophenyl)-cyclopropanecarboxylate (0.25 g, 851 µmol, Eq: 1) in DME (7 ml) was added to a mixture of (S)-2-amino-3-hydroxypropanoic acid (=serine, 89.5 mg, 851 µmol, Eq: 1) in THF (3.5 ml) and sodium bicarbonate (71.5 mg, 851 µmol, Eq: 1) in water (7 ml), and the mixture was vigorously stirred at RT for 4 hours. It was then poured into sat. NH$_4$Cl sol and extracted with AcOEt (2×). The organic layers were washed with brine and the solvent was evaporated under vacuum. The aqueous layer was back-extracted with CH$_2$Cl$_2$/MeOH=9/1 (4×40 mL). The organic layers were combined, dried over Na$_2$SO$_4$ and concentrated in vacuo. The crude material was purified by flash chromatography (silica gel, 20 g, CH₂Cl₂/EtOAc/MeOH 95:5:5) to yield 192 mg of the title compound as light brown oil; MS: 284.1 (M+H)⁺.

C] (2S)-3-[tert-Butyl(dimethyl)silyl]oxy-2-[[1-(3-chlorophenyl)cyclopropanecarbonyl]-amino]propanoic acid

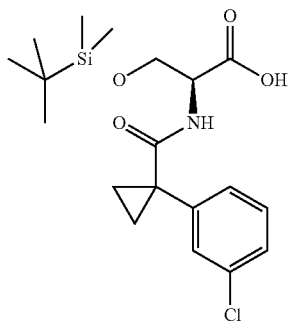

In a 10 mL round-bottomed flask, the above prepared (S)-2-(1-(3-chlorophenyl)-cyclopropanecarboxamido)-3-hydroxypropanoic acid (0.218 g, 768 μmol, Eq: 1) and imidazole (115 mg, 1.69 mmol, Eq: 2.2) were combined with DMF (3 ml) to give an off-white suspension; tert-butylchlorodimethylsilane (127 mg, 845 μmol, Eq: 1.1) was added and the reaction stirred at RT overnight. The reaction mixture was poured into brine and extracted with EtOAc. The organic layers were combined, washed with brine, dried over Na₂SO₄ and concentrated in vacuo. The crude material was purified by flash chromatography (silica gel, 20 g, 5% MeOH in EtOAc) to provide 94 mg of the title compound as colorless oil; MS: 398.2 (M+H)⁺.

Intermediate IVw (2S)-3-[tert-Butyl(dimethyl)silyl]oxy-2-[[1-(3-chlorophenyl)cyclopropanecarbonyl]-amino]butanoic acid

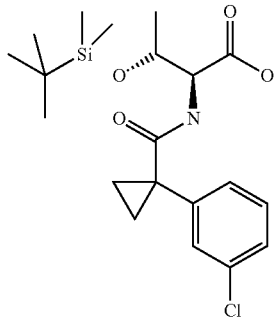

Was prepared in analogy to intermediate IVv, but using in step B] (2S,3R)-2-amino-3-hydroxybutanoic acid (=threonine) instead of of (S)-2-amino-3-hydroxypropanoic acid (=serine), as light yellow oil; MS: 412.2 (M+H)⁺.

Intermediate IVx (2S)-2-[[1-(3-Chlorophenyl)cyclopropanecarbonyl] amino]propanoic acid

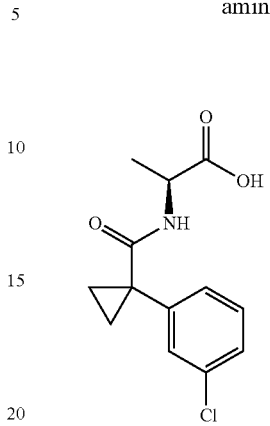

A] (2,5-Dioxopyrrolidin-1-yl) 1-(3-chlorophenyl)cyclopropane-1-carboxylate

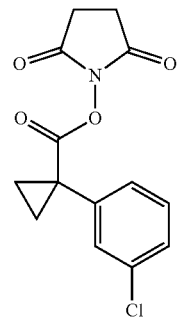 [SMILES: O=C1CCC(=O)N1OC(=O)C1(c2cccc(Cl)c2)CC1]

In a 100 mL flask, 1-(3-chlorophenyl)cyclopropanecarboxylic acid (0.5 g, 2.54 mmol, Eq: 1) was combined with DCM (15 ml) to give a colorless solution. At 0° C., pyridine (603 mg, 617 μl, 7.63 mmol, Eq: 3), N1-((ethylimino)methylene)-N3,N3-dimethylpropane-1,3-diamine hydrochloride (634 mg, 3.31 mmol, Eq: 1.3), and 1-hydroxypyrrolidine-2,5-dione (380 mg, 3.31 mmol, Eq: 1.3) were subsequently added. The ice-bath was removed and the reaction mixture was stirred at rt over night. It was then quenched with sat NH₄Cl sol. and extracted with CH₂Cl₂ (2×, pH ~4.5). The organic layers were washed with sat. NaHCO₃ (pH ~8), combined, dried over Na₂SO₄, and concentrated in vacuo; after careful HV-drying, the crude material was crystallized from AcOEt/heptane to yield 486 mg of the title product as white crystals; CI-MS 311.1 (M+NH₄)⁺.

B] (2S)-2-[[1-(3-Chlorophenyl)cyclopropanecarbonyl]amino]propanoic acid

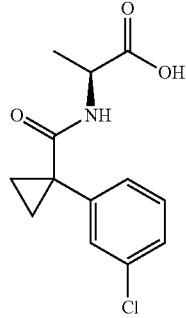 [SMILES: C[C@H](NC(=O)C1(c2cccc(Cl)c2)CC1)C(=O)O]

A solution of the above prepared 2,5-dioxopyrrolidin-1-yl 1-(3-chlorophenyl)-cyclopropanecarboxylate (0.200 g, 681 µmol, Eq: 1) in DME (6 ml) was added to a mixture of (S)-2-aminopropanoic acid (60.7 mg, 681 µmol, Eq: 1) in THF (3 ml) and sodium bicarbonate (57.2 mg, 681 µmol, Eq: 1) in water (6 ml), and the reaction allowed to proceed at RT for 4 hours. The mixture was poured into sat. NH$_4$Cl sol. and extracted with AcOEt (2×). The organic layers were washed with brine, dried over Na$_2$SO$_4$, and the solvent was evaporated under vacuum. The aqueous layer was back-extracted with CH$_2$Cl$_2$/MeOH=9/1 (4×40 ml). The organic layers were combined, dried over Na$_2$SO$_4$, and concentrated in vacuo. Purification by flash chromatography (silica gel, 20 g, 5% to 10% MeOH in CH$_2$Cl$_2$) eventually yielded 94 mg of the title compound as colorless oil; MS: 268.1 (M+H)$^+$.

Intermediate IVy (2S)-2-[(2,5-Dichlorobenzoyl)amino]propanoic acid

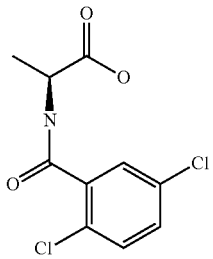 [SMILES: C[C@H](NC(=O)c1cc(Cl)ccc1Cl)C(=O)O]

Was prepared in analogy to intermediate IVx, but starting the reaction sequence with 2,5-dichlorobenzoic acid instead of 1-(3-chlorophenyl)cyclopropanecarboxylic acid, as white solid; MS: 262.1 (M+H)$^+$.

Intermediate IVz (2S)-2-[(3-Chlorobenzoyl)amino]propanoic acid

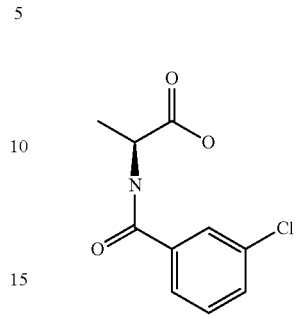

Was prepared in analogy to intermediate IVx, but starting the reaction sequence with 3-chlorobenzoic acid instead of 1-(3-chlorophenyl)cyclopropanecarboxylic acid, as white solid; MS: 228.1 (M+H)$^+$.

Intermediate IVaa (2S)-2-[[4-(2-tert-Butoxy-2-oxo-ethoxy)benzoyl]amino]-3-(3-chlorophenyl)propanoic acid

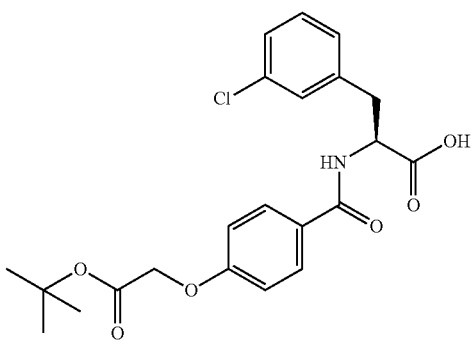 [SMILES: CC(C)(C)OC(=O)COc1ccc(C(=O)N[C@@H](Cc2cccc(Cl)c2)C(=O)O)cc1]

A] (2,5-Dioxopyrrolidin-1-yl) 4-[2-[(2-methylpropan-2-yl)oxy]-2-oxoethoxy]benzoate

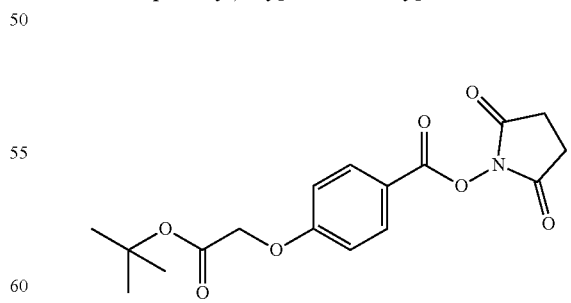

In analogy to the procedure described for the preparation of intermediate IVa [A], 4-[2-[(2-methylpropan-2-yl)oxy]-2-oxoethoxy]benzoic acid (US2011/0207704) has been reacted with pyridine, EDC and 1-hydroxypyrrolidine-2,5-dione to give the title compound as white solid.

B] (2S)-2-[[4-(2-Tert-butoxy-2-oxo-ethoxy)benzoyl]amino]-3-(3-chlorophenyl)propanoic acid

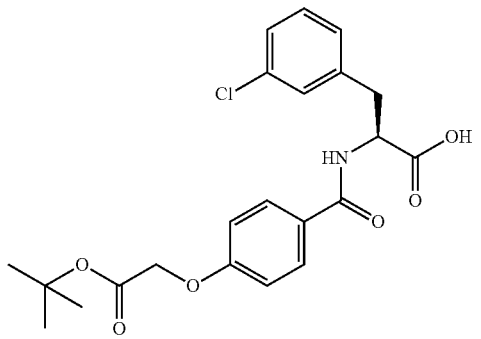 [SMILES: CC(C)(C)OC(=O)COc1ccc(C(=O)N[C@@H](Cc2cccc(Cl)c2)C(=O)O)cc1]

In analogy to the procedure described for the preparation of intermediate IVa [B], the above prepared (2,5-dioxopyrrolidin-1-yl) 4-[2-[(2-methylpropan-2-yl)oxy]-2-oxoethoxy]benzoate has been reacted with (2S)-2-amino-3-(3-chlorophenyl)propanoic acid in presence of sodium bicarbonate to give the title compound as off-white foam; MS: 434.3 (M+H)$^+$.

In close analogy to Intermediate IVa, using the appropriate acidic building blocks, were prepared Intermediates IVbb-IVdd and IVgg-IVhh, respectively, as summarized in the following Table:

| Intermediate | Structure | Acid 1 | Acid 2 | Form Color MS |
|---|---|---|---|---|
| IVbb | ![structure] | ![structure] | ![structure] | solid white 322.0 (M + H)+ |
| IVcc | ![structure] | ![structure] | ![structure] | oil colorless 287.1 (M + H)+ |
| IVdd | ![structure] | ![structure] | ![structure] | solid white 356.0 (M + H)+ |

-continued

| Intermediate | Structure | Acid 1 | Acid 2 | Form Color MS |
|---|---|---|---|---|
| IVgg | (structure) | (structure) | (structure) | foam white 320.1 (M + H)+ |
| IVhh | (structure) | (structure) | (structure) | semisolid light yellow 313.0 (M + H)+ |

Intermediate IVee (2S)-2-[(3-Chlorobenzoyl)amino]-3-(4-chloro-3-cyanophenyl)propanoic acid

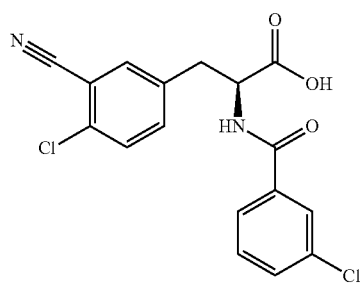 [SMILES: N#Cc1cc(C[C@H](NC(=O)c2cccc(Cl)c2)C(=O)O)ccc1Cl]

A] Methyl (2S)-2-[(3-chlorobenzoyl)amino]-3-(4-chloro-3-cyanophenyl)propanoate

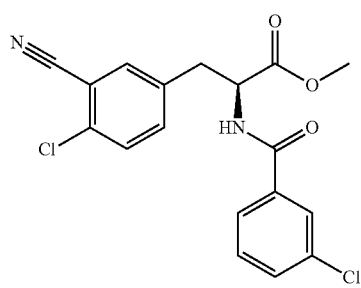 [SMILES: COC(=O)[C@H](Cc1ccc(Cl)c(C#N)c1)NC(=O)c1cccc(Cl)c1]

In a 10 mL round-bottomed flask, commercially available (S)-methyl 2-amino-3-(4-chloro-3-cyanophenyl)propanoate hydrochloride (200 mg, 727 µmol, Eq: 1) was combined with DCM (6 ml) to give a light brown suspension; N,N-diisopropylethylamine (282 mg, 403 µl, 2.18 mmol, Eq: 3) was added and the solution was cooled to ~−10° C. 3-Chlorobenzoyl chloride (127 mg, 727 µmol, Eq: 1) was added and the reaction allowed to proceed for 30 min when LC-MS indicated the absence of starting material. The reaction mixture was poured into ice and sat. NH$_4$Cl and extracted with DCM (2×20 ml). The organic layers were washed with brine, dried (Na$_2$SO4) and evaporated. Purification by flash chromatography (silica gel, 20 g, 20% to 60% EtOAc in heptane) yielded 269 mg of the title compound as white semisolid; MS: 377.1 (M+H)$^+$.

B] (2S)-2-[(3-Chlorobenzoyl)amino]-3-(4-chloro-3-cyanophenyl)propanoic acid

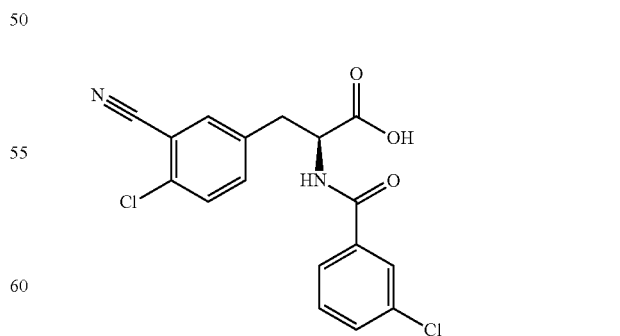

In a 25 mL round-bottomed flask, the above prepared (S)-methyl 3-(4-chloro-3-cyanophenyl)-2-(3-chlorobenzamido)propanoate (264 mg, 700 µmol, Eq: 1) was combined with THF (3 ml) and MeOH (1.5 ml) to give a colorless solution. LiOH 1M in H$_2$O (770 µl, 770 µmol, Eq: 1.1) was added at 0° C. and the reaction was stirred at 0° C. for 5 h when LC-MS showed the reaction to be finished. The mixture was quenched with dil. KHSO$_4$ sol., and extracted with AcOEt (2×); the organic layers were washed with brine, dried (Na$_2$SO$_4$) and concentrated in vacuo. Trituration with TBME/heptane afforded the title acid as white semisolid; MS: 363.0 (M+H)$^+$.

Intermediate IVff (2S)-2-[[2-(3-Chlorophenyl)-2,2-difluoroacetyl]amino]propanoic acid

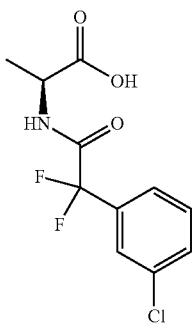 [SMILES: C[C@H](NC(=O)C(F)(F)c1cccc(Cl)c1)C(=O)O]

A] Benzyl (2S)-2-[[2-(3-chlorophenyl)-2,2-difluoroacetyl]amino]propanoate

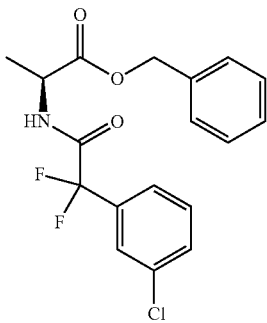 [SMILES: C[C@H](NC(=O)C(F)(F)c1cccc(Cl)c1)C(=O)OCc1ccccc1]

To a mixture of 2-(3-chlorophenyl)-2,2-difluoroacetic acid (207 mg, 1 mmol, Eq: 1) and (S)-benzyl 2-aminopropanoate hydrochloride (216 mg, 1 mmol, Eq: 1) in DMF (8 ml) were added at ~−10° C. N,N-diisopropylethylamine (646 mg, 873 µl, 5 mmol, Eq: 5) and 2-(3H-[1,2,3]triazolo[4,5-b]pyridin-3-yl)-1,1,3,3-tetramethylisouronium hexafluorophosphate (V)=HATU (456 mg, 1.2 mmol, Eq: 1.2); the reaction mixture was stirred and slowly warmed within 2 h to RT and kept for another 2 h at this temperature; LC-MS indicated only traces of desired product and a lot of starting acid; obviously, the amine competed successfully with the acid for HATU! Therefore, another 2 eq. of HATU and amine were added and the mixture kept over night at ambient temperature; the reaction mixture was quenched with cold 0.1 M HCl and extracted with EtOAc (2×50 mL). The organic layers were washed with brine, combined, dried over Na$_2$SO$_4$, and concentrated in vacuo; the crude material was purified by flash chromatography (silica gel, 20 g, 40% EtOAc in heptane) to afford 331 mg of the title compound as white solid; MS: 366.1 (M−H)$^−$; by chiral HPLC, the other enantiomer was not detectable!

B] (2S)-2-[[2-(3-chlorophenyl)-2,2-difluoroacetyl]amino]propanoic acid

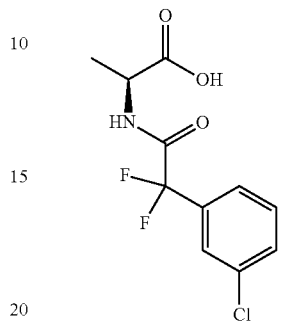

In a 50 mL pear-shaped flask, the above prepared (S)-benzyl 2-(2-(3-chlorophenyl)-2,2-difluoroacetamido)-propanoate (324 mg, 881 µmol, Eq: 1) was combined with AcOEt (8.81 ml) to give a colorless solution; Palladium on carbon (10%, 46.9 mg, 44 µmol, Eq: 0.05) was added and hydrogenation allowed to proceed at ambient temperature (balloon of H$_2$); TLC after 2 h at ambient temperature showed the reaction to be finished; the reaction mixture was filtered over a pad of Celite, generously washed with AcOEt, and the filtrate evaporated to dryness; 257 mg of the title acid was obtained after careful HV-drying as off-white solid; MS: 276.1 (M−H)$^−$.

Intermediate IVii (2S)-3-[tert-Butyl(dimethyl)silyl]oxy-2-[[2-(3-chlorophenyl)-2,2-difluoroacetyl]amino]propanoic acid

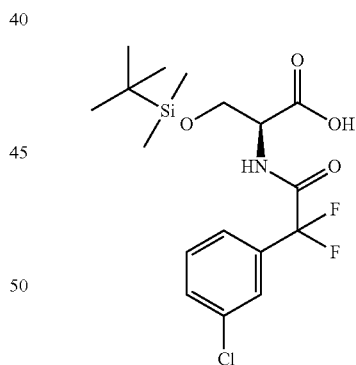

A] Benzyl (2S)-2-amino-3-[tert-butyl(dimethyl)silyl]oxypropanoate

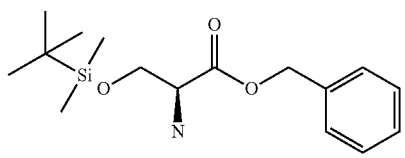

DBU (1.31 g, 1.3 ml, 8.63 mmol, Eq: 2) was added to a suspension of (S)-benzyl 2-amino-3-hydroxypropanoate hydrochloride (1 g, 4.32 mmol, Eq: 1) and tert-butylchlorodimethylsilane (683 mg, 4.53 mmol, Eq: 1.05) in Acetonitrile (20 ml) at 0° C. and the homogeneous mixture was stirred at RT for 3 hours when LC-MS showed the reaction to be finished. The mixture was poured into 20 mL sat. NaHCO$_3$ sol. and extracted with EtOAc (2×50 mL). The organic layers were combined, washed with brine, dried over Na$_2$SO$_4$ and concentrated in vacuo. Purification by flash chromatography (silica gel, 50 g, 30% to 80% EtOAc in heptane) yielded 0.844 g of the title compound as colorless oil; MS: 310.2 (M+H)$^+$.

B] Benzyl (2S)-3-[tert-butyl(dimethyl)silyl]oxy-2-[[2-(3-chlorophenyl)-2,2-difluoroacetyl]amino]propanoate

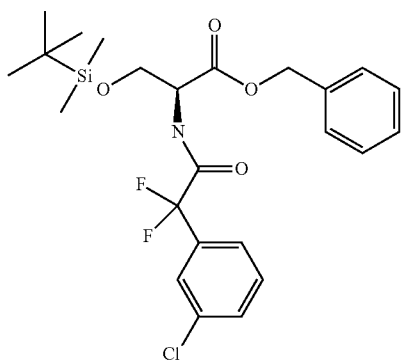

Step 1: In a 10 mL round-bottomed flask, 2-(3-chlorophenyl)-2,2-difluoroacetic acid (618 mg, 2.99 mmol, Eq: 1.1) was combined with CH2Cl2 (10 ml) and 2 drops of DMF to give a colorless solution; oxalyl chloride (759 mg, 523 µl, 5.98 mmol, Eq: 2.2) was added under ice-bath cooling and the reaction mixture was stirred for 5 min at 0° C. The ice-bath was removed and the reaction allowed to continue at rt for 2 hours. The mixture was concentrated under exclusion of moisture and oxygen and then dried for a short period of time on hv and purged with argon.

Step 2: This crude acid chloride was combined with CH2Cl2 (20 ml) to give a light yellow solution. N,N-diisopropylethylamine (1.76 g, 2.37 ml, 13.6 mmol, Eq: 5) and the above prepared (S)-benzyl 2-amino-3-((tert-butyldimethylsilyl)oxy)propanoate (0.841 g, 2.72 mmol, Eq: 1) were added at 0° C. and the reaction allowed to proceed for 30 min., when LC-MS indicated the reaction to be finished. The mixture was poured into sat. NH$_4$Cl sol.+ice and extracted with DCM (2×). The organic layers were washed with brine, combined, dried over Na$_2$SO$_4$ and concentrated in vacuo. The crude material was purified by flash chromatography (silica gel, 50 g, 0% to 50% EtOAc in heptane) to afford 1.21 g of the title amide as yellow oil; MS: 498.2 (M+H)$^+$.

C] (2S)-3-[tert-Butyl(dimethyl)silyl]oxy-2-[[2-(3-chlorophenyl)-2,2-difluoroacetyl]amino]propanoic acid

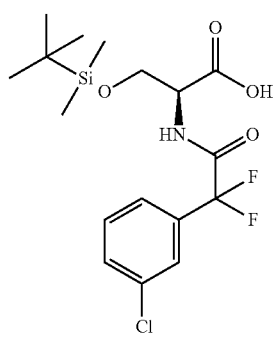

In a 50 mL pear-shaped flask, the above prepared (S)-benzyl 3-((tert-butyldimethylsilyl)oxy)-2-(2-(3-chlorophenyl)-2,2-difluoroacetamido)propanoate (604 mg, 1.21 mmol, Eq: 1) was combined with ethyl acetate (12 ml) to give a colorless solution; Pd—C 10% (40 mg, 37.6 µmol, Eq: 0.031) was added and hydrogenation allowed to proceed at ambient temperature (balloon of H2). TLC after 3 h showed the reaction to be complete. The reaction mixture was filtered through a pad of Celite, washed with AcOEt and evaporated to dryness to leave 525 mg of the title acid, containing traces of ethyl acetate, but otherwise pure; MS: 408.2 (M+H)$^+$.

Intermediate IVii (2S)-3-[tert-Butyl(dimethyl)silyl]oxy-2-[[2-(3-fluorophenyl)-2,2-difluoroacetyl]amino]propanoic acid

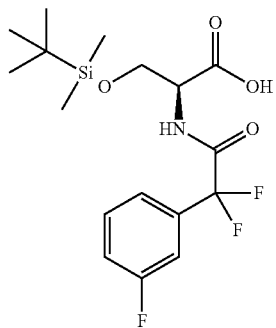

was prepared in analogy to Intermediate IVii, but using in step B] 2-(3-fluorophenyl)-2,2-difluoroacetic acid instead of 2-(3-chlorophenyl)-2,2-difluoroacetic acid, as colorless oil; MS: 392.2 (M+H)$^+$.

Example 1

N-[(2S)-3-(3-chlorophenyl)-1-[[(1S)-2-[[(3S)-5,5-difluoro-2-methyl-4,6-dioxo-6-(2,2,2-trifluoroethyl-amino)hexan-3-yl]amino]-2-oxo-1-phenylethyl]amino]-1-oxopropan-2-yl]pyridine-4-carboxamide

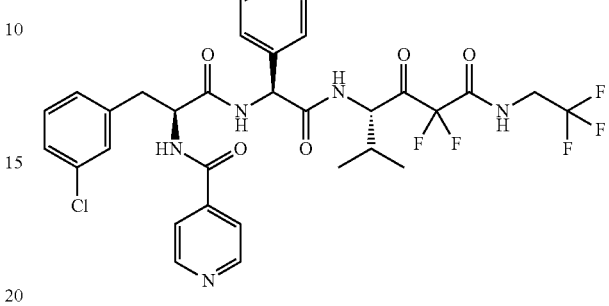

A] N-[(2S)-3-(3-Chlorophenyl)-1-[[(1S)-2-[[(3S,4R)-5,5-difluoro-4-hydroxy-2-methyl-6-oxo-6-(2,2,2-trifluoroethylamino)hexan-3-yl]amino]-2-oxo-1-phenylethyl]amino]-1-oxopropan-2-yl]pyridine-4-carboxamide

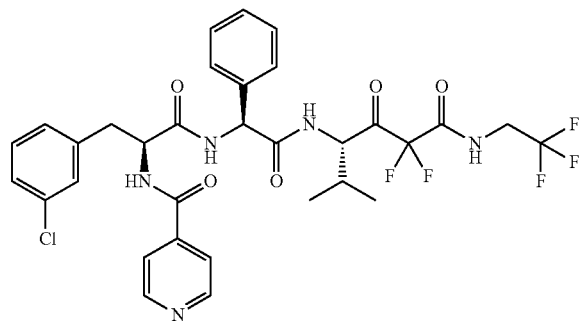 [SMILES: CC(C)[C@H](NC(=O)[C@@H](NC(=O)[C@H](Cc1cccc(Cl)c1)NC(=O)c1ccncc1)c1ccccc1)C(=O)C(F)(F)C(=O)NCC(F)(F)F]

In a 50 mL pear-shaped flask, (4S)-4-[[(2S)-2-[[(2S)-2-amino-3-(3-chlorophenyl)propanoyl]amino]-2-phenylacetyl]amino]-2,2-difluoro-3-hydroxy-5-methyl-N-(2,2,2-trifluoroethyl)hexanamide hydrochloride (Intermediate IIIa, 0.098 g, 140 µmol, Eq: 1) was combined with DMF (3 ml) to give a light yellow solution; pyridine-4-carboxylic acid (17.3 mg, 140 µmol, Eq: 1), HATU (107 mg, 280 µmol, Eq: 2) and Hunig's base (45.3 mg, 61.2 µl, 350 µmol, Eq: 2.5) were successively added at 0° C. and the reaction mixture was stirred for 3 hours at RT. The reaction mixture was quenched with sat. NaHCO₃ and extracted with EtOAc (2×). The organic layers were washed with 1N KHSO₄ and brine, combined, dried over Na₂SO₄, and concentrated in vacuo. The crude material was purified by flash chromatography (silica gel, 10 g, 30% to 80% EtOAc in heptane) to afford 40 mg of the desired product as white solid; MS: 698.2 (M+H⁺).

B] N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyridine-4-carboxamide

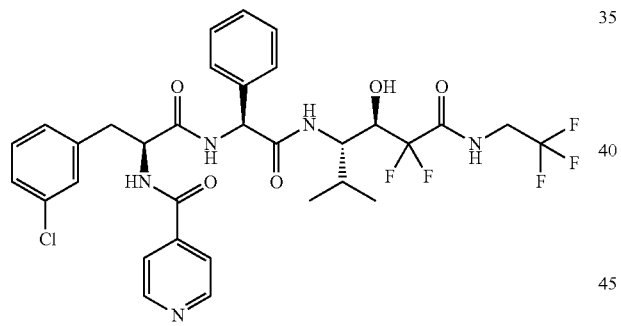

In a 10 mL round-bottomed flask, the above prepared N-[(2S)-3-(3-chlorophenyl)-1-[[(1S)-2-[[(3S,4R)-5,5-difluoro-4-hydroxy-2-methyl-6-oxo-6-(2,2,2-trifluoroethylamino)hexan-3-yl]amino]-2-oxo-1-phenylethyl]amino]-1-oxopropan-2-yl]pyridine-4-carboxamide (0.040 g, 57.3 mol, Eq: 1) was combined with DCM (2 ml) to give a colorless solution. Dess-Martin periodinane 15% in dichloromethane (243 mg, 178 µl, 86 µmol, Eq: 1.5) was added at 0° C. and the reaction mixture was stirred at RT for 2 hours. The reaction mixture was treated with sat. NaHCO₃ and extracted with DCM (2×20 ml). The organic layers were washed with brine, dried over Na₂SO₄ and evaporated i. v. The crude material was purified by flash chromatography (basic alumina, 10 g, 50% to 100% EtOAc) to yield 15 mg of the desired product as colorless oil; MS: 696.2 (M+H⁺).

Example 2

N-[(2S)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyridine-2-carboxamide

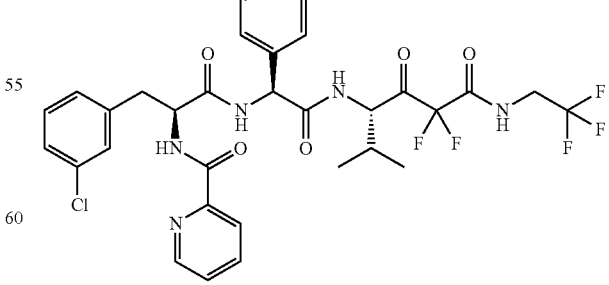

was prepared in analogy to example 1, but using in step A] pyridine-2-carboxylic acid instead of pyridine-4-carboxylic acid, as white foam; MS: 696.2 (M+H⁺).

Example 3

N-[(2S)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyrazine-2-carboxamide

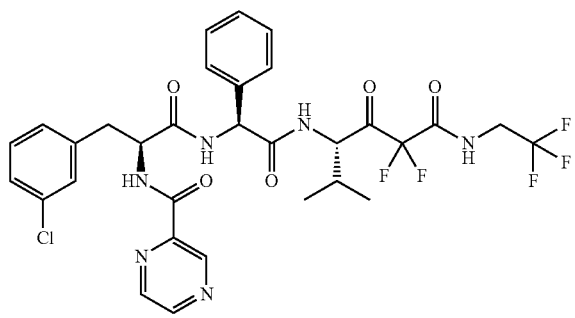 [SMILES: CC(C)[C@H](NC(=O)[C@@H](NC(=O)[C@H](Cc1cccc(Cl)c1)NC(=O)c1cnccn1)c1ccccc1)C(=O)C(F)(F)C(=O)NCC(F)(F)F]

was prepared in analogy to example 1, but using in step A] pyrazine-2-carboxylic acid instead of pyridine-4-carboxylic acid, as white solid; MS: 697.3 (M+H⁺); it contained some diastereomers as impurity.

Example 4

N-[(2S)-3-(3-hlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyrimidine-5-carboxamide

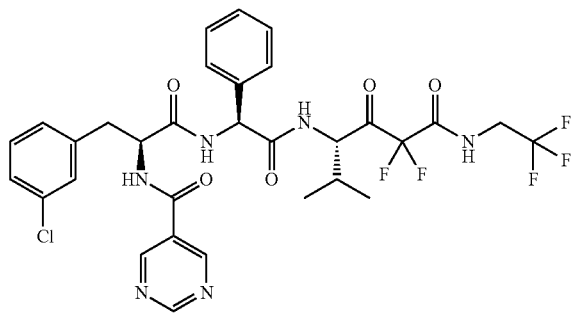 [SMILES: CC(C)[C@H](NC(=O)[C@@H](NC(=O)[C@H](Cc1cccc(Cl)c1)NC(=O)c1cncnc1)c1ccccc1)C(=O)C(F)(F)C(=O)NCC(F)(F)F]

was prepared in analogy to example 1, but using in step A] pyrimidine-5-carboxylic acid instead of pyridine-4-carboxylic acid, as white solid; MS: 695.4 (M+H⁺).

Example 5

N-[(2S)-3-(3,4-Dichlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide

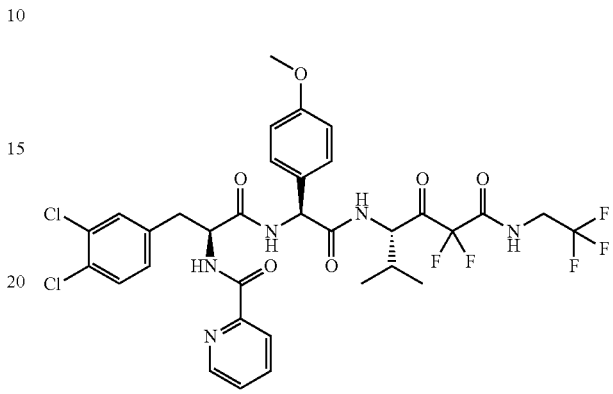

A] N-[(2S)-3-(3,4-Dichlorophenyl)-1-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-1-oxopropan-2-yl]pyridine-2-carboxamide

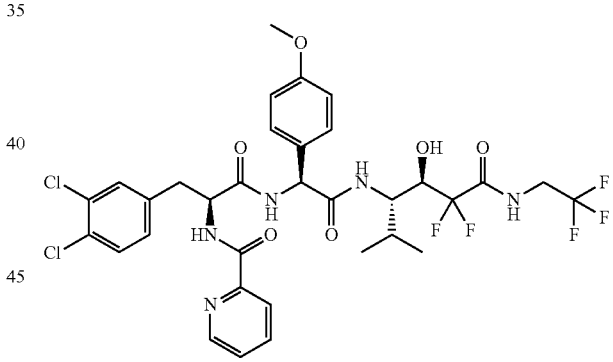

To a mixture of (3R,4S)-4-[[(2S)-2-amino-2-(4-methoxyphenyl)acetyl]amino]-2,2-difluoro-3-hydroxy-5-methyl-N-(2,2,2-trifluoroethyl)hexanamide hydrochloride (Intermediate IIb, 60 mg, 126 µmol, Eq: 1) and (S)-3-(3,4-dichlorophenyl)-2-(picolinamido)propanoic acid (Intermediate IVa, 42.6 mg, 126 µmol, Eq: 1) in DMF (4 ml) were successively added at 0° C. N,N-diisopropylethylamine (81.1 mg, 110 µl, 628 µmol, Eq: 5) and HATU (57.3 mg, 151 µmol, Eq: 1.2), and the reaction allowed to proceed for 1 hr at 0° C. The reaction mixture was subsequently quenched with sat. NaHCO₃ and ice and extracted with EtOAc (2×25 ml). The organic layers were washed with sat. NH₄Cl sol., then with brine. The organic layers were combined, dried over Na₂SO₄ and concentrated in vacuo. Purification by flash chromatography (silica gel, 20 g, 30% to 80% EtOAc in heptane) produced 48 mg of the title compound as off-white foam; MS: 762.4 (M+H⁺).

B] N-[(2S)-3-(3,4-Dichlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide In a 10 mL round-bottomed flask, the above prepared N-[(2S)-3-(3,4-dichlorophenyl)-1-[[(1S)-2-[[(3 S,4R)-5,5-difluoro-4-hydroxy-2-methyl-6-oxo-6-(2,2,2-trifluoroethyl-amino)hexan-3-yl]amino]-1-(4-methoxyphenyl)-2-oxo-ethyl]amino]-1-oxopropan-2-yl]pyridine-2-carboxamide (46 mg, 60.3 µmol, Eq: 1) was combined with dichloromethane (4 ml) and THF (2 ml) to give a colorless solution. Dess-Martin periodinane 15% in dichloromethane (256 mg, 188 µl, 90.5 µmol, Eq: 1.5) was added at 0° C. and the reaction mixture was stirred at rt for 2 h when LC-MS indicated some starting material to be still present; additional 0.1 ml Dess-Martin periodinane was added and the reaction mixture was further stirred for 2 hr at rt. It was then treated with sat. NaHCO$_3$ and extracted with DCM (2×20 ml). The organic layers were washed with brine, dried (Na$_2$SO$_4$) and evaporated. The crude material was purified by flash chromatography (silica gel, 10 g, 50% EtOAc in heptane) to afford 30 mg of the title product as white foam. Trituration with CH$_2$Cl$_2$/heptane afforded 15 mg of pure product as white solid; MS: 760.3 (M+H$^+$).

In close analogy, using the appropriate intermediates, were prepared examples 6-22 and 31-36, respectively, as summarized in the following Table:

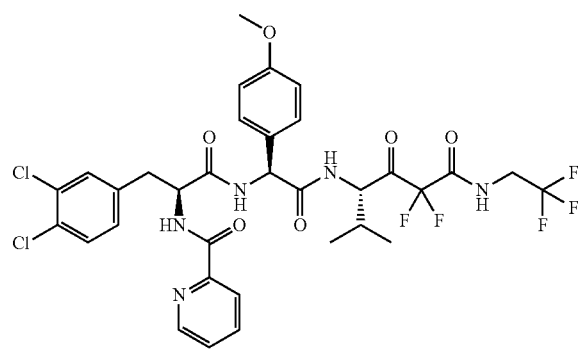 [SMILES: COc1ccc([C@H](NC(=O)[C@H](Cc2ccc(Cl)c(Cl)c2)NC(=O)c2ccccn2)C(=O)N[C@H](C(=O)C(F)(F)C(=O)NCC(F)(F)F)C(C)C)cc1]

| Example | Structure | Intermediates II and IV | Form Color MS |
|---|---|---|---|
| 6 | N-[(2S)-3-(3,4-Dichlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyridine-2-carboxamide | IIa and IVa | solid white 730.3 M + H)+ |
| 7 | N-[(2S)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide | IIb and IVk | solid white 726.3 M + H)+ |

| Example | Structure | Intermediates II and IV | Form Color MS |
|---|---|---|---|
| 8 | 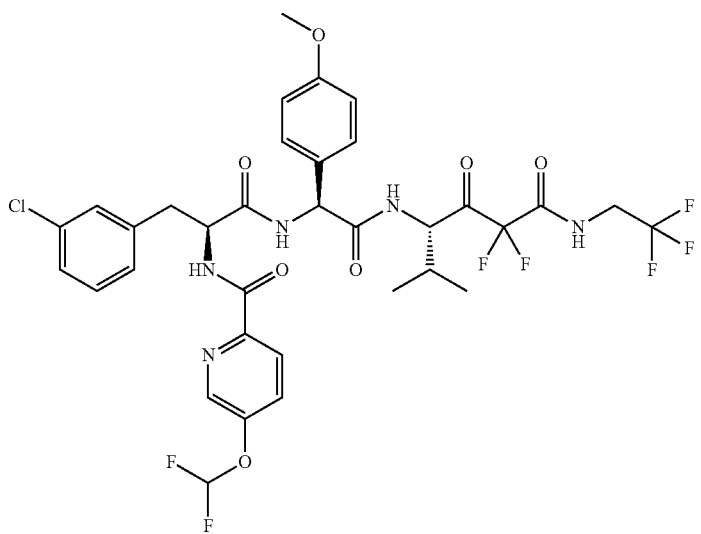 [SMILES: COc1ccc([C@H](NC(=O)[C@H](Cc2cccc(Cl)c2)NC(=O)c2ccc(OC(F)F)cn2)C(=O)N[C@H](C(=O)C(F)(F)C(=O)NCC(F)(F)F)C(C)C)cc1]<br>N-[(2S)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-5-(difluoromethoxy)pyridine-2-carboxamide | IIb and IVb | solid white 792.5 M + H)+ |
| 9 | 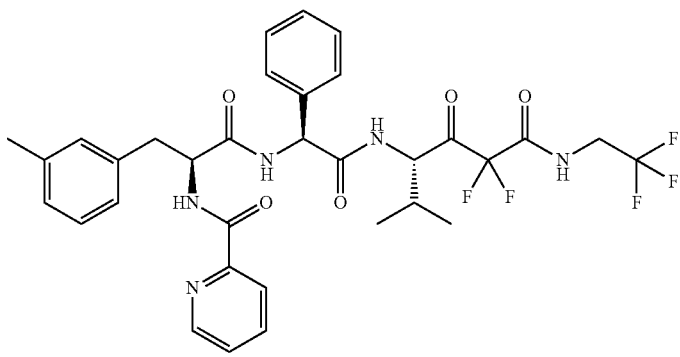 [SMILES: Cc1cccc(C[C@H](NC(=O)c2ccccn2)C(=O)N[C@H](C(=O)N[C@H](C(=O)C(F)(F)C(=O)NCC(F)(F)F)C(C)C)c2ccccc2)c1]<br>N-[(2S)-1-[[(1S)-2-[[(3S)-5,5-Difluoro-2-methyl-4,6-dioxo-6-(2,2,2-trifluoroethylamino)hexan-3-yl]amino]-2-oxo-1-phenylethyl]amino]-3-(3-methylphenyl)-1-oxopropan-2-yl]pyridine-2-carboxamide | IIa and IVc | solid white 676.5 M + H)+ |

| Example | Structure | Intermediates II and IV | Form Color MS |
|---|---|---|---|
| 10 | 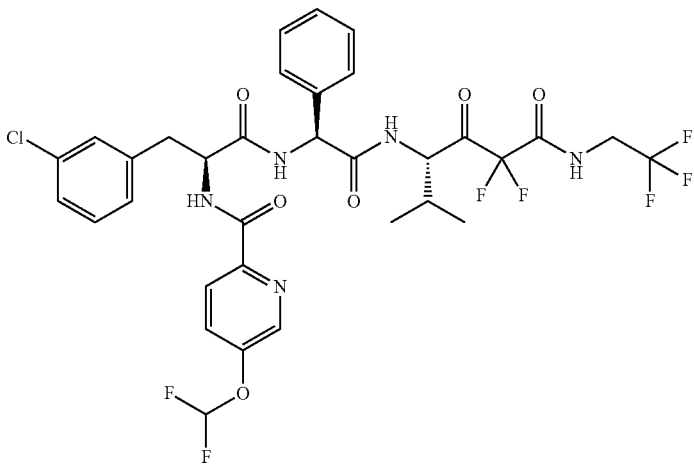 [SMILES: CC(C)[C@H](NC(=O)[C@@H](NC(=O)[C@H](Cc1cccc(Cl)c1)NC(=O)c1ccc(OC(F)F)cn1)c1ccccc1)C(=O)C(F)(F)C(=O)NCC(F)(F)F]<br><br>N-[(2S)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]-5-(difluoromethoxy)pyridine-2-carboxamide | IIa and IVb | solid white 762.4 M + H)+ |
| 11 | 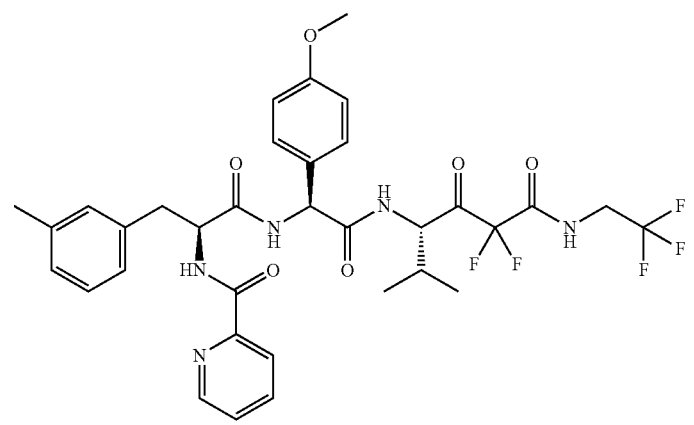 [SMILES: COc1ccc([C@H](NC(=O)[C@H](Cc2cccc(C)c2)NC(=O)c2ccccn2)C(=O)N[C@H](C(=O)C(F)(F)C(=O)NCC(F)(F)F)C(C)C)cc1]<br><br>N-[(2S)-1-[[(1S)-2-[[(3S)-5,5-Difluoro-2-methyl-4,6-dioxo-6-(2,2,2-trifluoroethylamino)hexan-3-yl]amino]-1-(4-methoxyphenyl)-2-oxoethyl]amino]-3-(3-methylphenyl)-1-oxopropan-2-yl]pyridine-2-carboxamide | IIb and IVc | solid white 706.5 M + H)+ |

-continued

| Example | Structure | Intermediates II and IV | Form Color MS |
|---|---|---|---|
| 12 | 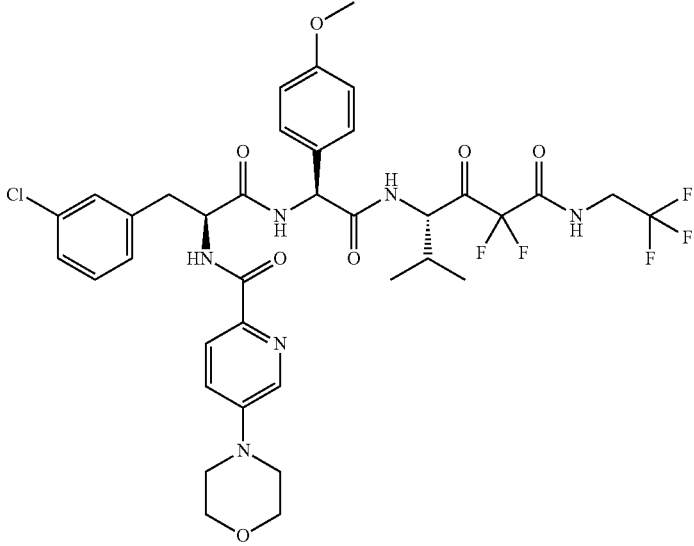 [SMILES: COc1ccc([C@H](NC(=O)[C@H](Cc2cccc(Cl)c2)NC(=O)c2ccc(N3CCOCC3)cn2)C(=O)N[C@H](C(=O)C(F)(F)C(=O)NCC(F)(F)F)C(C)C)cc1] N-[(2S)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-5-morpholin-4-ylpyridine-2-carboxamide | IIb and IVd | foam off-white 811.5 M + H)+ |
| 13 | 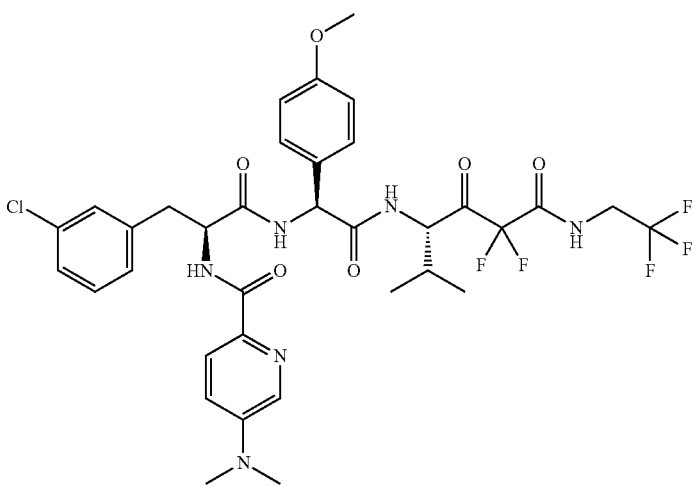 [SMILES: COc1ccc([C@H](NC(=O)[C@H](Cc2cccc(Cl)c2)NC(=O)c2ccc(N(C)C)cn2)C(=O)N[C@H](C(=O)C(F)(F)C(=O)NCC(F)(F)F)C(C)C)cc1] N-[(2S)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-5-(dimethylamino)pyridine-2-carboxamide | IIb and IVe | foam yellow 769.5 M + H)+ |

-continued

| Example | Structure | Intermediates II and IV | Form Color MS |
|---|---|---|---|
| 14 | N-[(2S)-3-(3-Cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide | IIb and IVf | foam white 717.3 M + H)+ |
| 15 | N-[3-(3-Chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide | IIb and IVl | solid white 725.4 M + H)+ |
| 16 | N-[3-(3-Chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]benzamide | IIa and IVl | solid white 695.3 M + H)+ |

| Example | Structure | Intermediates II and IV | Form Color MS |
|---|---|---|---|
| 17 | N-[(2S)-3-(3-Cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide | IIb and IVg | foam white 716.4 M + H)+ |
| 18 | N-[(2S)-3-(3-Chloro-4-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide | IIb and IVh | foam white 751.3 M + H)+ |

| Example | Structure | Intermediates II and IV | Form Color MS |
|---|---|---|---|
| 19 | 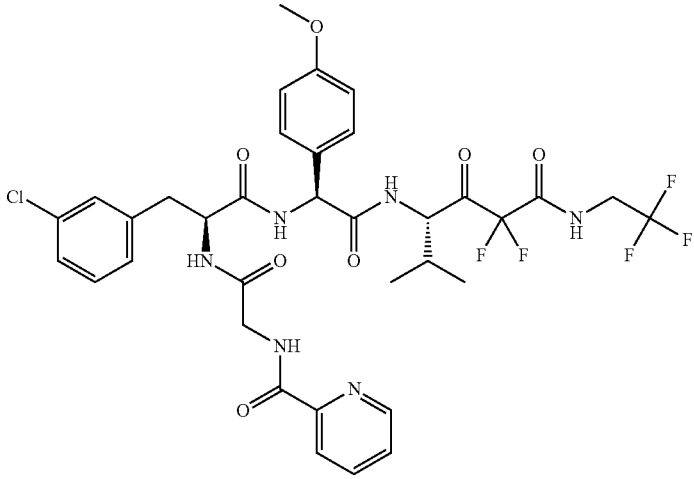 [SMILES: COc1ccc([C@H](NC(=O)[C@H](Cc2cccc(Cl)c2)NC(=O)CNC(=O)c2ccccn2)C(=O)N[C@H](C(=O)C(F)(F)C(=O)NCC(F)(F)F)C(C)C)cc1]<br>N-[2-[[(2S)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]amino]-2-oxoethyl]pyridine-2-carboxamide | IIb and IVm | oil light yellow 783.4 (M + H)+ |
| 20 | 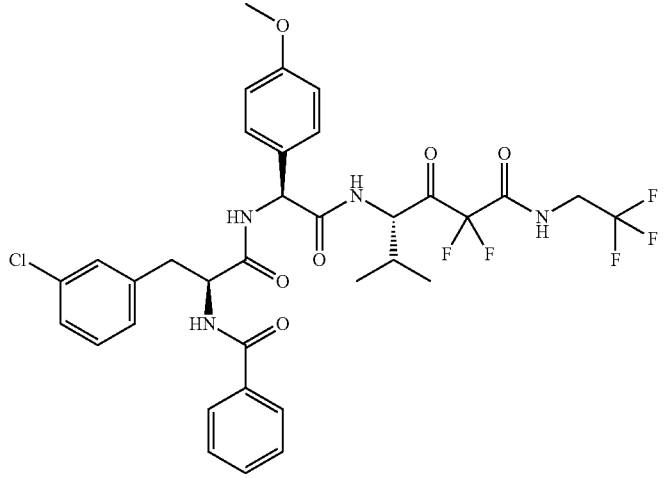 [SMILES: COc1ccc([C@H](NC(=O)[C@H](Cc2cccc(Cl)c2)NC(=O)c2ccccc2)C(=O)N[C@H](C(=O)C(F)(F)C(=O)NCC(F)(F)F)C(C)C)cc1]<br>N-[(2S)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide | IIb and IVi | solid white 725.3 (M + H)+ |

-continued

| Example | Structure | Intermediates II and IV | Form Color MS |
|---|---|---|---|
| 21 | 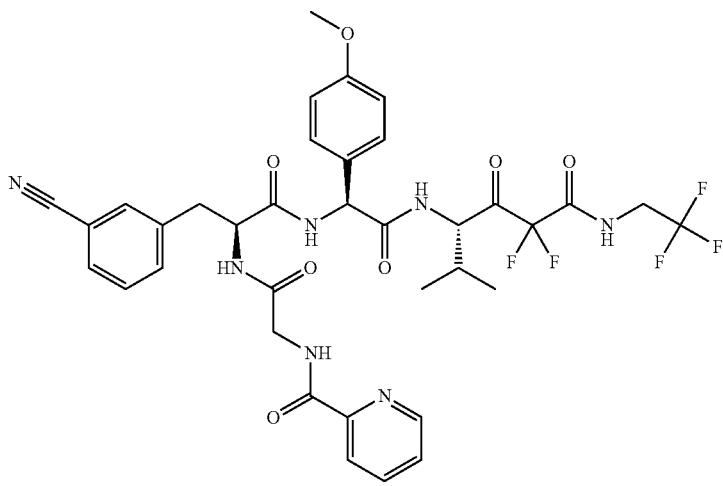 [SMILES: COc1ccc([C@H](NC(=O)[C@H](Cc2cccc(C#N)c2)NC(=O)CNC(=O)c2ccccn2)C(=O)N[C@H](C(=O)C(F)(F)C(=O)NCC(F)(F)F)C(C)C)cc1]<br>N-[2-[[(2S)-3-(3-Cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]amino]-2-oxoethyl]pyridine-2-carboxamide | IIb and IVn | semisolid white 774.4 (M + H)+ |
| 22 | 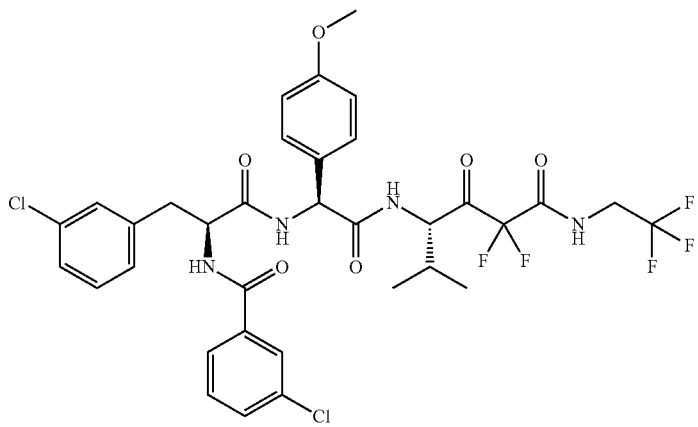 [SMILES: COc1ccc([C@H](NC(=O)[C@H](Cc2cccc(Cl)c2)NC(=O)c2cccc(Cl)c2)C(=O)N[C@H](C(=O)C(F)(F)C(=O)NCC(F)(F)F)C(C)C)cc1]<br>3-Chloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide | IIb and IVj | solid white 759.3 (M + H)+ |

| Example | Structure | Intermediates II and IV | Form Color MS |
|---|---|---|---|
| 31 | 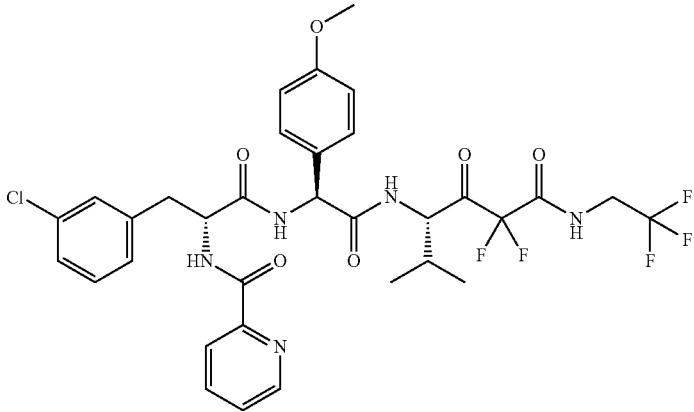 [SMILES: COc1ccc([C@H](NC(=O)[C@@H](Cc2cccc(Cl)c2)NC(=O)c2ccccn2)C(=O)N[C@H](C(=O)C(F)(F)C(=O)NCC(F)(F)F)C(C)C)cc1]

N-[(2R)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide | IIb and IVo | semisolid white 726.3 (M + H)+ |
| 32 | 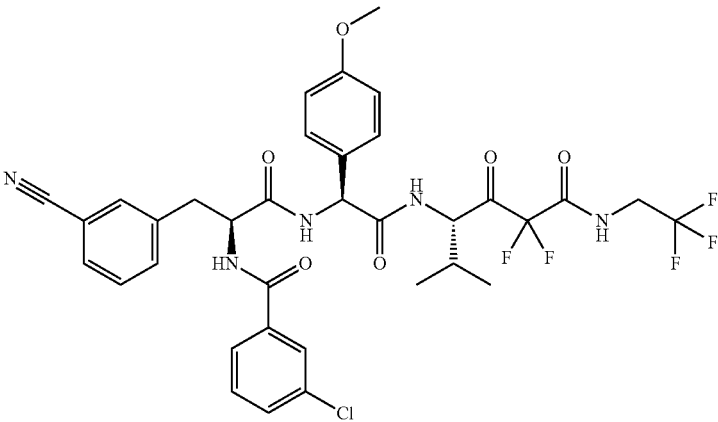 [SMILES: COc1ccc([C@H](NC(=O)[C@H](Cc2cccc(C#N)c2)NC(=O)c2cccc(Cl)c2)C(=O)N[C@H](C(=O)C(F)(F)C(=O)NCC(F)(F)F)C(C)C)cc1]

3-Chloro-N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide | IIb and IVp | solid white 748.4 (M − H)− |

| Example | Structure | Intermediates II and IV | Form Color | MS |
|---|---|---|---|---|
| 33 | 5-Chloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]thiophene-2-carboxamide | IIb and IVq | solid white | 765.2 (M + H)+ |
| 34 | 5-Chloro-N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]thiophene-2-carboxamide | IIb and IVr | solid white | 756.2 (M + H)+ |

| Example | Structure | Intermediates II and IV | Form Color MS |
|---|---|---|---|
| 35 | N-[(2S)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-3-cyanobenzamid | IIb and IVs | solid white 750.2 (M + H)+ |
| 36 | 2,5-Dichloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide | IIb and IVt | foam off-white 795.2 (M + H)+ |

Example 23

N-[(2S)-1-[[(1S)-2-[[(3S)-5,5-Difluoro-2-methyl-4,6-dioxo-6-(2,2,2-trifluoroethylamino)-hexan-3-yl]amino]-1-(4-methoxyphenyl)-2-oxoethyl]amino]-3-hydroxy-1-oxopropan-2-yl]benzamide

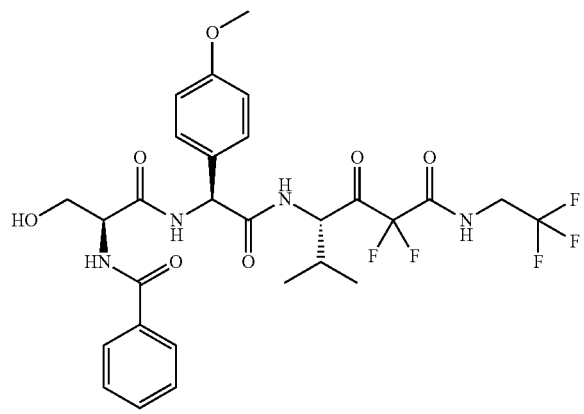 [SMILES: COc1ccc([C@H](NC(=O)[C@H](CO)NC(=O)c2ccccc2)C(=O)N[C@H](C(=O)C(F)(F)C(=O)NCC(F)(F)F)C(C)C)cc1]

A] N-[(2S)-3-[tert-Butyl(dimethyl)silyl]oxy-1-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-1-oxopropan-2-yl]benzamide

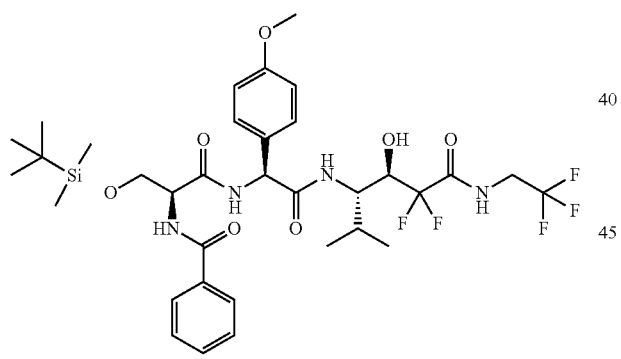

To a mixture of (4S)-4-((S)-2-amino-2-(4-methoxyphenyl)acetamido)-2,2-difluoro-3-hydroxy-5-methyl-N-(2,2,2-trifluoroethyl)hexanamide hydrochloride (Intermediate IIb, 100 mg, 209 µmol, Eq: 1) and N,N-diisopropylethylamine (135 mg, 183 µl, 1.05 mmol, Eq: 5) in DMF (5 ml) were added at 0° C. (S)-2-benzamido-3-((tert-butyldimethylsilyl)oxy)propanoic acid (Intermediate IVu, 67.7 mg, 209 µmol, Eq: 1) and HATU (95.5 mg, 251 µmol, Eq: 1.2), and the reaction mixture was stirred for 1 hr at 0° C. It was then quenched with sat. NaHCO₃ and ice and extracted with EtOAc (2×25 ml). The organic layers were washed with NH₄Cl, followed by brine. They were combined, dried over Na₂SO₄, and concentrated in vacuo. Purification by flash chromatography (silica gel, 20 g, 20% to 80% EtOAc in heptane) gave 87 mg of the title product as yellow semisolid; MS: 747.5 (M+H⁺).

B] N-[(2S)-3-[tert-Butyl(dimethyl)silyl]oxy-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide

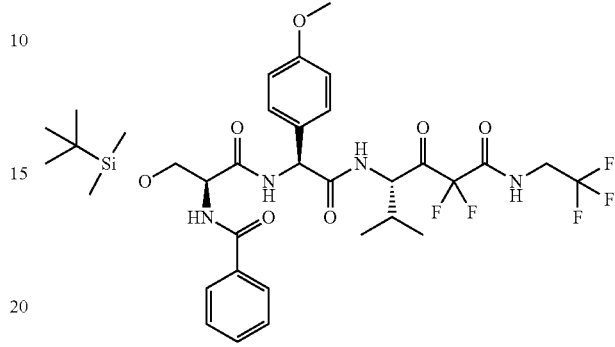

In a 10 mL round-bottomed flask, the above prepared N-((6S,9S,12S)-14,14,18,18,18-pentafluoro-13-hydroxy-12-isopropyl-9-(4-methoxyphenyl)-2,2,3,3-tetramethyl-7,10,15-trioxo-4-oxa-8,11,16-triaza-3-silaoctadecan-6-yl)benzamide (84 mg, 112 µmol, Eq: 1) was combined with CH₂Cl₂ (5 ml) to give a light yellow solution. Dess-Martin periodinane 15% in CH₂Cl₂ (477 mg, 350 µl, 169 µmol, Eq: 1.5) was added at 0° C. and the reaction mixture was stirred for 1 hr at rt. It was then treated with sat. NaHCO₃ and extracted with CH₂Cl₂ (2×20 mL). The organic layers were washed with brine, dried (Na₂SO₄) and evaporated i. V. The crude material was purified by flash chromatography (silica gel, 20 g, 50% EtOAc in heptane) to generate 56 mg of ther title ketone as white foam; MS: 745.4 (M+H⁺).

C] N-[(2S)-1-[[(1S)-2-[[(3S)-5,5-difluoro-2-methyl-4,6-dioxo-6-(2,2,2-trifluoroethylamino)-hexan-3-yl]amino]-1-(4-methoxyphenyl)-2-oxoethyl]amino]-3-hydroxy-1-oxopropan-2-yl]benzamide

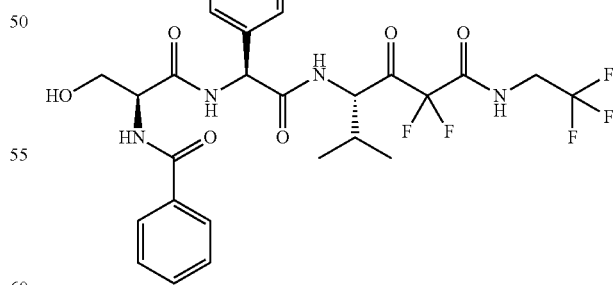

In a 10 mL round-bottomed flask, the above prepared N-((6S,9S,12S)-14,14,18,18,18-pentafluoro-12-isopropyl-9-(4-methoxyphenyl)-2,2,3,3-tetramethyl-7,10,13,15-tetraoxo-4-oxa-8,11,16-triaza-3-silaoctadecan-6-yl)benzamide (54 mg, 72.5 µmol, Eq: 1) was combined with THF (4 ml) to give a colorless solution. HCl 4M in dioxane (272 µl, 1.09 mmol, Eq: 15) was added at 0° C., followed by 2 drops of H₂O. The reaction mixture was stirred at rt for 30 min., when LC-MS indicated the reaction to be finished. The mixture was poured into H₂O and extracted with EtOAc (2×25 mL). The organic layers were dried over Na₂SO₄ and concentrated in vacuo. Precipitation from AcOEt/Hept afforded 30 mg of pure title product as white solid; MS: 631.3 (M+H⁺).

Example 24

1-(3-Chlorophenyl)-N-[(2S)-1-[[(1S)-2-[[(3S)-5,5-difluoro-2-methyl-4,6-dioxo-6-(2,2,2-trifluoroethyl-amino)hexan-3-yl]amino]-1-(4-methoxyphenyl)-2-oxoethyl]amino]-3-hydroxy-1-oxopropan-2-yl]cyclopropane-1-carboxamide

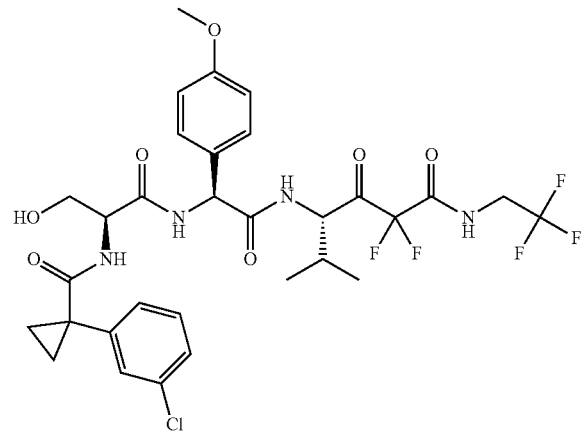 [SMILES: COc1ccc([C@H](NC(=O)[C@H](CO)NC(=O)C2(c3cccc(Cl)c3)CC2)C(=O)N[C@H](C(=O)C(F)(F)C(=O)NCC(F)(F)F)C(C)C)cc1]

was prepared in analogy to example 23 but using in step A] Intermediate IVv instead of IVu, as colorless oil; MS: 705.3 (M+H)⁺.

Example 25

1-(3-Chlorophenyl)-N-[(2S,3R)-1-[[(1S)-2-[[(3S)-5,5-difluoro-2-methyl-4,6-dioxo-6-(2,2,2-trifluoroeth-ylamino)hexan-3-yl]amino]-1-(4-methoxyphenyl)-2-oxoethyl]amino]-3-hydroxy-1-oxobutan-2-yl]cyclopropane-1-carboxamide

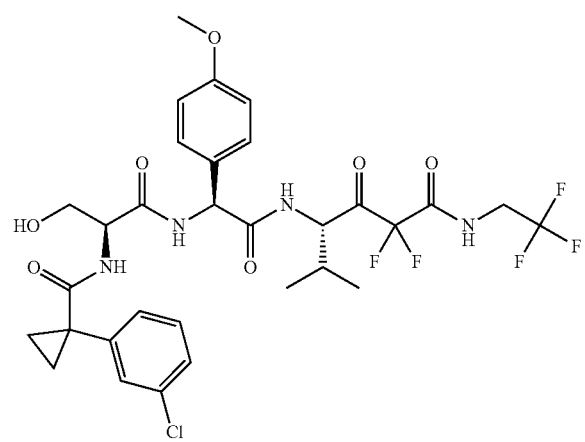 [SMILES: COc1ccc([C@H](NC(=O)[C@H](CO)NC(=O)C2(c3cccc(Cl)c3)CC2)C(=O)N[C@H](C(=O)C(F)(F)C(=O)NCC(F)(F)F)C(C)C)cc1]

was prepared in analogy to example 23, but using in step A] Intermediate IVw instead of IVu, as white foam; MS: 717.4 (M−H)⁻.

Example 26

N-[(2S)-1-[[(1S)-2-[[(3S)-5,5-Difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide

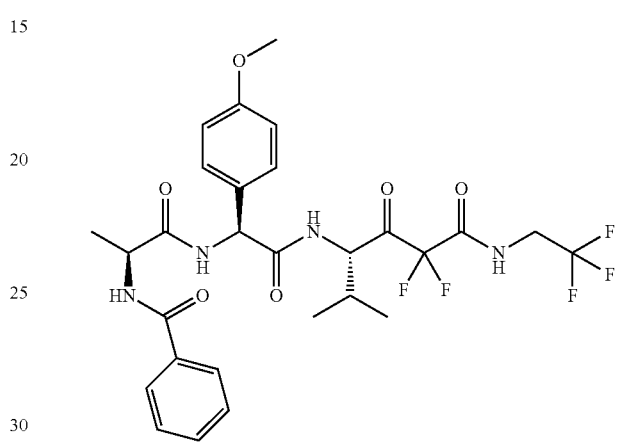

was prepared in analogy to example 23, but using in step A] (2S)-2-benzamidopropanoic acid (commercially available) instead of IVu, as light yellow foam; MS: 615.3 (M+H)⁺.

Example 27

1-(3-Chlorophenyl)-N-[(2S)-1-[[(1S)-2-[[(3S)-5,5-difluoro-2-methyl-4,6-dioxo-6-(2,2,2-trifluoroethyl-amino)hexan-3-yl]amino]-2-oxo-1-phenylethyl]amino]-1-oxopropan-2-yl]cyclopropane-1-carboxamide

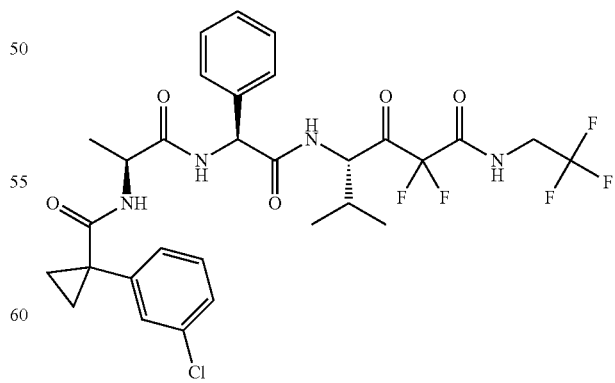

was prepared in analogy to example 23, but using in step A] Intermediate IIa instead of IIb and Intermediate IVx instead of IVu, as white foam; MS: 659.3 (M+H)⁺.

Example 28

1-(3-Chlorophenyl)-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]cyclopropane-1-carboxamide

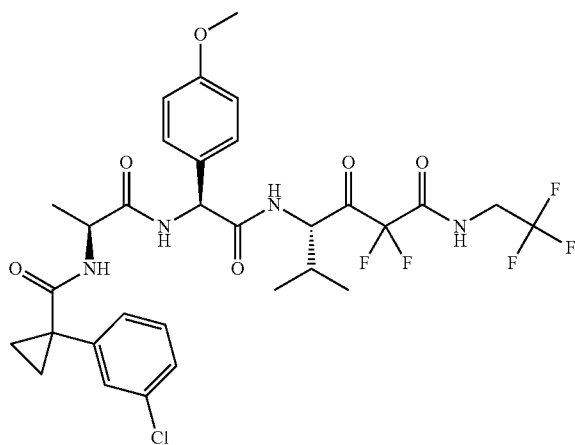 [SMILES: COc1ccc([C@H](NC(=O)[C@H](C)NC(=O)C2(c3cccc(Cl)c3)CC2)C(=O)N[C@H](C(=O)C(F)(F)C(=O)NCC(F)(F)F)C(C)C)cc1]

was prepared in analogy to example 23, but using in step A] Intermediate IVx instead of IVu, as colorless oil; MS: 689.3 (M+H)⁺.

Example 29

2,5-Dichloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide

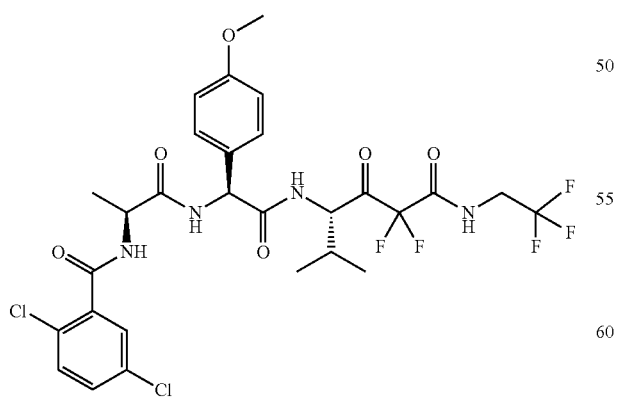

was prepared in analogy to example 23, but using in step A] Intermediate IVy instead of IVu, as white solid; MS: 683.2 (M+H)⁺.

Example 30

3-Chloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide

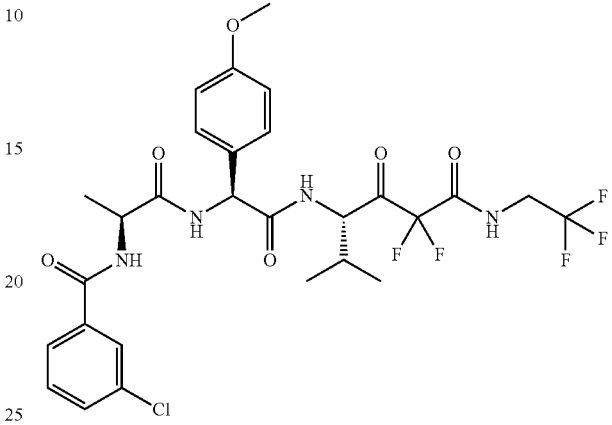

was prepared in analogy to example 23, but using in step A] Intermediate IVz instead of IVu, as white solid; MS: 647.4 (M−H)⁻.

Example 37 tert-Butyl 2-[4-[[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]carbamoyl]phenoxy]acetate

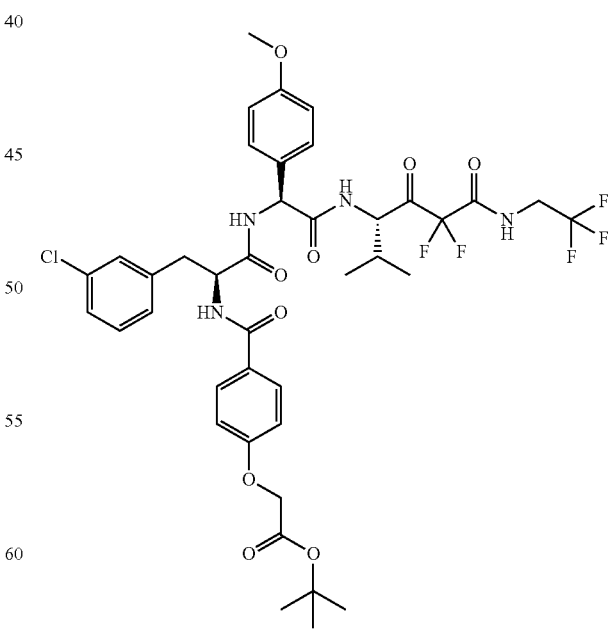

was prepared in analogy to example 5, but using in step A] Intermediate IVaa instead of IVa, as off-white solid; MS: 855.3 (M+H⁺).

Example 38

2-[4-[[(2S)-3-(3-Chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]carbamoyl]phenoxy]acetic acid

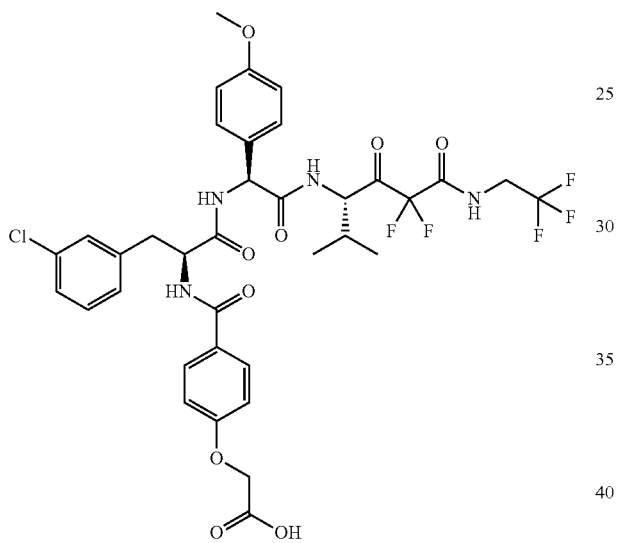

To a solution of the above prepared tert-butyl 2-[4-[[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]carbamoyl]phenoxy]acetate (Example 37, 25 mg, 29.2 µmol, Eq: 1) in DCM (1 ml) was added TFA (45 µl, 585 µmol, Eq: 20) and the reaction mixture was stirred at room temperature for 6 h. The mixture was evaporated to dryness and the residue triturated in diisopropylether. The resulting precipitate was filtered off and further dried on high vaccum to yield 15 mg of the title product as colorless solid; MS: 799.4 (M+H$^+$).

Example 39

2-[4-[(2S)-2-[[2-(3-Chlorophenyl)-2,2-difluoroacetyl]amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetic acid

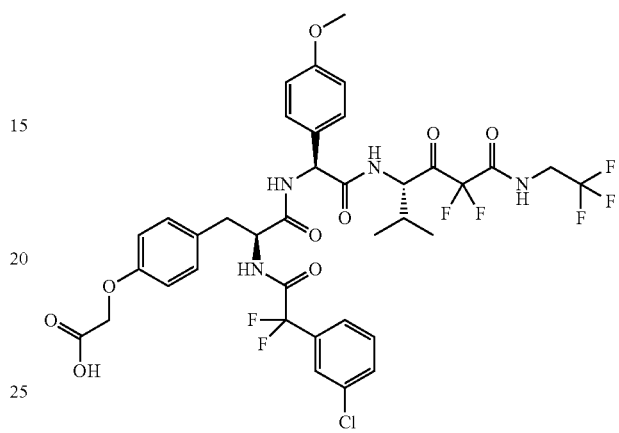

A] tert-Butyl 2-[4-[(2S)-2-[[2-(3-Chlorophenyl)-2,2-difluoroacetyl]amino]-3-[[(1S)-2-[[(3S,4R)- 5,5-difluoro-4-hydroxy-2-methyl-6-oxo-6-(2,2,2-trifluoroethylamino)hexan-3-yl]amino]-1-(4-methoxyphenyl)-2-oxoethyl]amino]-3-oxopropyl]phenoxy]acetate

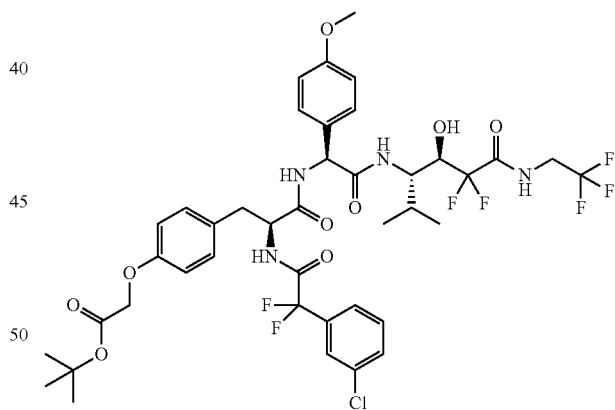

To a solution of tert-butyl 2-[4-[(2S)-2-amino-3-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-3-oxopropyl]phenoxy]acetate hydrochloride (Intermediate IIIb, 30 mg, 39.7 mol, Eq: 1) in DCM (1 ml), cooled to 0° C. with an ice bath, was added 2-(3-chlorophenyl)-2,2-difluoroacetyl chloride (9.83 mg, 43.7 µmol, Eq: 1.1) and the reaction mixture was stirred at this temperature overnight. The mixture was diluted with EtOAc, poured into 1M HCl and extracted with EtOAc (2×10 ml). The combined organic layers were washed with brine, dried over Na$_2$SO$_4$, filtered, and evaporated. The residue was purified by silica gel flash chromatography, eluting with a 0 to 70% EtOAc-heptane gradient, to yield 28 mg of the title product as colorless solid; MS: 851.3 (M-tBu+H⁺).

B] tert-Butyl 2-[4-[(2S)-2-[[2-(3-chlorophenyl)-2,2-difluoroacetyl]amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetate

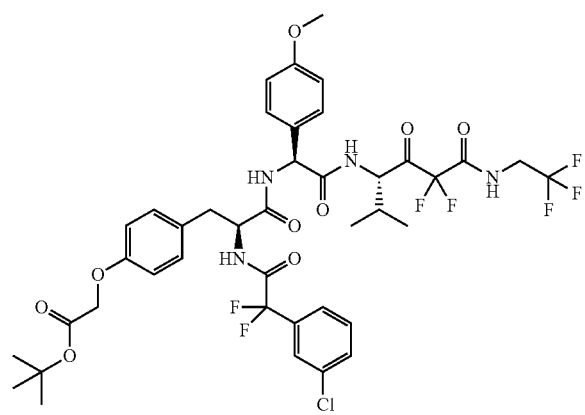 [SMILES: COc1ccc([C@H](NC(=O)[C@H](Cc2ccc(OCC(=O)OC(C)(C)C)cc2)NC(=O)C(F)(F)c2cccc(Cl)c2)C(=O)N[C@H](C(=O)C(F)(F)C(=O)NCC(F)(F)F)C(C)C)cc1]

To a solution of the above prepared tert-butyl 2-[4-[(2S)-2-[[2-(3-chlorophenyl)-2,2-difluoroacetyl]amino]-3-[[(1S)-2-[[(3 S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-3-oxopropyl]phenoxy]acetate (0.028 g, 30.9 µmol, Eq: 1) in CH₂Cl₂ (1 ml), cooled to 0° C., was added Dess-Martin periodinane 15% in dichloromethane (262 mg, 192 µl, 92.6 µmol, Eq: 3), and the reaction mixture was stirred at room temperature overnight. The reaction mixture was treated with sat. NaHCO₃ and extracted with DCM (2×10 ml). The organic layers were washed with brine, dried over Na₂SO₄ and evaporated. The residue was purified by silica gel flash chromatography, eluting with a 0 to 60% EtOAc-heptane gradient, to yield 20 mg of the title product as colorless solid; MS: 905.3 (M+H⁺).

C] 2-[4-[(2S)-2-[[2-(3-Chlorophenyl)-2,2-difluoroacetyl]amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetic acid

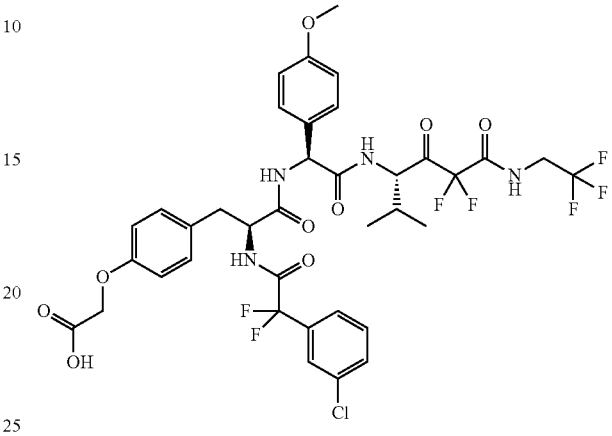

was prepared in analogy to example 38 from the above prepared tert-butyl 2-[4-[(2S)-2-[[2-(3-chlorophenyl)-2,2-difluoroacetyl]amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetate as colorless solid; MS: 849.4 (M+H⁺).

Example 40

2-[4-[(2S)-2-[(3-Chlorobenzoyl)amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetic acid

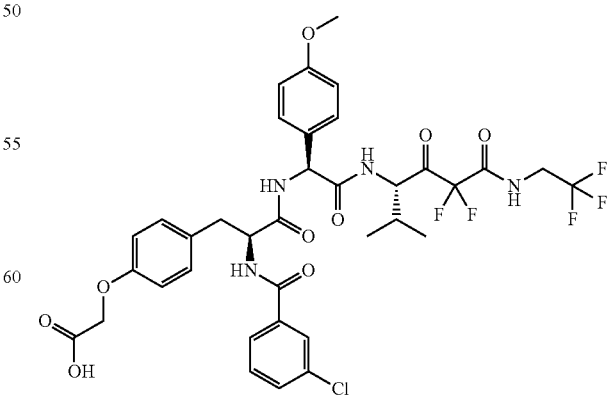

A] tert-Butyl 2-[4-[(2S)-2-[(3-chlorobenzoyl)amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetate

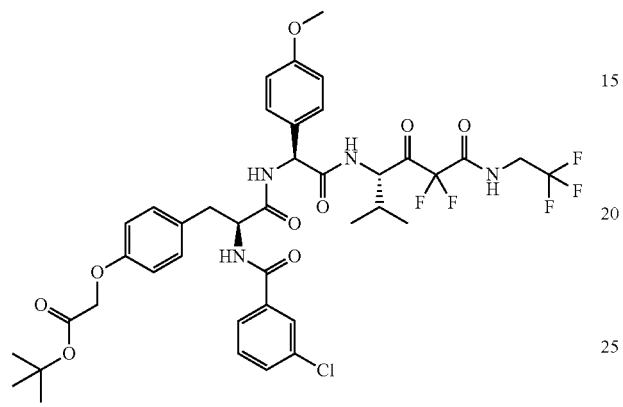

was prepared in analogy to example 1, but using in step A] Intermediate IIIb instead of IIIa and 3-chlorobenzoic acid instead of pyridine-4-carboxylic acid, as colorless solid; MS: 855.4 (M+H⁺).

B] 2-[4-[(2S)-2-[(3-Chlorobenzoyl)amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetic acid

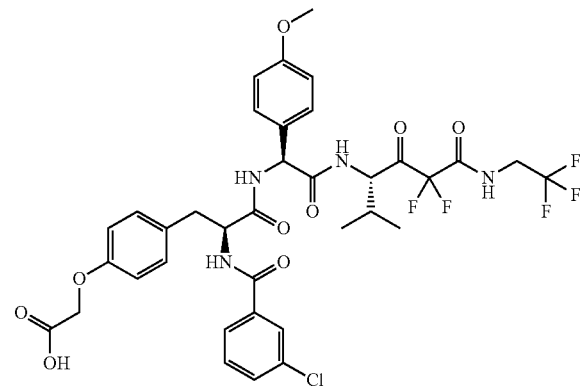 [SMILES: COc1ccc([C@H](NC(=O)[C@H](Cc2ccc(OCC(=O)O)cc2)NC(=O)c2cccc(Cl)c2)C(=O)N[C@H](C(=O)C(F)(F)C(=O)NCC(F)(F)F)C(C)C)cc1]

was prepared in analogy to example 38 from the above prepared tert-butyl 2-[4-[(2S)-2-[(3-chlorobenzoyl)amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetate, as colorless solid; MS: 799.4 (M+H⁺).

Example 41

(4S)-4-[[(2S)-2-[[(2S)-3-(3-Chlorophenyl)-2-[[2-(3-chlorophenyl)-2,2-difluoroacetyl]amino]propanoyl]amino]-2-(4-methoxyphenyl)acetyl]amino]-2,2-difluoro-5-methyl-3-oxo-N-(2,2,2-trifluoroethyl)hexanamide was prepared in analogy to example 39, but using in step A] (3R,4S)-4-[[(2S)-2-[[(2S)-2-amino-3-(3-chlorophenyl)propanoyl]amino]-2-(4-methoxyphenyl)acetyl]amino]-2,2-difluoro-3-hydroxy-5-methyl-N-(2,2,2-trifluoroethyl)hexanamide hydrochloride (Intermediate IIIc) instead of tert-butyl 2-[4-[(2S)-2-amino-3-[[(1S)-2-[[(3S,4R)-5,5-difluoro-4-hydroxy-2-methyl-6-oxo-6-(2,2,2-trifluoroethylamino)hexan-3-yl]amino]-1-(4-methoxyphenyl)-2-oxoethyl]amino]-3-oxopropyl]phenoxy]acetate hydrochloride (Intermediate IIIb), as light-yellow foam; MS: 809.3 (M+H⁺).

In close analogy to Example 5, using the appropriate intermediates, were prepared examples 42-44, 47-51, 56, and 58-60, respectively, as summarized in the following Table:

| Example | Structure/Name | Intermediates II and IV | Form Color MS |
|---|---|---|---|
| 42 | 3-Chloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide | IIb and IVbb | foam light yellow 745.4 (M + H) |
| 43 | N-[(2S)-1-[[(1S)-2-[[(3S)-5,5-Difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]pyridine-2-carboxamide | IIb and IVcc | solid white 710.5 (M + H)+ |

| Example | Structure/Name | Intermediates II and IV | Form Color MS |
|---|---|---|---|
| 44 | 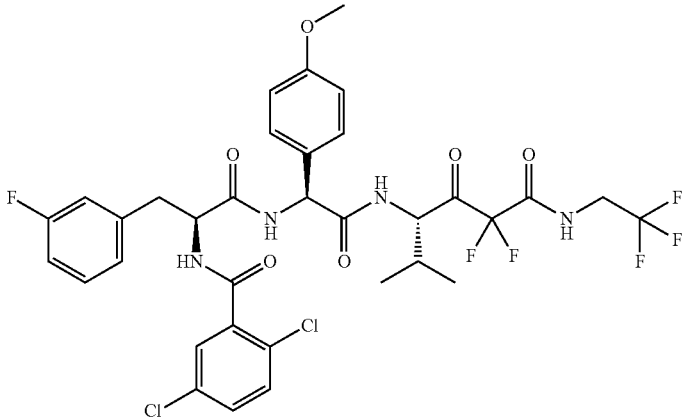 [SMILES: COc1ccc([C@H](NC(=O)[C@H](Cc2cccc(F)c2)NC(=O)c2cc(Cl)ccc2Cl)C(=O)N[C@H](C(=O)C(F)(F)C(=O)NCC(F)(F)F)C(C)C)cc1]

2,5-Dichloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide | IIb and IVdd | solid white 777.2 (M + H)+ |
| 47 | 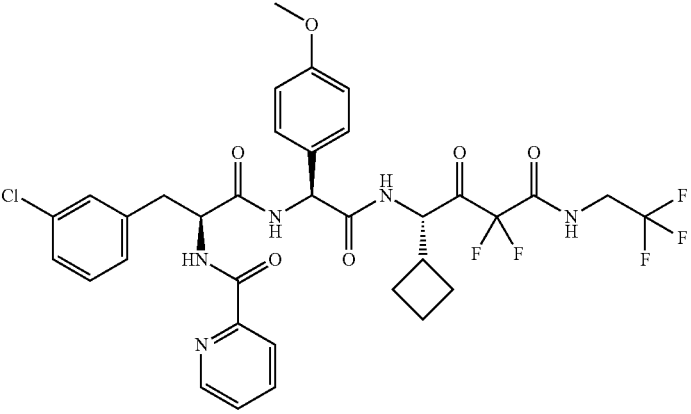 [SMILES: COc1ccc([C@H](NC(=O)[C@H](Cc2cccc(Cl)c2)NC(=O)c2ccccn2)C(=O)N[C@H](C(=O)C(F)(F)C(=O)NCC(F)(F)F)C2CCC2)cc1]

N-[(2S)-3-(3-Chlorophenyl)-1-[[(1S)-2-[[(1S)-1-cyclobutyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide | IIc and IVk | oil colorless 738.3 (M + H) |

-continued

| Example | Structure/Name | Intermediates II and IV | Form Color MS |
|---|---|---|---|
| 48 | 3-Chloro-N-[(2S)-3-(4-chloro-3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide | IIb and IVee | solid white 784.2 (M + H)+ |
| 49 | N-[(2S)-3-(3-Cyanophenyl)-1-[[(1S)-2-[[(1S)-1-cyclobutyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide | IIc and IVf | foam white 729.3 (M + H) |

| Example | Structure/Name | Intermediates II and IV | Form Color MS |
|---|---|---|---|
| 50 | 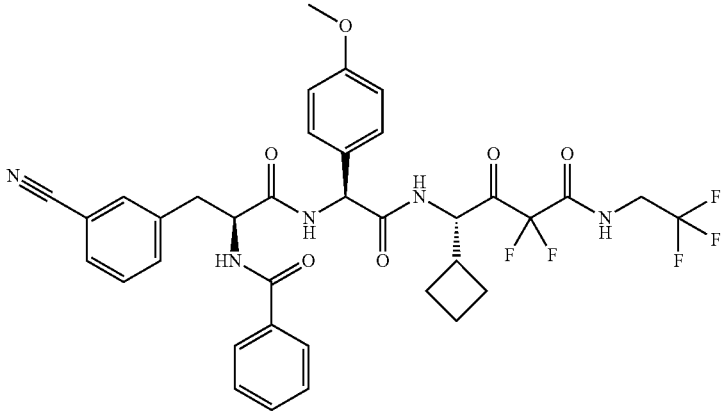 [SMILES: COc1ccc([C@H](NC(=O)[C@H](Cc2cccc(C#N)c2)NC(=O)c2ccccc2)C(=O)N[C@H](C(=O)C(F)(F)C(=O)NCC(F)(F)F)C2CCC2)cc1]<br><br>N-[(2S)-3-(3-Cyanophenyl)-1-[[(1S)-2-[[(1S)-1-cyclobutyl-3,3-difluoro-2,4-dioxo-4-(2,2,2-trifluoroethylamino)butyl]amino]-1-(4-methoxyphenyl)-2-oxoethyl]amino]-1-oxopropan-2-yl]benzamide | IIc and IVg | solid white 728.3 (M + H) |
| 51 | 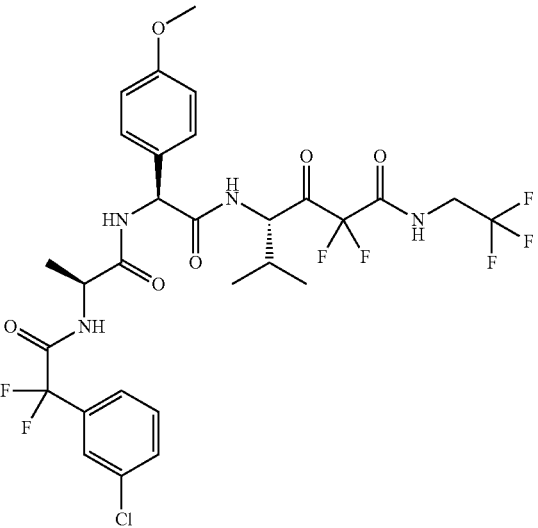 [SMILES: COc1ccc([C@H](NC(=O)[C@H](C)NC(=O)C(F)(F)c2cccc(Cl)c2)C(=O)N[C@H](C(=O)C(F)(F)C(=O)NCC(F)(F)F)C(C)C)cc1]<br><br>(4S)-4-[[(2S)-2-[[(2S)-2-[[2-(3-Chlorophenyl)-2,2-difluoroacetyl]amino]propanoyl]amino]-2-(4-methoxyphenyl)acetyl]amino]-2,2-difluoro-5-methyl-3-oxo-N-(2,2,2-trifluoroethyl)hexanamide | IIb and IVff | solid white 699.3 (M + H)+ |

| Example | Structure/Name | Intermediates II and IV | Form Color MS |
|---------|----------------|-------------------------|---------------|
| 56 | 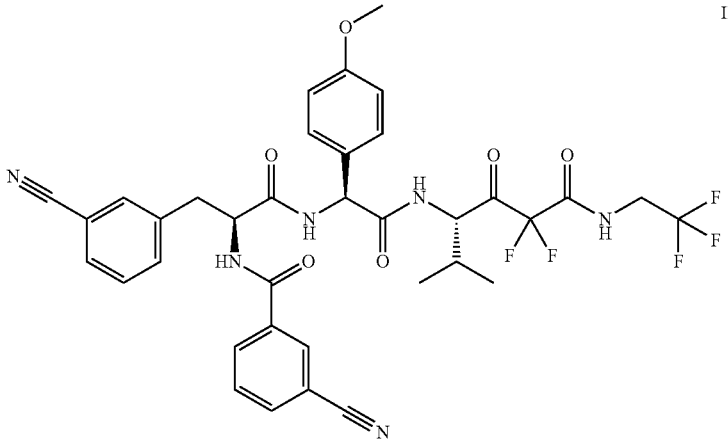 [SMILES: COc1ccc([C@H](NC(=O)[C@H](Cc2cccc(C#N)c2)NC(=O)c2cccc(C#N)c2)C(=O)N[C@H](C(=O)C(F)(F)C(=O)NCC(F)(F)F)C(C)C)cc1]

3-Cyano-N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide | IIb and IVgg | solid white 741.4 (M + H)+ |
| 58 | 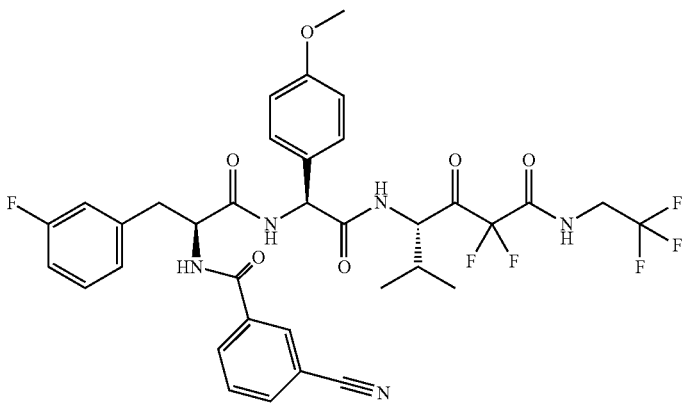 [SMILES: COc1ccc([C@H](NC(=O)[C@H](Cc2cccc(F)c2)NC(=O)c2cccc(C#N)c2)C(=O)N[C@H](C(=O)C(F)(F)C(=O)NCC(F)(F)F)C(C)C)cc1]

3-Cyano-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benamide | IIb and IVhh | solid white 734.4 (M + H)+ |

| Example | Structure/Name | Intermediates II and IV | Form Color MS |
|---|---|---|---|
| 59 | N-[(2S)-3-(3-Chlorophenyl)-1-[[(1S)-2-[[(1S)-1-cyclopropyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide | IId and IVk | solid white 724.3 (M + H) |
| 60 | N-[(2S)-3-(3-Cyanophenyl)-1-[[(1S)-2-[[(1S)-1-cyclopropyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide | IId and IVf | solid white 715.3 (M + H) |

Example 52

N-[(2S)-3-(3-Chlorophenyl)-1-[[(1S)-2-[[(3S)-5,5-difluoro-2-methyl-4,6-dioxo-6-(2,2,2-trifluoroethyl-amino)hexan-3-yl]amino]-1-(4-methoxyphenyl)-2-oxoethyl]amino]-1-oxopropan-2-yl]-3-fluorobenzamide

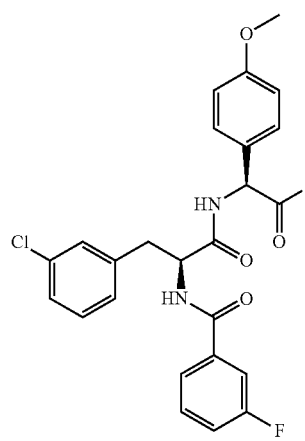

was prepared in analogy to Example 1, but using Intermediate IIIc and 3-fluorobenzoic acid as respective building block, as white solid; MS; 743.3 (M+H)⁺.

Example 53

3,5-Dichloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide

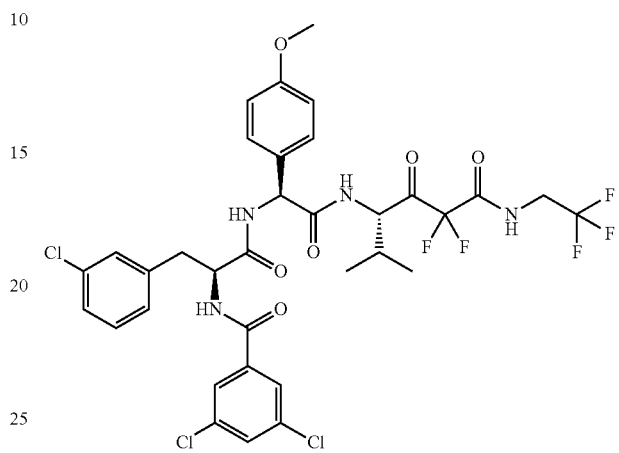

was prepared in analogy to Example 1, using Intermediate IIIc and 3,5-dichlorobenzoic acid as respective building block, as white solid; MS; 795.2 (M+H)⁺.

Example 45, 46, 54, 55, and 57, respectively, were prepared in analogy to Example 39 using the appropriate building blocks as indicated in the following Table:

| Ex | Structure/Name | Intermediate III | Acid chloride | Form Color MS |
|---|---|---|---|---|
| 45 | ![structure] (4S)-4-[[(2S)-2-[[(2S)-3-(3-chlorophenyl)-2-[[2-(3-chlorophenyl)acetyl]amino]propanoyl]amino]-2-(4-methoxyphenyl)acetyl]amino]-2,2-difluoro-5-methyl-3-oxo-N-(2,2,2-trifluoroethyl)hexanamide | IIIc | ![Cl-phenylacetyl chloride] | solid white 773.3 (M + H)+ |

| Ex | Structure/Name | Intermediate III | Acid chloride | Form Color MS |
|---|---|---|---|---|
| 46 | 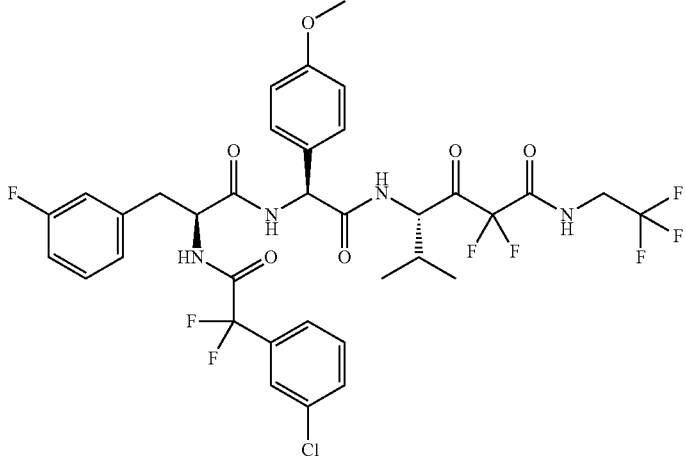 [SMILES: COc1ccc([C@H](NC(=O)[C@H](Cc2cccc(F)c2)NC(=O)C(F)(F)c2cccc(Cl)c2)C(=O)N[C@H](C(=O)C(F)(F)C(=O)NCC(F)(F)F)C(C)C)cc1]<br>(4S)-4-[[(2S)-2-[[(2S)-2-[[2-(3-chlorophenyl)-2,2-difluoroacetyl]amino]-3-(3-fluorophenyl)propanoyl]amino]-2-(4-methoxyphenyl)acetyl]amino]-2,2-difluoro-5-methyl-3-oxo-N-(2,2,2-trifluoroethyl)hexanamide | IIId | 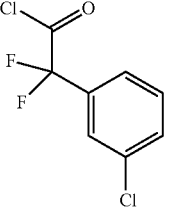 [SMILES: O=C(Cl)C(F)(F)c1cccc(Cl)c1] | foam white 793.3 (M + H)+ |
| 54 | 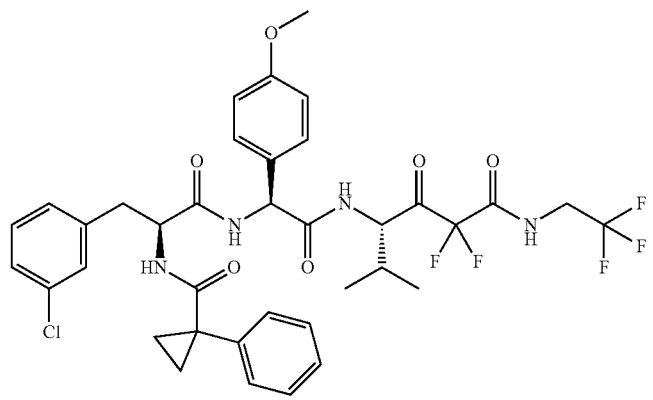 [SMILES: COc1ccc([C@H](NC(=O)[C@H](Cc2cccc(Cl)c2)NC(=O)C2(c3ccccc3)CC2)C(=O)N[C@H](C(=O)C(F)(F)C(=O)NCC(F)(F)F)C(C)C)cc1]<br>N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-1-phenylcyclopropane-1-carboxamide | IIIc | 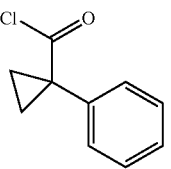 [SMILES: O=C(Cl)C1(c2ccccc2)CC1] | oil colorless 765.3 (M + H)+ |

-continued

| Ex | Structure/Name | Intermediate III | Acid chloride | Form Color MS |
|---|---|---|---|---|
| 55 | 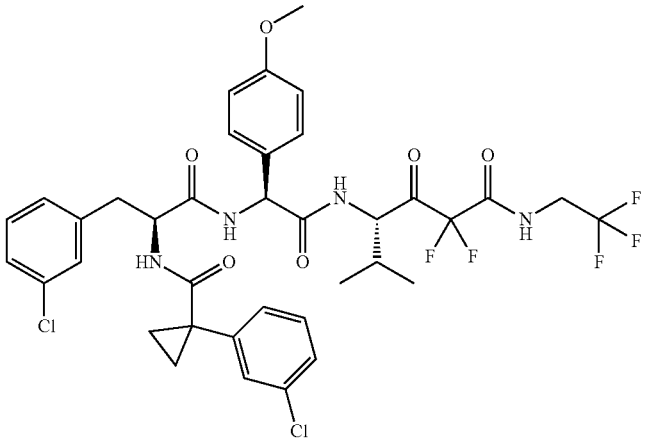 [SMILES: COc1ccc([C@H](NC(=O)[C@H](Cc2cccc(Cl)c2)NC(=O)C2(c3cccc(Cl)c3)CC2)C(=O)N[C@H](C(=O)C(F)(F)C(=O)NCC(F)(F)F)C(C)C)cc1]<br>1-(3-chlorophenyl)-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]cyclopropane-1-carboxamide | IIIc | 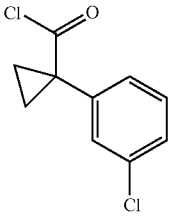 [SMILES: O=C(Cl)C1(c2cccc(Cl)c2)CC1] | oil colorless 799.3 (M + H)+ |
| 57 | 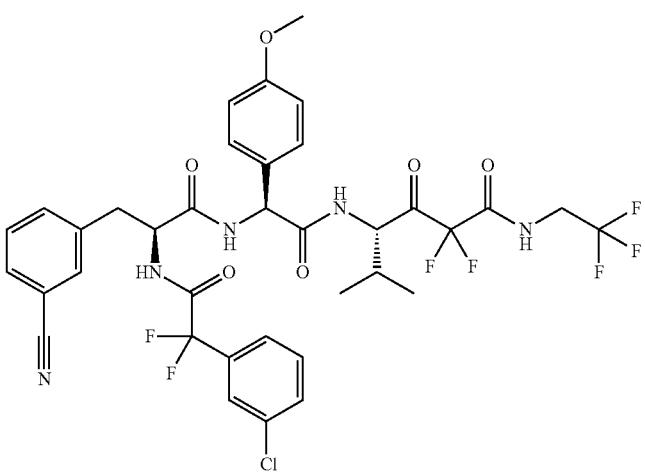 [SMILES: COc1ccc([C@H](NC(=O)[C@H](Cc2cccc(C#N)c2)NC(=O)C(F)(F)c2cccc(Cl)c2)C(=O)N[C@H](C(=O)C(F)(F)C(=O)NCC(F)(F)F)C(C)C)cc1]<br>(4S)-4-[[(2S)-2-[[(2S)-2-[[2-(3-chlorophenyl)-2,2-difluoroacetyl]amino]-3-(3-cyanophenyl)propanoyl]amino]-2-(4-methoxyphenyl)acetyl]amino]-2,2-difluoro-5-methyl-3-oxo-N-(2,2,2-trifluoroethyl)hexanamide | IIIe | 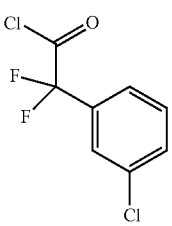 [SMILES: O=C(Cl)C(F)(F)c1cccc(Cl)c1] | solid white 800.3 (M + H)+ |

Example 61

(4S)-4-[[(2S)-2-[[(2S)-2-[[2-(3-Chlorophenyl)-2,2-difluoroacetyl]amino]-3-hydroxypropanoyl]-amino]-2-(4-methoxyphenyl)acetyl]amino]-2,2-difluoro-5-methyl-3-oxo-N-(2,2,2-trifluoroethyl)hexanamide

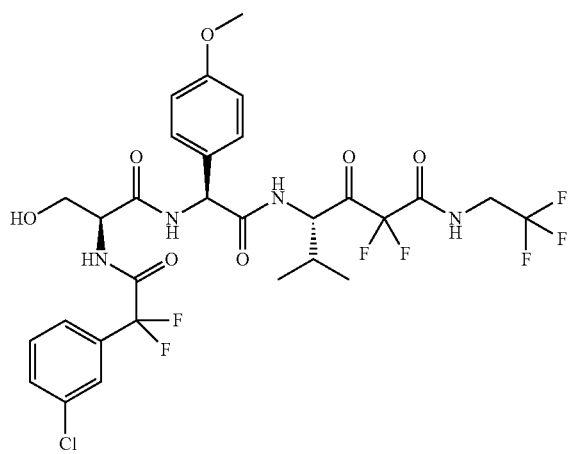 [SMILES: COc1ccc([C@H](NC(=O)[C@H](CO)NC(=O)C(F)(F)c2cccc(Cl)c2)C(=O)N[C@H](C(=O)C(F)(F)C(=O)NCC(F)(F)F)C(C)C)cc1]

A] (3R,4S)-4-[[(2S)-2-[[(2S)-3-[tert-Butyl(dimethyl)silyl]oxy-2-[[2-(3-chlorophenyl)-2,2-difluoroacetyl]amino]propanoyl]amino]-2-(4-methoxyphenyl)acetyl]amino]-2,2-difluoro-3-hydroxy-5-methyl-N-(2,2,2-trifluoroethyl)hexanamide

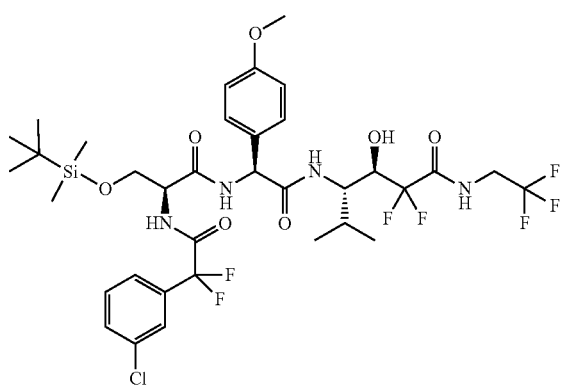 [SMILES: COc1ccc([C@H](NC(=O)[C@H](CO[Si](C)(C)C(C)(C)C)NC(=O)C(F)(F)c2cccc(Cl)c2)C(=O)N[C@@H](C(C)C)[C@@H](O)C(F)(F)C(=O)NCC(F)(F)F)cc1]

To a mixture of (4S)-4-((S)-2-amino-2-(4-methoxyphenyl)acetamido)-2,2-difluoro-3-hydroxy-5-methyl-N-(2,2,2-trifluoroethyl)hexanamide hydrochloride (Intermediate IIb, 175 mg, 366 µmol, Eq: 1) and (S)-3-((tert-butyldimethylsilyl)oxy)-2-(2-(3-chlorophenyl)-2,2-difluoroacetamido)-propanoic acid Intermediate (IVii, 150 mg, 368 µmol, Eq: 1) in DMF (8 ml) were added at 0° C. N,N-diisopropylethylamine (237 mg, 320 µl, 1.83 mmol, Eq: 5) and HATU (167 mg, 439 µmol, Eq: 1.2), and the reaction mixture was stirred for 1 hr at 0° C. The reaction was quenched with sat. NaHCO$_3$+ice and extracted with EtOAc (2×25 mL) The organic layers were washed with NH$_4$Cl sol., then with brine, they were combined, dried over Na$_2$SO$_4$ and concentrated in vacuo.

The crude material was purified by flash chromatography (silica gel, 20 g, 10% to 60% EtOAc in heptane) to produce 175 mg of the title compound as off-white foam; MS: 831.3 (M+H)$^+$.

B] (4S)-4-[[(2S)-2-[[(2S)-3-[tert-Butyl(dimethyl)silyl]oxy-2-[[2-(3-chlorophenyl)-2,2-difluoroacetyl]amino]propanoyl]amino]-2-(4-methoxyphenyl)acetyl]amino]-2,2-difluoro-5-methyl-3-oxo-N-(2,2,2-trifluoroethyl)hexanamide

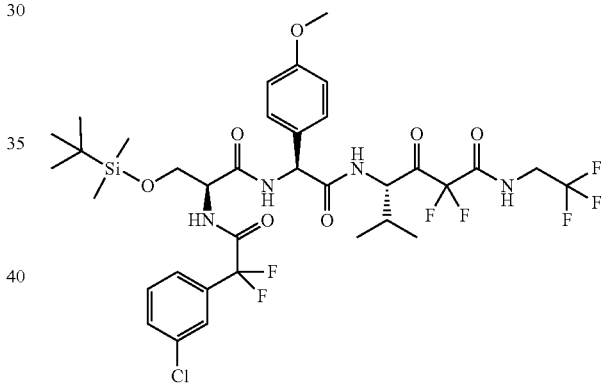

In a 10 mL round-bottomed flask, the above prepared (4S)-4-((S)-2-((S)-3-((tert-butyldimethylsilyl)oxy)-2-(2-(3-chlorophenyl)-2,2-difluoroacetamido)propanamido)-2-(4-methoxyphenyl)acetamido)-2,2-difluoro-3-hydroxy-5-methyl-N-(2,2,2-trifluoroethyl)-hexanamide (169 mg, 203 µmol, Eq: 1) was combined with DCM (6 ml) to give a colorless solution. Dess-Martin periodinane 15% in CH2Cl2 (862 mg, 633 µl, 305 µmol, Eq: 1.5) was added at 0° C. and the reaction mixture was stirred at rt for 2 h when LC-MS indicated the reaction to be finished. The mixture was treated with sat NH$_4$Cl sol. and extracted with DCM (2×20 mL). The organic layers were washed with brine, dried (Na$_2$SO$_4$) and evaporated. The crude material was purified by flash chromatography (silica gel, 20 g, 10% to 60% EtOAc in heptane) to yield 139 mg of the title product as white semisolid; MS: 829.3 (M+H)$^+$.

C] (4S)-4-[[(2S)-2-[[(2S)-2-[[2-(3-Chlorophenyl)-2,2-difluoroacetyl]amino]-3-hydroxypropanoyl]amino]-2-(4-methoxyphenyl)acetyl]amino]-2,2-difluoro-5-methyl-3-oxo-N-(2,2,2-trifluoroethyl)hexanamide

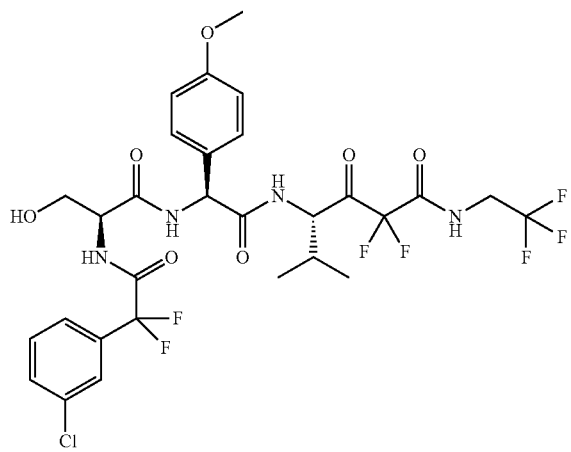 [SMILES: COc1ccc([C@H](NC(=O)[C@H](CO)NC(=O)C(F)(F)c2cccc(Cl)c2)C(=O)N[C@H](C(=O)C(F)(F)C(=O)NCC(F)(F)F)C(C)C)cc1]

In a 10 mL round-bottomed flask, the above prepared (S)-4-((S)-2-((S)-3-((tert-butyldimethylsilyl)oxy)-2-(2-(3-chlorophenyl)-2,2-difluoroacetamido)propanamido)-2-(4-methoxyphenyl)acetamido)-2,2-difluoro-5-methyl-3-oxo-N-(2,2,2-trifluoroethyl)hexanamide (128 mg, 154 µmol, Eq: 1) was combined with THF (8 ml) to give a colorless solution. HCl 4M in dioxane (579 µl, 2.32 mmol, Eq: 15) was added at 0° C., followed by 2 drops H$_2$O. The reaction mixture was stirred at rt for 1 h when LC-MS showed the reaction to be finished. The reaction mixture was poured into H$_2$O and extracted with EtOAc (2×25 mL). The combined organic layers were dried over Na$_2$SO$_4$ and concentrated in vacuo. Precipitation from AcOEt/heptane afforded finally the pure title product as white solid; MS: 715.3 (M+H)$^+$.

Example 62

(4S)-4-[[(2S)-2-[[(2S)-2-[[2,2-Difluoro-2-(3-fluorophenyl)acetyl]amino]-3-hydroxypropanoyl]amino]-2-(4-methoxyphenyl)acetyl]amino]-2,2-difluoro-5-methyl-3-oxo-N-(2,2,2-trifluoroethyl)hexanamide

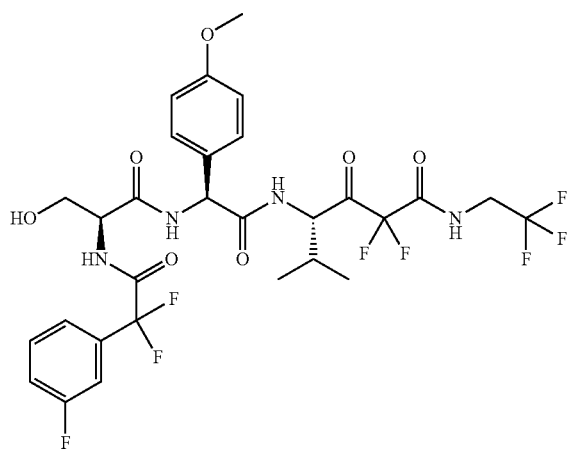 [SMILES: COc1ccc([C@H](NC(=O)[C@H](CO)NC(=O)C(F)(F)c2cccc(F)c2)C(=O)N[C@H](C(=O)C(F)(F)C(=O)NCC(F)(F)F)C(C)C)cc1]

was prepared in analogy to example 61, but using in step A] (2S)-3-[tert-butyl(dimethyl)silyl]oxy-2-[[2-(3-fluorophenyl)-2,2-difluoroacetyl]amino]propanoic acid instead of (S)-3-((tert-butyldimethylsilyl)oxy)-2-(2-(3-chlorophenyl)-2,2-difluoroacetamido)-propanoic acid, as white solid; MS: 699.2 (M+H$^+$).

Example 63 tert-Butyl N-[[4-[(2S)-2-[(3-chlorobenzoyl)amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenyl]methyl]carbamate

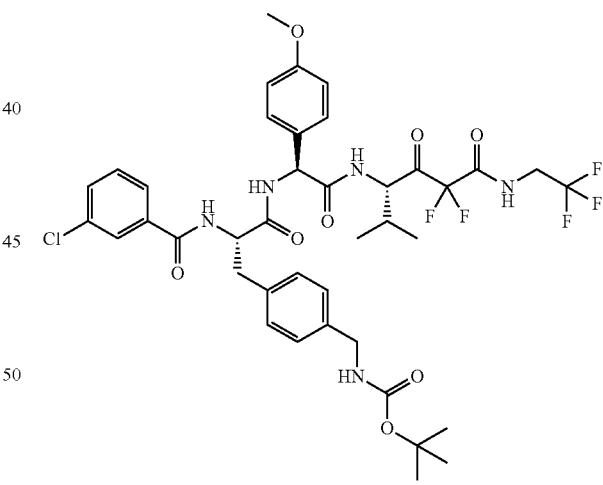

was prepared in analogy to Example 1, using Intermediate IIIg and 3-chlorobenzoic acid as respective building block, as white solid; MS; 795.2 (M+H)$^+$.

Example 64 tert-Butyl N-[[4-[(2S)-2-[[2-(3-chlorophenyl)-2,2-difluoroacetyl]amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenyl]methyl]carbamate

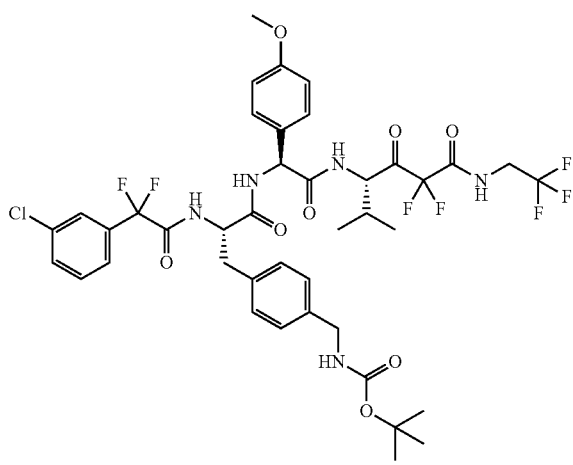 [SMILES: COc1ccc([C@H](NC(=O)[C@H](Cc2ccc(CNC(=O)OC(C)(C)C)cc2)NC(=O)C(F)(F)c2cccc(Cl)c2)C(=O)N[C@H](C(=O)C(F)(F)C(=O)NCC(F)(F)F)C(C)C)cc1]

was prepared in analogy to Example 1, using Intermediate IIIg and 2-(3-chlorophenyl)-2,2-difluoro-acetic acid as respective building block, as white solid; MS; 795.2 (M+H)$^+$.

Example 65

N-[(2S)-3-[4-(Aminomethyl)phenyl]-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-3-chlorobenzamide; TFA

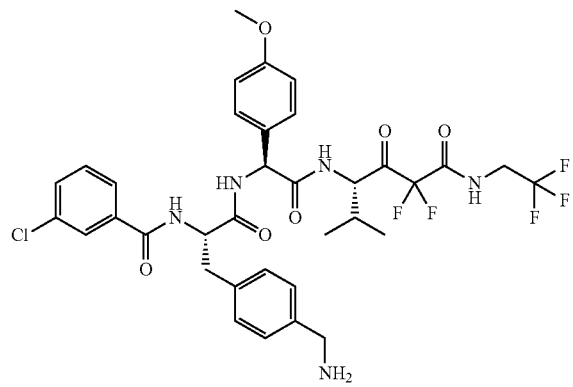 [SMILES: COc1ccc([C@H](NC(=O)[C@H](Cc2ccc(CN)cc2)NC(=O)c2cccc(Cl)c2)C(=O)N[C@H](C(=O)C(F)(F)C(=O)NCC(F)(F)F)C(C)C)cc1]

To a solution of tert-butyl N-[[4-[(2S)-2-[(3-chlorobenzoyl)amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenyl]methyl]carbamate (Example 63, 0.007 g, 0.008 mmol, Eq: 1) in DCM (0.5 ml) was added TFA (0.013 ml, 0.171 mmol, Eq: 20) and the reaction mixture was stirred at room temperature over night. The mixture was concentrated in vacuo and the residue triturated with 0.5 ml of diisopropylether, the solvent was pipetted off and the resulting solid further dried on the high vacuum to give the title compound as TFA salt as light brown solid; MS: 754.3 (M+H)$^+$.

Example 66 was prepared in analogy to Example 65, using tert-butyl N-[[4-[(2S)-2-[[2-(3-chlorophenyl)-2,2-difluoroacetyl]amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenyl]methyl]carbamate (Example 64) instead of Example 63, as light brown solid; MS: 804.3. (M+H)$^+$.

Example 67

(4S)-4-[[(2S)-2-[[(2S)-2-[[2,2-Difluoro-2-(3-fluorophenyl)acetyl]amino]-3-methoxypropanoyl]amino]-2-(4-methoxyphenyl)acetyl]amino]-2,2-difluoro-5-methyl-3-oxo-N-(2,2,2-trifluoroethyl)hexanamide

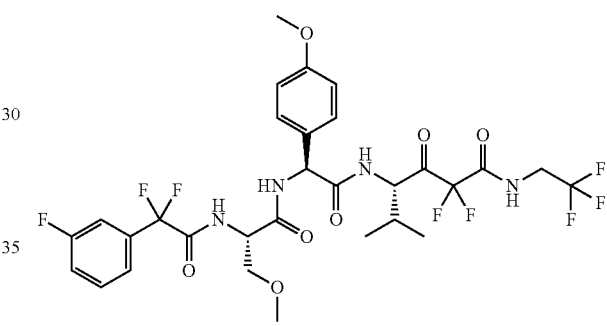

was prepared in analogy to Example 1, using Intermediate IIIf and 2-(3-fluorophenyl)-2,2-difluoro-acetic acid as respective building block, as colorless waxy solid; MS; 713.2.2 (M+H)$^+$.

Example 68

(4S)-4-[[(2S)-2-[[(2S)-2-[[2-(3,4-Dichlorophenyl)-2,2-difluoroacetyl]amino]-3-methoxypropanoyl]amino]-2-(4-methoxyphenyl)acetyl]amino]-2,2-difluoro-5-methyl-3-oxo-N-(2,2,2-trifluoroethyl)hexanamide

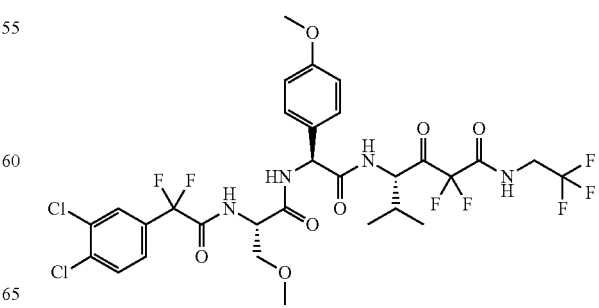

was prepared in analogy to Example 1, using Intermediate IIIf and 2-(3,4-dichlorophenyl)-2,2-difluoro-acetic acid as respective building block, as colorless waxy solid; MS; 763.2 (M+H)+.

Example 69

(4S)-4-[[(2S)-2-[[(2S)-2-[[2-(2,5-Dichlorophenyl)-2,2-difluoroacetyl]amino]-3-methoxypropanoyl]amino]-2-(4-methoxyphenyl)acetyl]amino]-2,2-difluoro-5-methyl-3-oxo-N-(2,2,2-trifluoroethyl)hexanamide

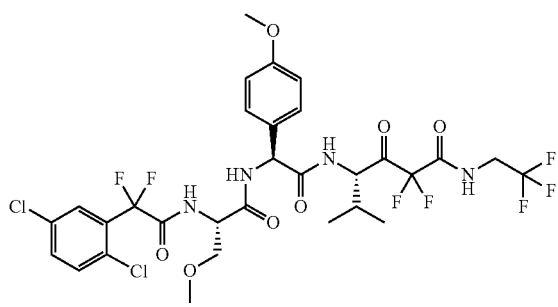 [SMILES: COC[C@H](NC(=O)C(F)(F)c1cc(Cl)ccc1Cl)C(=O)N[C@H](C(=O)N[C@H](C(=O)C(F)(F)C(=O)NCC(F)(F)F)C(C)C)c1ccc(OC)cc1]

was prepared in analogy to Example 1, using Intermediate IIIf and 2-(2,5-dichlorophenyl)-2,2-difluoro-acetic acid as respective building block, as white solid; MS; 763.2 (M+H)+.

Example 70

(4S)-4-[[(2S)-2-[[(2S)-2-[[2-(3-Chlorophenyl)-2,2-difluoroacetyl]amino]-3-methoxypropanoyl]amino]-2-(4-methoxyphenyl)acetyl]amino]-N-[2-(1,1-dioxo-1,4-thiazinan-4-yl)ethyl]-2,2-difluoro-5-methyl-3-oxohexanamide

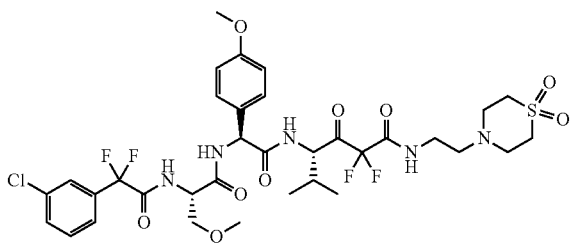 [SMILES: COC[C@H](NC(=O)C(F)(F)c1cccc(Cl)c1)C(=O)N[C@H](C(=O)N[C@H](C(=O)C(F)(F)C(=O)NCCN1CCS(=O)(=O)CC1)C(C)C)c1ccc(OC)cc1]

was prepared in analogy to Example 1, using Intermediate IIIh and 2-(3-chlorophenyl)-2,2-difluoro-acetic acid as respective building block, as white solid; MS; 809.0 (M+H)+.

Example 71

N-[(2S)-1-[[(1S)-2-[[(3S)-6-[2-(1,1-Dioxo-1,4-thiazinan-4-yl)ethylamino]-5,5-difluoro-2-methyl-4,6-dioxohexan-3-yl]amino]-1-(4-methoxyphenyl)-2-oxoethyl]amino]-3-methoxy-1-oxopropan-2-yl]-1-(trifluoromethyl)cyclopentane-1-carboxamide

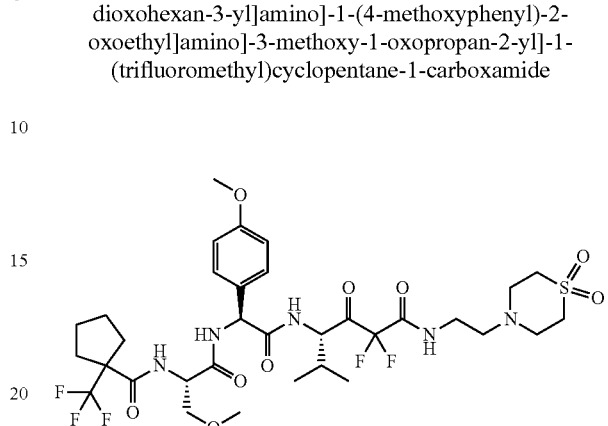

was prepared in analogy to Example 1, using Intermediate IIIh and 1-(trifluoromethyl)cyclopentanecarboxylic acid as respective building block, as white solid; MS; 784.7 (M+H)+.

Example A

A compound of formula (I) can be used in a manner known per se as the active ingredient for the production of tablets of the following composition:

| Per tablet | |
| --- | --- |
| Active ingredient | 200 mg |
| Microcrystalline cellulose | 155 mg |
| Corn starch | 25 mg |
| Talc | 25 mg |
| Hydroxypropylmethylcellulose | 20 mg |
| Total amount | 425 mg |

Example B

A compound of formula (I) can be used in a manner known per se as the active ingredient for the production of capsules of the following composition:

| Per capsule | |
| --- | --- |
| Active ingredient | 100.0 mg |
| Corn starch | 20.0 mg |
| Lactose | 95.0 mg |
| Talc | 4.5 mg |
| Magnesium stearate | 0.5 mg |
| Total amount | 220.0 mg |

The invention claimed is:

1. A compound of formula (I)

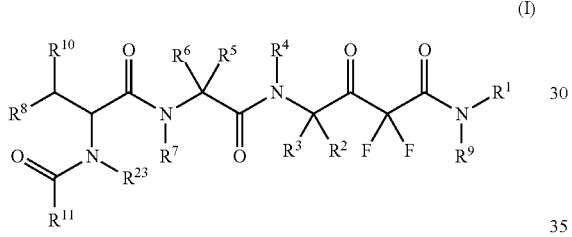

or a pharmaceutically acceptable salt thereof, wherein:

$R^1$ is selected from:
i) $C_{1-6}$-alkyl,
ii) $C_{3-8}$-cycloalkyl substituted with $R^{24}$, $R^{25}$ and $R^{26}$,
iii) halo-$C_{1-6}$-alkyl,
iv) heterocycloalkyl-$C_{1-6}$-alkyl substituted with $R^{24}$, $R^{25}$ and $R^{26}$,
v) aryl-$C_{1-6}$-alkyl substituted with $R^{24}$, $R^{25}$ and $R^{26}$, and
vi) heteroaryl-$C_{1-6}$-alkyl substituted with $R^{24}$, $R^{25}$ and $R^{26}$;

$R^2$, $R^3$, $R^4$, $R^6$, $R^7$, $R^9$, $R^{10}$ and $R^{23}$ are independently selected from:
i) H,
ii) $C_{1-6}$-alkyl, and
iii) $C_{3-8}$-cycloalkyl;

$R^5$ is selected from:
i) aryl substituted with $R^{12}$, $R^{13}$ and $R^{14}$,
ii) aryl-$C_{1-6}$-alkyl substituted with $R^{12}$, $R^{13}$ and $R^{14}$,
iii) heteroaryl substituted with $R^{12}$, $R^{13}$ and $R^{14}$, and
iv) heteroaryl-$C_{1-6}$-alkyl substituted with $R^{12}$, $R^{13}$ and $R^{14}$;

$R^8$ is selected from:
i) H,
ii) hydroxy,
iii) amino-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein the arylcarbonyl and the heteroarylcarbonyl are substituted with $R^{15}$, $R^{16}$ and $R^{17}$,
iv) aminocarbonyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein the arylcarbonyl and the heteroarylcarbonyl are substituted with $R^{15}$, $R^{16}$ and $R^{17}$,
v) aminocarbonyl-$C_{1-6}$-alkyl substituted on the nitrogen atom by one or two substituents selected from H, $C_{1-6}$-alkylcarbonyl, $C_{1-6}$-alkoxycarbonyl, $C_{1-6}$-alkyl, arylcarbonyl and heteroarylcarbonyl, wherein the arylcarbonyl and the heteroarylcarbonyl are substituted with $R^{15}$, $R^{16}$ and $R^{17}$,
vi) carboxy,
vii) carboxy-$C_{1-6}$-alkyl,
viii) $C_{1-6}$-alkoxy,
ix) $C_{1-6}$-haloalkoxy,
x) $C_{1-6}$-alkoxycarbonyl,
xi) $C_{1-6}$-alkoxycarbonyl-$C_{1-6}$-alkyl,
xii) $C_{3-8}$-cycloalkyl,
xiii) aryl substituted with $R^{15}$, $R^{16}$ and $R^{17}$,
xiv) aryl-$C_{1-6}$-alkyl substituted with $R^{15}$, $R^{16}$ and $R^{17}$,
xv) aryl-$C_{1-6}$-alkoxy substituted with $R^{15}$, $R^{16}$ and $R^{17}$,
xvi) heteroaryl substituted with $R^{15}$, $R^{16}$ and $R^{17}$,
xvii) heteroaryl-$C_{1-6}$-alkyl substituted with $R^{15}$, $R^{16}$ and $R^{17}$,
xviii) heteroaryl-$C_{1-6}$-alkoxy substituted with $R^{15}$, $R^{16}$ and $R^{17}$,
xix) heterocycloalkyl substituted with $R^{15}$, $R^{16}$ and $R^{17}$,
xx) heterocycloalkyl-$C_{1-6}$-alkyl substituted with $R^{15}$, $R^{16}$ and $R^{17}$, and
xxi) heterocycloalkyl-$C_{1-6}$-alkoxy substituted with $R^{15}$, $R^{16}$ and $R^{17}$;

$R^{11}$ is selected from:
i) amino-$C_{1-6}$-alkyl substituted on the nitrogen atom by $R^{21}$ and $R^{22}$,
ii) $C_{3-8}$-cycloalkyl substituted with $R^{18}$, $R^{19}$ and $R^{20}$,
iii) $C_{3-8}$-cycloalkyl-$C_{1-6}$-alkyl substituted with $R^{18}$, $R^{19}$ and $R^{20}$,
iv) $C_{3-8}$-cycloalkyl(halo)-$C_{1-6}$-alkyl substituted with $R^{18}$, $R^{19}$ and $R^{20}$,
v) aryl substituted with $R^{18}$, $R^{19}$ and $R^{20}$,
vi) aryl-$C_{1-6}$-alkyl substituted with $R^{18}$, $R^{19}$ and $R^{20}$,
vii) aryl-$C_{3-8}$-cycloalkyl substituted with $R^{18}$, $R^{19}$ and $R^{20}$, viii) aryl-heterocycloalkyl substituted with $R^{18}$, $R^{19}$ and $R^{20}$,
ix) aryl(halo)-$C_{1-6}$-alkyl substituted with $R^{18}$, $R^{19}$ and $R^{20}$,
x) aryl(halo)-$C_{3-8}$-cycloalkyl substituted with $R^{18}$, $R^{19}$ and $R^{20}$,
xi) aryl(halo)-heterocycloalkyl substituted with $R^{18}$, $R^{19}$ and $R^{20}$,
xii) aryloxy-$C_{1-6}$-alkyl substituted with $R^{18}$, $R^{19}$ and $R^{20}$,
xiii) aryloxy-$C_{3-8}$-cycloalkyl substituted with $R^{18}$, $R^{19}$ and $R^{20}$,
xiv) aryloxy-heterocycloalkyl substituted with $R^{18}$, $R^{19}$ and $R^{20}$,
xv) aryloxy(halo)-$C_{3-8}$-cycloalkyl substituted with $R^{18}$, $R^{19}$ and $R^{20}$,
xvi) aryloxy(halo)-heterocycloalkyl substituted with $R^{18}$, $R^{19}$ and $R^{20}$,
xvii) aryloxy(halo)-$C_{1-6}$-alkyl,
xviii) heterocycloalkyl substituted with $R^{18}$, $R^{19}$ and $R^{20}$,
xix) heterocycloalkyl-$C_{1-6}$-alkyl substituted with $R^{18}$, $R^{19}$ and $R^{20}$,
xx) heterocycloalkyl-$C_{3-8}$-cycloalkyl substituted with $R^{18}$, $R^{19}$ and $R^{20}$,
xxi) heterocycloalkyl(halo)-$C_{3-8}$-cycloalkyl substituted with $R^{18}$, $R^{19}$ and $R^{20}$,
xxii) heterocycloalkyl(halo)-$C_{1-6}$-alkyl substituted with $R^{18}$, $R^{19}$ and $R^{20}$,
xxiii) heteroaryl substituted with $R^{18}$, $R^{19}$ and $R^{20}$,
xxiv) heteroaryl-$C_{1-6}$-alkyl substituted with $R^{18}$, $R^{19}$ and $R^{20}$,
xxv) heteroaryl-$C_{3-8}$-cycloalkyl substituted with $R^{18}$, $R^{19}$ and $R^{20}$,
xxvi) heteroaryl(halo)-$C_{3-8}$-cycloalkyl substituted with $R^{18}$, $R^{19}$ and $R^{20}$,
xxvii) heteroaryl(halo)-$C_{1-6}$-alkyl substituted with $R^{18}$, $R^{19}$ and $R^{20}$,
xxviii) heteroaryloxy-$C_{1-6}$-alkyl substituted with $R^{18}$, $R^{19}$ and $R^{20}$,
xxix) heteroaryloxy-$C_{3-8}$-cycloalkyl substituted with $R^8$, $R^{19}$ and $R^{20}$,
xxx) heteroaryloxy(halo)-$C_{3-8}$-cycloalkyl substituted with $R^{18}$, $R^{19}$ and $R^{20}$, and
xxxi) heteroaryloxy(halo)-$C_{1-6}$-alkyl substituted with $R^8$, $R^{19}$ and $R^{20}$;
$R^{12}$, $R^{13}$, $R^{14}$, $R^{15}$, $R^{16}$, $R^{17}$, $R^{18}$, $R^{19}$, $R^{20}$, $R^{24}$, $R^{25}$ and $R^{26}$ are independently selected from:
i) H,
ii) cyano,
iii) halogen,
iv) oxo,
v) $C_{1-6}$-alkyl,
vi) amino substituted on the nitrogen atom by two substituents independently selected from H, $C_{1-6}$-alkyl, $C_{1-6}$-alkoxycarbonyl, arylcarbonyl and heteroarylcarbonyl,
vii) amino-$C_{1-6}$-alkyl substituted on the nitrogen atom by two substituents independently selected from H, $C_{1-6}$-alkyl, $C_{1-6}$-alkoxycarbonyl, arylcarbonyl and heteroarylcarbonyl,
viii) $C_{1-6}$-alkyl,
ix) halo-$C_{1-6}$-alkyl,
x) $C_{3-8}$-cycloalkyl,
xi) $C_{1-6}$-alkoxycarbonyl-$C_{1-6}$-alkyl,
xii) carboxy-$C_{1-6}$-alkyl,
xiii) $C_{1-6}$-alkoxycarbonyl-$C_{1-6}$-alkylaminocarbonyl-$C_{1-6}$-alkyl,
xiv) carboxy-$C_{1-6}$-alkylaminocarbonyl-$C_{1-6}$alkyl,
xv) $C_{1-6}$-alkoxy,
xvi) halo-$C_{1-6}$-alkoxy,
xvii) $C_{1-6}$-alkoxycarbonyl-$C_{1-6}$-alkoxy,
xviii) carboxy-$C_{1-6}$-alkoxy,
xix) $C_{1-6}$-alkoxycarbonyl-$C_{1-6}$-alkylaminocarbonyl-$C_{1-6}$-alkoxy,
xx) carboxy-$C_{1-6}$-alkylaminocarbonyl-$C_{1-6}$-alkoxy, and
xxi) heterocycloalkyl; and
$R^{21}$ and $R^{22}$ are independently selected from:
i) H,
ii) $C_{1-6}$-alkoxycarbonyl,
iii) carboxy-$C_{1-6}$-alkyl,
iv) arylcarbonyl, and
v) heteroarylcarbonyl.

2. The compound or a pharmaceutically acceptable salt thereof according to claim 1, wherein:
$R^1$ is halo-$C_{1-6}$-alkyl;
$R^2$ is selected from:
i) $C_{1-6}$-alkyl, and
ii) $C_{3-8}$-cycloalkyl;
$R^3$, $R^4$, $R^6$, $R^7$, $R^9$, $R^{10}$ and $R^{23}$ are H;
$R^5$ is phenyl substituted with $R^{12}$, $R^{13}$ and $R^{14}$;
$R^8$ is selected from:
i) H,
ii) hydroxy, and
iii) phenyl substituted with $R^{15}$, $R^{16}$ and $R^{17}$;
$R^{11}$ is selected from:
i) amino-$C_{1-6}$-alkyl substituted on the nitrogen atom by $R^{21}$ and $R^{22}$,
ii) phenyl substituted with $R^{18}$, $R^{19}$ and $R^{20}$,
iii) phenyl-$C_{1-6}$-alkyl substituted with $R^{18}$, $R^{19}$ and $R^{20}$,
iv) phenyl-$C_{3-8}$-cycloalkyl substituted with $R^{18}$, $R^{19}$ and $R^{20}$,
v) phenyl(halo)-$C_{1-6}$-alkyl substituted with $R^{18}$, $R^{19}$ and $R^{20}$, and
vi) heteroaryl substituted with $R^{18}$, $R^{19}$ and $R^{20}$, wherein the heteroaryl is selected from pyrazinyl, pyridinyl, pyrimidinyl and thiophenyl;
$R^{12}$ is selected from:
i) H, and
ii) $C_{1-6}$-alkoxy;
$R^{13}$, $R^{14}$, $R^{17}$ and $R^{20}$ are H;
$R^{15}$ is selected from:
i) $C_{1-6}$-alkyl,
ii) cyano,
iii) halogen, and
iv) carboxy-$C_{1-6}$-alkoxy;
$R^{16}$ is selected from:
i) H, and
ii) halogen;
$R^{18}$ is selected from:
i) H,
ii) halogen,
iii) halo-$C_{1-6}$-alkoxy,
iv) cyano,
v) amino substituted on the nitrogen atom by two $C_{1-6}$-alkyl,
vi) $C_{1-6}$-alkoxycarbonyl-$C_{1-6}$-alkoxy,
vii) carboxy-$C_{1-6}$-alkoxy, and
viii) morpholinyl;
$R^{19}$ is selected from:
i) H, and
ii) halogen;
$R^{21}$ is pyridinylcarbonyl; and
$R^{22}$ is H.

3. The compound or a pharmaceutically acceptable salt thereof according to claim 1, wherein $R^1$ is halo-$C_{1-6}$-alkyl.

4. The compound or a pharmaceutically acceptable salt thereof according to claim 1, wherein $R^1$ is trifluoroethyl.

5. The compound or a pharmaceutically acceptable salt thereof according to claim 1, wherein $R^2$ is $C_{1-6}$-alkyl.

6. The compound or a pharmaceutically acceptable salt thereof according to claim 1, wherein $R^2$ is isopropyl.

7. The compound or a pharmaceutically acceptable salt thereof according to claim 1, wherein $R^3$, $R^4$, $R^6$, $R^7$, $R^9$, $R^{10}$ and $R^{23}$ are H.

8. The compound or a pharmaceutically acceptable salt thereof according to claim 1, wherein $R^5$ is phenyl substituted with $R^{12}$, $R^{13}$ and $R^{14}$.

9. The compound or a pharmaceutically acceptable salt thereof according to claim 1, wherein $R^5$ is phenyl substituted with one $C_{1-6}$-alkoxy.

10. The compound or a pharmaceutically acceptable salt thereof according to claim 1, wherein $R^8$ is selected from:
    i) H,
    ii) hydroxy, and
    iii) phenyl substituted with $R^{15}$, $R^{16}$ and $R^1$.

11. The compound or a pharmaceutically acceptable salt thereof according to claim 1, wherein $R^8$ is selected from:
    i) hydroxy, and
    ii) phenyl substituted with $R^{15}$, $R^{16}$ and $R^1$.

12. The compound or a pharmaceutically acceptable salt thereof according to claim 1, wherein $R^8$ is phenyl substituted with $R^{15}$, $R^{16}$ and $R^{17}$.

13. The compound or a pharmaceutically acceptable salt thereof according to claim 1, wherein $R^{11}$ is selected from:
    i) amino-$C_{1-6}$-alkyl substituted on the nitrogen atom by $R^{21}$ and $R^{22}$,
    ii) phenyl substituted with $R^{18}$, $R^{19}$ and $R^{20}$,
    iii) phenyl-$C_{1-6}$-alkyl substituted with $R^{18}$, $R^{19}$ and $R^{20}$,
    iv) phenyl-$C_{3-8}$-cycloalkyl substituted with $R^{18}$, $R^{19}$ and $R^{20}$,
    v) phenyl(halo)-$C_{1-6}$-alkyl substituted with $R^{18}$, $R^{19}$ and $R^{20}$, and
    vi) heteroaryl substituted with $R^{18}$, $R^{19}$ and $R^{20}$, wherein the heteroaryl is selected from pyrazinyl, pyridinyl, pyrimidinyl and thiophenyl.

14. The compound or a pharmaceutically acceptable salt thereof according to claim 1, wherein $R^{11}$ is selected from:
    i) phenyl substituted with $R^{18}$, $R^{19}$ and $R^{20}$,
    ii) phenyl-$C_{1-6}$-alkyl substituted with $R^{18}$, $R^{19}$ and $R^{20}$,
    iii) phenyl(halo)-$C_{1-6}$-alkyl substituted with $R^{18}$, $R^{19}$ and $R^{20}$, and
    iv) heteroaryl substituted with $R^{18}$, $R^{19}$ and $R^{20}$, wherein the heteroaryl is selected from pyridinyl and thiophenyl.

15. The compound or a pharmaceutically acceptable salt thereof according to claim 1, wherein $R^{11}$ is phenyl substituted with $R^{18}$, $R^{19}$ and $R^{20}$.

16. The compound or a pharmaceutically acceptable salt thereof according to claim 1, wherein $R^{12}$ is selected from:
    i) H, and
    ii) $C_{1-6}$-alkoxy.

17. The compound or a pharmaceutically acceptable salt thereof according to claim 1, wherein $R^{12}$ is $C_{1-6}$-alkoxy.

18. The compound or a pharmaceutically acceptable salt thereof according to claim 1, wherein $R^{13}$, $R^{14}$, $R^{17}$ and $R^{20}$ are H.

19. The compound or a pharmaceutically acceptable salt thereof according to claim 1, wherein $R^{11}$ is selected from:
    i) $C_{1-6}$-alkyl,
    ii) cyano,
    iii) halogen, and
    iv) carboxy-$C_{1-6}$-alkoxy.

20. The compound or a pharmaceutically acceptable salt thereof according to claim 1, wherein $R^{15}$ is selected from:
    i) cyano, and
    ii) halogen.

21. The compound or a pharmaceutically acceptable salt thereof according to claim 1, wherein $R^{15}$ is halogen.

22. The compound or a pharmaceutically acceptable salt thereof according to claim 1, wherein $R^{16}$ is selected from:
    i) H, and
    ii) halogen.

23. The compound or a pharmaceutically acceptable salt thereof according to claim 1, wherein $R^{16}$ is H.

24. The compound or a pharmaceutically acceptable salt thereof according to claim 1, wherein $R^{18}$ is selected from:
    i) H,
    ii) halogen,
    iii) halo-$C_{1-6}$-alkoxy,
    iv) cyano,
    v) amino substituted on the nitrogen atom by two $C_{1-6}$-alkyl,
    vi) $C_{1-6}$-alkoxycarbonyl-$C_{1-6}$-alkoxy,
    vii) carboxy-$C_{1-6}$-alkoxy, and
    viii) morpholinyl.

25. The compound or a pharmaceutically acceptable salt thereof according to claim 1, wherein $R^{18}$ is selected from:
    i) H,
    ii) cyano, and
    iii) halogen.

26. The compound or a pharmaceutically acceptable salt thereof according to claim 1, wherein $R^{18}$ is halogen.

27. The compound or a pharmaceutically acceptable salt thereof according to claim 1, wherein $R^{19}$ is selected from:
    i) H, and
    ii) halogen.

28. The compound or a pharmaceutically acceptable salt thereof according to claim 1, wherein $R^{19}$ is H.

29. The compound or a pharmaceutically acceptable salt thereof according to claim 1, wherein $R^{21}$ is pyridinylcarbonyl.

30. The compound or a pharmaceutically acceptable salt thereof according to claim 1, wherein $R^{22}$ is H.

31. The compound or a pharmaceutically acceptable salt thereof according to claim 1, wherein:
    $R^1$ is halo-$C_{1-6}$-alkyl;
    $R^2$ is $C_{1-6}$-alkyl;
    $R^3$, $R^4$, $R^6$, $R^7$, $R^9$, $R^{10}$ and $R^{23}$ are H;
    $R^5$ is phenyl substituted with one $C_{1-6}$-alkoxy;
    $R^8$ is phenyl substituted with $R^{15}$, $R^{16}$ and $R^{17}$;
    $R^{11}$ is phenyl substituted with $R^{18}$, $R^{19}$ and $R^{20}$;
    $R^{15}$ is selected from:
    i) cyano, and
    ii) halogen;
    $R^{16}$ is selected from:
    i) H, and
    ii) halogen;
    $R^{17}$ and $R^{20}$ are H;
    $R^{18}$ is selected from:
    i) H,
    ii) cyano, and
    iii) halogen; and
    $R^{19}$ is selected from:
    i) H, and
    ii) halogen.

32. The compound according to claim 1, selected from N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]
amino]-1-oxopropan-2-yl]pyridine-4-carboxamide;
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyridine-2-carboxamide;
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyrazine-2-carboxamide;
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyrimidine-5-carboxamide;
N-[(2S)-3-(3,4-dichlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;
N-[(2S)-3-(3,4-dichlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]pyridine-2-carboxamide;
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-5-(difluoromethoxy)pyridine-2-carboxamide;
N-[(2S)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-3-(3-methylphenyl)-1-oxopropan-2-yl]pyridine-2-carboxamide;
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]-5-(difluoromethoxy)pyridine-2-carboxamide;
N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-methylphenyl)-1-oxopropan-2-yl]pyridine-2-carboxamide;
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-5-morpholin-4-ylpyridine-2-carboxamide;
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-5-(dimethylamino)pyridine-2-carboxamide;
N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;
N-[3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;
N-[3-(3-chlorophenyl)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]benzamide;
N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;
N-[(2S)-3-(3-chloro-4-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;
N-[2-[[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]amino]-2-oxoethyl]pyridine-2-carboxamide;
N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;
N-[2-[[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]amino]-2-oxoethyl]pyridine-2-carboxamide;
3-chloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;
N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-hydroxy-1-oxopropan-2-yl]benzamide;
1-(3-chlorophenyl)-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-hydroxy-1-oxopropan-2-yl]cyclopropane-1-carboxamide;
1-(3-chlorophenyl)-N-[(2S,3R)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-hydroxy-1-oxobutan-2-yl]cyclopropane-1-carboxamide;
N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;
1-(3-chlorophenyl)-N-[(2S)-1-[[(1S)-2-[[(3S)-5,5-difluoro-2-methyl-4,6-dioxo-6-(2,2,2-trifluoroethylamino)hexan-3-yl]amino]-2-oxo-1-phenylethyl]amino]-1-oxopropan-2-yl]cyclopropane-1-carboxamide;
1-(3-chlorophenyl)-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]cyclopropane-1-carboxamide;
2,5-dichloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;
3-chloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[(2R)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;

3-chloro-N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

5-chloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]thiophene-2-carboxamide;

5-chloro-N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]thiophene-2-carboxamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-3-cyanobenzamide;

2,5-dichloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

tert-butyl 2-[4-[[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]carbamoyl]phenoxy]acetate;

2-[4-[[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]carbamoyl]phenoxy]acetic acid;

2-[4-[(2S)-2-[[2-(3-chlorophenyl)-2,2-difluoroacetyl]amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetic acid;

2-[4-[(2S)-2-[(3-chlorobenzoyl)amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenoxy]acetic acid;

(4S)-4-[[(2S)-2-[[(2S)-3-(3-chlorophenyl)-2-[[2-(3-chlorophenyl)-2,2-difluoroacetyl]amino]propanoyl]amino]-2-(4-methoxyphenyl)acetyl]amino]-2,2-difluoro-5-methyl-3-oxo-N-(2,2,2-trifluoroethyl)hexanamide;

3-chloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide;

N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]pyridine-2-carboxamide;

2,5-dichloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide;

(4S)-4-[[(2S)-2-[[(2S)-3-(3-chlorophenyl)-2-[[2-(3-chlorophenyl)acetyl]amino]propanoyl]amino]-2-(4-methoxyphenyl)acetyl]amino]-2,2-difluoro-5-methyl-3-oxo-N-(2,2,2-trifluoroethyl)hexanamide;

(4S)-4-[[(2S)-2-[[(2S)-2-[[2-(3-chlorophenyl)-2,2-difluoroacetyl]amino]-3-(3-fluorophenyl)propanoyl]amino]-2-(4-methoxyphenyl)acetyl]amino]-2,2-difluoro-5-methyl-3-oxo-N-(2,2,2-trifluoroethyl)hexanamide;

N-[(2S)-3-(3-chlorophenyl)-1-[[(1S)-2-[[(1S)-1-cyclobutyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide;

3-chloro-N-[(2S)-3-(4-chloro-3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[(2S)-3-(3-cyanophenyl)-1-[[(1S)-2-[[(1S)-1-cyclobutyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide;

N-[(2S)-3-(3-cyanophenyl)-1-[[(1S)-2-[[(1S)-1-cyclobutyl-3,3-difluoro-2,4-dioxo-4-(2,2,2-trifluoroethylamino)butyl]amino]-1-(4-methoxyphenyl)-2-oxoethyl]amino]-1-oxopropan-2-yl]benzamide;

(4S)-4-[[(2S)-2-[[(2S)-2-[[2-(3-chlorophenyl)-2,2-difluoroacetyl]amino]propanoyl]amino]-2-(4-methoxyphenyl)acetyl]amino]-2,2-difluoro-5-methyl-3-oxo-N-(2,2,2-trifluoroethyl)hexanamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-3-fluorobenzamide;

3,5-dichloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-1-phenylcyclopropane-1-carboxamide;

1-(3-chlorophenyl)-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]cyclopropane-1-carboxamide;

3-cyano-N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

(4S)-4-[[(2S)-2-[[(2S)-2-[[2-(3-chlorophenyl)-2,2-difluoroacetyl]amino]-3-(3-cyanophenyl)propanoyl]amino]-2-(4-methoxyphenyl)acetyl]amino]-2,2-difluoro-5-methyl-3-oxo-N-(2,2,2-trifluoroethyl)hexanamide;

3-cyano-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide;

N-[(2S)-3-(3-chlorophenyl)-1-[[(1S)-2-[[(1S)-1-cyclopropyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide;

N-[(2S)-3-(3-cyanophenyl)-1-[[(1S)-2-[[(1S)-1-cyclopropyl-3,3-difluoro-2,4-dioxo-4-(2,2,2-trifluoroethylamino)butyl]amino]-1-(4-methoxyphenyl)-2-oxoethyl]amino]-1-oxopropan-2-yl]pyridine-2-carboxamide; and (4S)-4-[[(2S)-2-[[(2S)-2-[[2-(3-chlorophenyl)-2,2-difluoroacetyl]amino]-3-hydroxypropanoyl]amino]-2-(4-methoxyphenyl)acetyl]amino]-2,2-difluoro-5-methyl-3-oxo-N-(2,2,2-trifluoroethyl)hexanamide;

or a pharmaceutically acceptable salt thereof.

33. The compound according to claim 1, selected from

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;

N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]pyridine-2-carboxamide;

N-[3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

5-chloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]thiophene-2-carboxamide;

5-chloro-N-[(2S)-3-(3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]thiophene-2-carboxamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-3-cyanobenzamide;

2,5-dichloro-N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

3-chloro-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide;

(4S)-4-[[(2S)-2-[[(2S)-3-(3-chlorophenyl)-2-[[2-(3-chlorophenyl)acetyl]amino]propanoyl]amino]-2-(4-methoxyphenyl)acetyl]amino]-2,2-difluoro-5-methyl-3-oxo-N-(2,2,2-trifluoroethyl)hexanamide;

3-chloro-N-[(2S)-3-(4-chloro-3-cyanophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]benzamide;

N-[(2S)-3-(3-chlorophenyl)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-3-fluorobenzamide;

3-cyano-N-[(2S)-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-(3-fluorophenyl)-1-oxopropan-2-yl]benzamide; and (4S)-4-[[(2S)-2-[[(2S)-2-[[2-(3-chlorophenyl)-2,2-difluoroacetyl]amino]-3-hydroxypropanoyl]amino]-2-(4-methoxyphenyl)acetyl]amino]-2,2-difluoro-5-methyl-3-oxo-N-(2,2,2-trifluoroethyl)hexanamide;

or a pharmaceutically acceptable salt thereof.

34. The compound according to claim 1, selected from (4S)-4-[[(2S)-2-[[(2S)-2-[[2,2-difluoro-2-(3-fluorophenyl)acetyl]amino]-3-hydroxypropanoyl]amino]-2-(4-methoxyphenyl)acetyl]amino]-2,2-difluoro-5-methyl-3-oxo-N-(2,2,2-trifluoroethyl)hexanamide;

tert-butyl N-[[4-[(2S)-2-[(3-chlorobenzoyl)amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenyl]methyl]carbamate;

tert-butyl N-[[4-[(2S)-2-[[2-(3-chlorophenyl)-2,2-difluoroacetyl]amino]-3-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-3-oxopropyl]phenyl]methyl]carbamate;

(4S)-4-[[(2S)-2-[[(2S)-2-[[2,2-difluoro-2-(3-fluorophenyl)acetyl]amino]-3-methoxypropanoyl]amino]-2-(4-methoxyphenyl)acetyl]amino]-2,2-difluoro-5-methyl-3-oxo-N-(2,2,2-trifluoroethyl)hexanamide;

(4S)-4-[[(2S)-2-[[(2S)-2-[[2-(3,4-dichlorophenyl)-2,2-difluoroacetyl]amino]-3-methoxypropanoyl]amino]-2-(4-methoxyphenyl)acetyl]amino]-2,2-difluoro-5-methyl-3-oxo-N-(2,2,2-trifluoroethyl)hexanamide;

(4S)-4-[[(2S)-2-[[(2S)-2-[[2-(2,5-dichlorophenyl)-2,2-difluoroacetyl]amino]-3-methoxypropanoyl]amino]-2-(4-methoxyphenyl)acetyl]amino]-2,2-difluoro-5-methyl-3-oxo-N-(2,2,2-trifluoroethyl)hexanamide;

(4S)-4-[[(2S)-2-[[(2S)-2-[[2-(3-chlorophenyl)-2,2-difluoroacetyl]amino]-3-methoxypropanoyl]amino]-2-(4-methoxyphenyl)acetyl]amino]-N-[2-(1,1-dioxo-1,4-thiazinan-4-yl)ethyl]-2,2-difluoro-5-methyl-3-oxohexanamide;

N-[(2S)-1-[[(1S)-2-[[(3S)-6-[2-(1,1-dioxo-1,4-thiazinan-4-yl)ethylamino]-5,5-difluoro-2-methyl-4,6-dioxohexan-3-yl]amino]-1-(4-methoxyphenyl)-2-oxoethyl]amino]-3-methoxy-1-oxopropan-2-yl]-1-(trifluoromethyl)cyclopentane-1-carboxamide;

or a pharmaceutically acceptable salt thereof, and

N-[(2S)-3-[4-(aminomethyl)phenyl]-1-[[(1S)-2-[[(3S)-5,5-difluoro-2-methyl-4,6-dioxo-6-(2,2,2-trifluoroethylamino)hexan-3-yl]amino]-1-(4-methoxyphenyl)-2-oxoethyl]amino]-1-oxopropan-2-yl]-3-chlorobenzamide trifluoroacetic acid; and (4S)-4-[[(2S)-2-[[(2S)-3-[4-(aminomethyl)phenyl]-2-[[2-(3-chlorophenyl)-2,2-difluoroacetyl]amino]propanoyl]amino]-2-(4-methoxyphenyl)acetyl]amino]-2,2-difluoro-5-methyl-3-oxo-N-(2,2,2-trifluoroethyl)hexanamide, trifluoroacetic acid.

35. The compound or a pharmaceutically acceptable salt thereof according to claim 1, wherein:

$R^1$ is halo-$C_{1-6}$-alkyl;
$R^2$ is $C_{1-6}$-alkyl;
$R^3$, $R^4$, $R^6$, $R^7$, $R^9$, $R^{13}$ and $R^{14}$ are each H;
$R^5$ is aryl substituted with $R^{12}$, $R^{13}$ and $R^{14}$; and
$R^{12}$ is $C_{1-6}$-alkoxy.

36. The compound or a pharmaceutically acceptable salt thereof according to claim 1, which is prepared according to a process comprising i) reacting a compound of formula (III) with a compound of formula (IV) to produce a compound of formula (II)

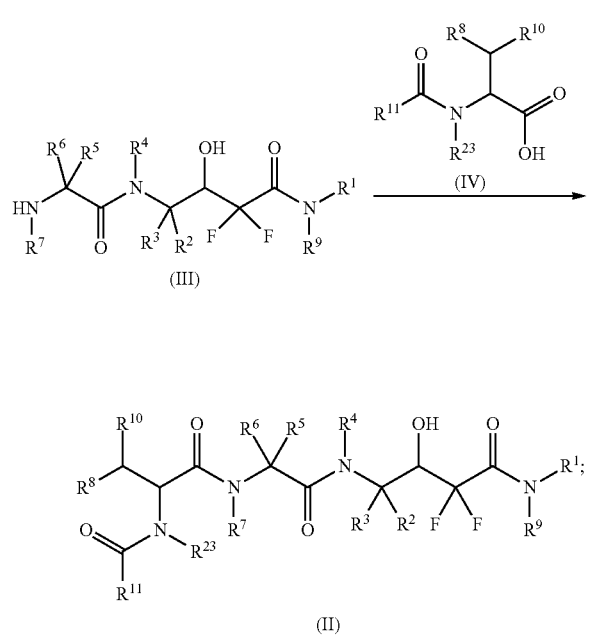

(II)

and ii) reacting a compound of formula (II) obtained from i) under oxidative conditions

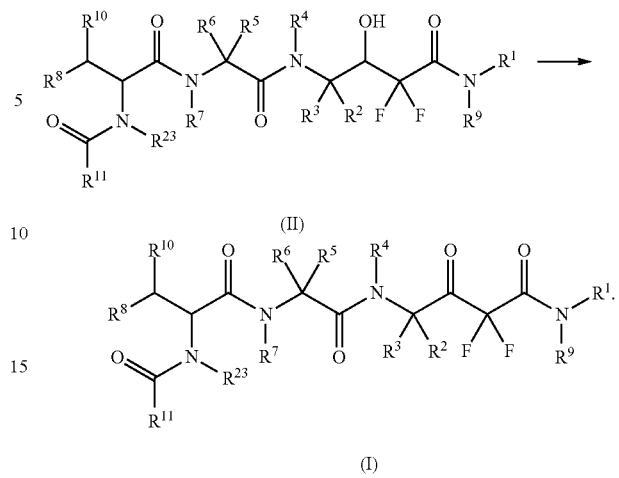

37. A pharmaceutical composition comprising a compound according to claim 1, or a pharmaceutically acceptable salt thereof.

38. A method for the treatment of high-temperature requirement protein A1 (HtrA1)-mediated ocular disease selected from the group consisting of wet or dry age-related macular degeneration, geographic atrophy, diabetic retinopathy, retinopathy of prematurity and polypoidal choroidal vasculopathy, wherein the method comprises administering an effective amount of a compound according to claim 32, or a pharmaceutically acceptable salt thereof.

* * * * *

SEQUENCE LISTING

```
<160> NUMBER OF SEQ ID NOS: 1

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term (7-Methoxycoumarin-4-yl)acetyl
<220> FEATURE:
<221> NAME/KEY: MOD_RES
<222> LOCATION: (9)..(9)
<223> OTHER INFORMATION: Lys(2,4-Dinitrophenyl)

<400> SEQUENCE: 1

Ile Arg Arg Val Ser Tyr Ser Phe Lys Lys
1               5                   10
```